United States Patent
Angermann et al.

(10) Patent No.: US 9,101,133 B2
(45) Date of Patent: Aug. 11, 2015

(54) PHENYL-SUBSTITUTED BICYCLOOCTANE-1,3-DIONE-DERIVATIVES

(75) Inventors: Alfred Angermann, Kriftel (DE); Stefan Lehr, Liederbach (DE); Guido Bojack, Wiesbaden-Naurod (DE); Reiner Fischer, Monheim (DE); Isolde Häuser-Hahn, Leverkusen (DE); Ines Heinemann, Hofheim (DE); Elmar Gatzweiler, Bad Nauheim (DE); Christopher Hugh Rosinger, Hofheim (DE); Arnd Voerste, Köln (DE); Dieter Feucht, Eschborn (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 226 days.

(21) Appl. No.: 13/882,791

(22) PCT Filed: Oct. 28, 2011

(86) PCT No.: PCT/EP2011/069040
§ 371 (c)(1),
(2), (4) Date: Jul. 15, 2013

(87) PCT Pub. No.: WO2012/059436
PCT Pub. Date: May 10, 2012

(65) Prior Publication Data
US 2013/0316906 A1 Nov. 28, 2013

(30) Foreign Application Priority Data
Nov. 2, 2010 (EP) .................................... 10189670

(51) Int. Cl.
*A01N 35/06* (2006.01)
*A01N 35/02* (2006.01)
(Continued)

(52) U.S. Cl.
CPC ................ *A01N 35/06* (2013.01); *A01N 35/02* (2013.01); *A01N 35/10* (2013.01); *A01N 37/08* (2013.01); *A01N 37/34* (2013.01); *A01N 43/26* (2013.01); *A01N 43/28* (2013.01); *A01N 43/30* (2013.01); *A01N 43/32* (2013.01); *A01N 43/36* (2013.01); *A01N 43/78* (2013.01); *A01N 43/80* (2013.01); *A01N 43/84* (2013.01); *A01N 43/86* (2013.01); *A01N 47/18* (2013.01); *C07C 45/513* (2013.01); *C07C 49/67* (2013.01); *C07C 49/753* (2013.01); *C07C 49/757* (2013.01); *C07C 67/14* (2013.01); *C07C 67/29* (2013.01); *C07C 67/313* (2013.01); *C07C 68/02* (2013.01); *C07C 69/007* (2013.01); *C07C 69/013* (2013.01); *C07C 69/157* (2013.01); *C07C 69/24* (2013.01); *C07C 69/30* (2013.01); *C07C 69/738* (2013.01); *C07C 69/757* (2013.01); *C07C 69/96* (2013.01); *C07C 233/58* (2013.01); *C07C 251/40* (2013.01); *C07C 251/42* (2013.01); *C07C 251/52* (2013.01); *C07C 255/40* (2013.01); *C07C 255/47* (2013.01); *C07C 271/10* (2013.01);
(Continued)

(58) Field of Classification Search
CPC ....... A01N 35/02; A01N 35/10; A01N 37/08; A01N 37/34; A01N 43/26
USPC .................................. 504/226, 266, 283, 291
See application file for complete search history.

(56) References Cited

U.S. PATENT DOCUMENTS 2,842,476 A   7/1958  Schreiber et al.
4,091,006 A   5/1978  Durden et al.
(Continued)

FOREIGN PATENT DOCUMENTS

DE   2361084 A1   6/1974
EP   0036106 A2   9/1981
(Continued)

OTHER PUBLICATIONS

International Search Report for PCT/EP2011/069040 Mailed Apr. 25, 2012.

*Primary Examiner* — Johann R Richter
*Assistant Examiner* — Yanzhi Zhang
(74) *Attorney, Agent, or Firm* — Miles & Stockbridge PC

(57) ABSTRACT

The invention relates to novel compounds of the formula (I)

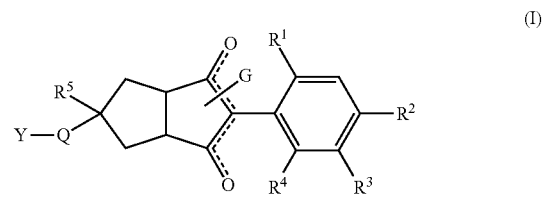

(I)

in which $R^1$, $R^2$, $R^3$, $R^4$, $R^5$, Y, Q and G have the meanings given above,
to a plurality of processes and intermediates for their preparation and to their use as herbicides and/or pesticides.
Moreover, the invention relates to selective herbicidal compositions comprising, firstly, the phenyl-substituted bicyclooctane-1,3-dione derivates and, secondly, a crop plant compatibility-improving compound.
The present invention furthermore relates to increasing the activity of crop protection compositions comprising in particular phenyl-substituted bicyclooctane-1,3-dione derivates by adding ammonium salts or phosphonium salts and, if appropriate, penetrants, to the corresponding compositions, to processes for their preparation and to their use in crop protection as pesticides and/or for preventing unwanted plant growth.

14 Claims, No Drawings

(51) Int. Cl.

| | | |
|---|---|---|
| A01N 35/10 | (2006.01) | |
| A01N 37/08 | (2006.01) | |
| A01N 37/34 | (2006.01) | |
| A01N 43/26 | (2006.01) | |
| A01N 43/32 | (2006.01) | |
| C07C 45/51 | (2006.01) | |
| C07C 49/67 | (2006.01) | |
| C07C 49/753 | (2006.01) | |
| C07C 49/757 | (2006.01) | |
| C07C 67/14 | (2006.01) | |
| C07C 67/29 | (2006.01) | |
| C07C 67/313 | (2006.01) | |
| C07C 68/02 | (2006.01) | |
| C07C 69/007 | (2006.01) | |
| C07C 69/013 | (2006.01) | |
| C07C 69/157 | (2006.01) | |
| C07C 69/24 | (2006.01) | |
| C07C 69/30 | (2006.01) | |
| C07C 69/738 | (2006.01) | |
| C07C 69/757 | (2006.01) | |
| C07C 69/96 | (2006.01) | |
| C07C 233/58 | (2006.01) | |
| C07C 251/40 | (2006.01) | |
| C07C 251/42 | (2006.01) | |
| C07C 251/52 | (2006.01) | |
| C07C 255/40 | (2006.01) | |
| C07C 255/47 | (2006.01) | |
| C07C 271/10 | (2006.01) | |
| C07C 271/28 | (2006.01) | |
| C07C 317/24 | (2006.01) | |
| C07C 323/22 | (2006.01) | |
| C07C 327/28 | (2006.01) | |
| C07C 331/06 | (2006.01) | |
| C07C 331/10 | (2006.01) | |
| C07C 333/08 | (2006.01) | |
| C07D 207/46 | (2006.01) | |
| C07D 263/46 | (2006.01) | |
| C07D 263/58 | (2006.01) | |
| C07D 277/34 | (2006.01) | |
| C07D 295/192 | (2006.01) | |
| C07D 307/18 | (2006.01) | |
| C07D 309/12 | (2006.01) | |
| C07D 317/12 | (2006.01) | |
| C07D 319/06 | (2006.01) | |
| C07D 321/06 | (2006.01) | |
| C07D 327/06 | (2006.01) | |
| C07D 339/06 | (2006.01) | |
| C07D 339/08 | (2006.01) | |
| C07F 9/655 | (2006.01) | |
| A01N 43/30 | (2006.01) | |
| A01N 43/36 | (2006.01) | |
| A01N 43/80 | (2006.01) | |
| A01N 43/84 | (2006.01) | |
| A01N 43/86 | (2006.01) | |
| A01N 47/18 | (2006.01) | |
| A01N 43/28 | (2006.01) | |
| A01N 43/78 | (2006.01) | |

(52) U.S. Cl.
CPC .......... *C07C 271/28* (2013.01); *C07C 317/24* (2013.01); *C07C 323/22* (2013.01); *C07C 327/28* (2013.01); *C07C 331/06* (2013.01); *C07C 331/10* (2013.01); *C07C 333/08* (2013.01); *C07D 207/46* (2013.01); *C07D 263/46* (2013.01); *C07D 263/58* (2013.01); *C07D 277/34* (2013.01); *C07D 295/192* (2013.01); *C07D 307/18* (2013.01); *C07D 309/12* (2013.01); *C07D 317/12* (2013.01); *C07D 319/06* (2013.01); *C07D 321/06* (2013.01); *C07D 327/06* (2013.01); *C07D 339/06* (2013.01); *C07D 339/08* (2013.01); *C07F 9/65515* (2013.01); *C07C 2102/22* (2013.01)

(56) References Cited

U.S. PATENT DOCUMENTS

| | | |
|---|---|---|
| 4,283,348 A | 8/1981 | Wheeler |
| 4,338,122 A | 7/1982 | Wheeler |
| 4,436,666 A | 3/1984 | Wheeler |
| 4,526,723 A | 7/1985 | Wheeler et al. |
| 4,551,547 A | 11/1985 | Wheeler |
| 4,632,698 A | 12/1986 | Wheeler |
| 4,844,734 A | 7/1989 | Iwasaki et al. |
| 5,013,659 A | 5/1991 | Bedbrook et al. |
| 5,462,912 A | 10/1995 | Hioki et al. |
| 5,500,367 A | 3/1996 | Hain et al. |
| 5,538,937 A | 7/1996 | Hasebe et al. |
| 5,705,476 A | 1/1998 | Hoffarth |
| 5,808,135 A | 9/1998 | Fischer et al. |
| 5,840,661 A | 11/1998 | Fischer et al. |
| 5,985,647 A | 11/1999 | Schroder et al. |
| 6,150,304 A | 11/2000 | Fischer et al. |
| 6,251,833 B1 | 6/2001 | Erdelen et al. |
| 6,417,370 B1 | 7/2002 | Lieb et al. |
| 6,451,843 B1 | 9/2002 | Lieb et al. |
| 6,458,965 B1 | 10/2002 | Lieb et al. |
| 6,569,810 B1 | 5/2003 | Fischer et al. |
| 6,602,823 B1 | 8/2003 | Rochling et al. |
| 6,645,914 B1 | 11/2003 | Woznica et al. |
| 6,693,092 B2 | 2/2004 | Drewes et al. |
| 6,716,832 B2 | 4/2004 | Lieb et al. |
| 6,806,264 B2 | 10/2004 | Lieb et al. |
| 7,105,471 B2 | 9/2006 | Lieb et al. |
| 7,288,676 B2 | 10/2007 | Lieb et al. |
| 7,718,706 B2 | 5/2010 | Lieb et al. |
| 7,776,791 B2 | 8/2010 | Fischer et al. |
| 7,888,285 B2 | 2/2011 | Fischer et al. |
| 7,915,282 B2 | 3/2011 | Ruther et al. |
| 7,947,704 B2 | 5/2011 | Bretschneider et al. |
| 8,013,172 B2 | 9/2011 | Fischer et al. |
| 8,058,210 B2 | 11/2011 | Lieb et al. |
| 8,168,832 B2 | 5/2012 | Fischer et al. |
| 8,193,120 B2 | 6/2012 | Ruther et al. |
| 8,334,300 B2 | 12/2012 | Ruther et al. |
| 2002/0188136 A1 | 12/2002 | Lieb et al. |
| 2003/0073851 A1 | 4/2003 | Lieb et al. |
| 2003/0096806 A1 | 5/2003 | Lieb et al. |
| 2003/0216260 A1 | 11/2003 | Ruther et al. |
| 2003/0224939 A1 | 12/2003 | Miles |
| 2004/0127365 A1 | 7/2004 | Lieb et al. |
| 2004/0167031 A1 | 8/2004 | Lieb et al. |
| 2004/0224844 A1 | 11/2004 | Bickers et al. |
| 2005/0009880 A1 | 1/2005 | Cottrell et al. |
| 2005/0037922 A1 | 2/2005 | Bickers et al. |
| 2005/0049145 A1 | 3/2005 | Bickers et al. |
| 2005/0096386 A1 | 5/2005 | Cottrell et al. |
| 2005/0256000 A1 | 11/2005 | Schaper et al. |
| 2006/0122061 A1 | 6/2006 | Lieb et al. |
| 2006/0166829 A1 | 7/2006 | Fischer et al. |
| 2007/0015664 A1 | 1/2007 | Fischer et al. |
| 2007/0298968 A1 | 12/2007 | Bretschneider et al. |
| 2008/0081807 A1 | 4/2008 | Lieb et al. |
| 2008/0269052 A1 | 10/2008 | Rosinger et al. |
| 2008/0269059 A1 | 10/2008 | Ziemer et al. |
| 2009/0137393 A1 | 5/2009 | Fischer et al. |
| 2009/0209513 A1 | 8/2009 | Fischer et al. |
| 2009/0227563 A1 | 9/2009 | Fischer et al. |
| 2009/0305891 A1 | 12/2009 | Fischer et al. |
| 2010/0009850 A1 | 1/2010 | Fischer et al. |
| 2010/0087320 A1 | 4/2010 | Lieb et al. |

(56) References Cited

U.S. PATENT DOCUMENTS

| | | |
|---|---|---|
| 2010/0267964 A1 | 10/2010 | Fischer et al. |
| 2011/0039701 A1* | 2/2011 | Angermann et al. ......... 504/136 |
| 2011/0084230 A1 | 4/2011 | Knochel et al. |
| 2011/0092368 A1 | 4/2011 | Fischer et al. |
| 2011/0143943 A1 | 6/2011 | Ruther et al. |
| 2011/0183849 A1 | 7/2011 | Ruther et al. |
| 2011/0195842 A1 | 8/2011 | Bretschneider et al. |
| 2011/0213160 A1 | 9/2011 | Bretschneider et al. |
| 2012/0178927 A1 | 7/2012 | Fischer et al. |
| 2012/0238450 A1 | 9/2012 | Ruther et al. |

FOREIGN PATENT DOCUMENTS

| | | |
|---|---|---|
| EP | 0086750 A2 | 8/1983 |
| EP | 0094349 A2 | 11/1983 |
| EP | 0131624 A1 | 1/1985 |
| EP | 0142924 A2 | 5/1985 |
| EP | 0174562 A2 | 3/1986 |
| EP | 191736 A2 | 8/1986 |
| EP | 0193259 A1 | 9/1986 |
| EP | 0221044 A1 | 5/1987 |
| EP | 0242236 A1 | 10/1987 |
| EP | 0242246 A1 | 10/1987 |
| EP | 0257993 A2 | 3/1988 |
| EP | 0268554 A2 | 5/1988 |
| EP | 0309862 A1 | 4/1989 |
| EP | 333131 A1 | 9/1989 |
| EP | 0346620 A1 | 12/1989 |
| EP | 365484 A1 | 4/1990 |
| EP | 0453086 A2 | 10/1991 |
| EP | 0464461 A2 | 1/1992 |
| EP | 0492366 A2 | 7/1992 |
| EP | 0582198 A2 | 2/1994 |
| EP | 0664081 A2 | 7/1995 |
| EP | 0681865 A2 | 11/1995 |
| EP | 0305398 A1 | 12/2003 |
| FR | 2600494 A1 | 12/1987 |
| JP | 60087254 A1 | 5/1985 |
| WO | 99/00020 | 1/1991 |
| WO | 91/07874 | 6/1991 |
| WO | 91/08202 | 6/1991 |
| WO | 91/13972 | 9/1991 |
| WO | 91/19806 | 12/1991 |
| WO | 92/00377 | 1/1992 |
| WO | 92/11376 | 7/1992 |
| WO | 92/14827 | 9/1992 |
| WO | 92/16108 | 10/1992 |
| WO | 95/07897 | 3/1995 |
| WO | 9601798 A1 | 1/1996 |
| WO | 9603366 A1 | 2/1996 |
| WO | 9714667 A1 | 4/1997 |
| WO | 97/45016 | 12/1997 |
| WO | 98/13361 | 4/1998 |
| WO | 98/27049 | 6/1998 |
| WO | 98/35553 | 8/1998 |
| WO | 98/38856 | 9/1998 |
| WO | 9839281 A1 | 9/1998 |
| WO | 99/16744 | 4/1999 |
| WO | 9943649 A1 | 9/1999 |
| WO | 9948869 A1 | 9/1999 |
| WO | 9955673 A1 | 11/1999 |
| WO | 0035278 A1 | 6/2000 |
| WO | 0117972 A2 | 3/2001 |
| WO | 0174770 A1 | 10/2001 |
| WO | 0234048 A1 | 5/2002 |
| WO | 03062244 A1 | 7/2003 |
| WO | 2004/084631 A1 | 7/2004 |
| WO | 2004080962 A1 | 9/2004 |
| WO | 2004111042 A1 | 12/2004 |
| WO | 2005/015994 A1 | 2/2005 |
| WO | 2005/016001 A1 | 2/2005 |
| WO | 2005092897 A2 | 10/2005 |
| WO | 2005/112630 A1 | 12/2005 |
| WO | 2006029799 A1 | 3/2006 |
| WO | 2007/023719 A1 | 3/2007 |
| WO | 2007/023764 A1 | 3/2007 |
| WO | 2007/068427 A2 | 6/2007 |
| WO | 2007/068428 A2 | 6/2007 |
| WO | 2007080066 A2 | 7/2007 |
| WO | 2007096058 A1 | 8/2007 |
| WO | 2007/113294 A1 | 10/2007 |
| WO | 2008/131860 A2 | 11/2008 |
| WO | 2009019005 A2 | 2/2009 |
| WO | 2009019015 A1 | 2/2009 |
| WO | 2010000773 A1 | 1/2010 |
| WO | 2010040460 A2 | 4/2010 |
| WO | WO 2010040460 * | 4/2010 ............ A01N 35/06 |
| WO | 2010081894 A1 | 7/2010 |
| WO | 2010089210 A1 | 8/2010 |

* cited by examiner

PHENYL-SUBSTITUTED BICYCLOOCTANE-1,3-DIONE-DERIVATIVES

CROSS REFERENCE TO RELATED APPLICATIONS

This application is a §371 National Stage Application of PCT/EP2011/069040, filed Oct. 28, 2011, which claims priority to European Application No. 10189670.2, filed Nov. 2, 2010, and U.S. Provisional Application filed Nov. 2, 2010.

BACKGROUND OF THE INVENTION

1. Field of the Invention

The present invention relates to novel phenyl-substituted bicyclooctane-1,3-dione derivatives, to a plurality of processes for their preparation and to their use as herbicides and/or pesticides.

2. Description of Related Art

Moreover, the invention relates to novel selective herbicidal active compound combinations comprising, firstly, phenyl-substituted bicyclooctane-1,3-dione derivates and, secondly, at least one crop plant compatibility-improving compound, which combinations can be used with particularly good results for the selective control of weeds and various crops of useful plants.

The present invention furthermore relates to increasing the activity of crop protection compositions comprising in particular phenyl-substituted bicyclooctane-1,3-dione derivates by adding ammonium salts or phosphonium salts and, if appropriate, penetrants, to the corresponding compositions, to processes for their preparation and to their use in crop protection as insecticides and/or for preventing unwanted plant growth.

It is known that certain substituted 2-arylcyclopentanediones have herbicidal, insecticidal and acaricidal properties (cf., for example, U.S. Pat. Nos. 4,283,348; 4,338,122; 4,436,666; 4,526,723; 4,551,547; 4,632,698; WO 96/01 798; WO 96/03 366, WO 97/14 667 and also WO 98/39281, WO 99/43649, WO99/48869, WO 99/55673, WO 01/17972, WO 01/74770, WO 03/062244, WO 04/080962, WO04/111042, WO05/092897, WO06/029799, WO07/080,066, WO07/096,058, WO 09/019,005, WO 09/019,015, WO 10/000,773, WO 10/081,894, WO 10/089,210 and WO 10/040,460). Also known are compounds which are substituted in a similar way: 3-hydroxy-5,5-dimethyl-2-phenylcyclopent-2-en-1-one from the publication Micklefield et. al., Tetrahedron, (1992), 7519-26 and the natural product Involution (–)-cis-5-(3,4-dihydroxyphenyl)-3,4-dihydroxy-2-(4-hydroxyphenyl)-cyclopent-2-enone from the publication Edwards et al., J. Chem. Soc. S, (1967), 405-9. An insecticidal or acaricidal action is not described. Moreover, 2-(2,4,6-trimethylphenyl)-1,3-indanedione is known from the publication J. Economic Entomology, 66 (1973), 584 and the laid-open publication DE-A 2 361 084 (U.S. Pat. No. 4,091,006), with herbicidal and acaricidal actions being stated.

However, in particular at low application rates and concentrations, the activity and activity spectrum of these compounds is not always fully satisfactory. Furthermore, the compatibility of these compounds with plants is not always sufficient.

SUMMARY

This invention now provides novel compounds of the formula (I)

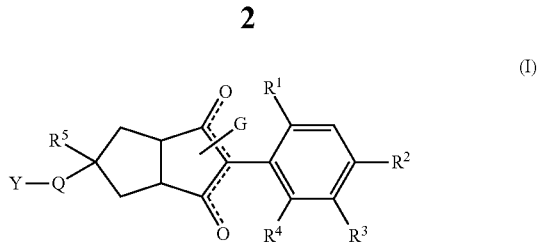

in which
if
Q represents a bond, a $C_1$-$C_3$-alkylene, a $C_2$-$C_3$-alkenylene or a $C_2$-$C_3$-alkynylene chain,
then
Y represents the groups —$OR^6$, —$S(O)_pR^6$, —$CO_2R^7$, —$CH=CH_2$, cyano, —SCN, —$CONR^8R^9$, —$SO_2NR^8R^9$, $CR^{10}$=O, —$NR^{11}R^{12}$, —$CR^{10}$=N—$OR^{13}$, —$CR^{10}$=N—$R^{14}$, $CR^{10}$=N—$NR^{15}R^{16}$, —$CR^{10}$($OR^{17}OR^{18}$), —$CR^{10}$($SR^{17}OR^{18}$), —$CR^{10}$($SR^{17}SR^{18}$), —$CR^{10}$($NHR^{17}NHR^{18}$), —$CR^{10}$($NHR^{17}OR^{18}$), —$CR^{10}$($NHR^{17}SR^{18}$), —$CH(CN)_2$, —$CH(OH)R^6$, halogen, —$O(C=M)R^{10}$, —$S(C=M)R^{10}$, —$O(C=M)NR^{11}R^{12}$, —$S(C=M)NR^{11}R^{12}$, —$NH(C=M)NR^{11}R^{12}$, —$O(C=M)OR^7$, —$S(C=M)OR^7$, —$NH(C=M)OR^7$ or represents the group W,
or Q, Y and $R^5$ together form one of the groups CHCN=, CH($CO_2C_1$-$C_6$-alkyl)=,

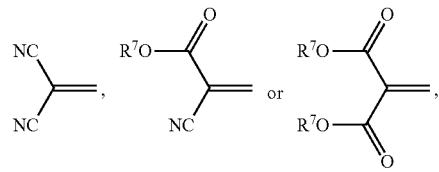

W represents a 3- to 7-membered saturated or partially saturated heterocycle which contains at least one heteroatom such as oxygen, sulphur or nitrogen and may additionally be mono- or polysubstituted by identical or different substituents,
G represents hydrogen, methyl, ethyl or benzyl (a) or represents one of the groups

E or

E represents a metal ion equivalent, a tertiary sulphonium ion or an ammonium ion, L represents oxygen or sulphur, M represents oxygen or sulphur, $R^1$ represents hydrogen, halogen, cyano, nitro, $C_1$-$C_6$-alkyl, halo-$C_1$-$C_6$-alkyl, $C_3$-$C_6$-cycloalkyl, halo-$C_3$-$C_6$-cycloalkyl, $C_2$-$C_6$-alkenyl, halo-$C_2$-$C_6$-alkenyl, $C_2$-$C_6$-alkynyl, halo-$C_2$-$C_6$-alkynyl, $C_1$-$C_6$-alkoxy, halo-$C_1$-$C_6$-alkoxy, $C_3$-$C_6$-cycloalkoxy, halo-$C_3$-$C_6$-cycloalkoxy, $C_2$-$C_6$-alkynyloxy, halo-$C_2$-$C_6$-alkynyloxy, $C_2$-$C_6$-alkenyloxy, halo-$C_2$-$C_6$-alkenyloxy, $C_1$-$C_3$-alkylthio, $C_1$-$C_3$-alkylsulphinyl, $C_1$-$C_3$-alkylsulphonyl, halo-$C_1$-$C_3$-alkylthio, halo-$C_1$-$C_3$-alkylsulphinyl or halo-$C_1$-$C_3$-alkylsulphonyl, $R^2$ and $R^3$ independently of one another are identical or different and represent hydrogen, halogen, cyano, nitro, $C_1$-$C_6$-alkyl, halo-$C_1$-$C_6$-alkyl, $C_2$-$C_6$-alkenyl, halo-$C_2$-$C_6$-alkenyl, $C_2$-$C_6$-alkynyl, halo-$C_2$-$C_6$-alkynyl, $C_1$-$C_6$-alkoxy, halo-$C_1$-$C_6$-alkoxy, $C_3$-$C_6$-cycloalkoxy, halo-$C_3$-$C_6$-cycloalkoxy, $C_2$-$C_6$-alkynyloxy, halo-$C_2$-$C_6$-alkynyloxy, $C_2$-$C_6$-alkenyloxy, halo-$C_2$-$C_6$-alkenyloxy, $C_1$-$C_3$-alkylthio, $C_1$-$C_3$-alkylsulphinyl, $C_1$-$C_3$-alkylsulphonyl, halo-$C_1$-$C_3$-alkylthio, halo-$C_1$-$C_3$-alkylsulphinyl, halo-$C_1$-$C_3$-alkylsulphonyl, phenyl or phenyl which is optionally mono- or polysubstituted by identical or different substituents from the group consisting of halogen, $C_1$-$C_4$-alkyl, halo-$C_1$-$C_4$-alkyl, $C_3$-$C_6$-cycloalkyl, halo-$C_3$-$C_6$-cycloalkyl, $C_1$-$C_6$-alkoxy, halo-$C_1$-$C_6$-alkoxy, nitro and cyano, $R^4$ represents hydrogen, halogen, cyano, nitro, $C_1$-$C_6$-alkyl, halo-$C_1$-$C_6$-alkyl, $C_3$-$C_6$-cycloalkyl, halo-$C_3$-$C_6$-cycloalkyl, $C_1$-$C_6$-alkoxy, halo-$C_1$-$C_6$-alkoxy, $C_3$-$C_6$-cycloalkoxy, or halo-$C_3$-$C_6$-cycloalkoxy, $R^5$ represents hydrogen or $C_1$-$C_4$-alkyl, $R^6$ represents hydrogen, $C_1$-$C_6$-alkyl, halo-$C_1$-$C_6$-alkyl, $C_3$-$C_6$-cycloalkyl, halo-$C_3$-$C_6$-cycloalkyl, $C_2$-$C_6$-alkenyl, halo-$C_2$-$C_6$-alkenyl, $C_2$-$C_6$-alkynyl, halo-$C_2$-$C_6$-alkynyl, $C_1$-$C_4$-alkoxy-$C_1$-$C_4$-alkyl, halo-$C_1$-$C_4$-alkoxy-$C_1$-$C_4$-alkyl, $C_3$-$C_6$-cycloalkoxy-$C_1$-$C_4$-alkyl, halo-$C_3$-$C_4$-cycloalkoxy-$C_1$-$C_4$-alkyl, represents benzyl, phenyl, heteroaryl, —$CH_2$-heteroaryl, —$CH_2CH_2$-heteroaryl, pyranyl, tetrahydrofuranyl, $C_1$-$C_4$-alkanoyl, halo-$C_1$-$C_4$-alkanoyl, benzoyl, each of which is optionally mono- or polysubstituted by identical or different substituents from the group consisting of halogen, cyano, nitro, $C_1$-$C_6$-alkyl, halo-$C_1$-$C_6$-alkyl, $C_3$-$C_6$-cycloalkyl, halo-$C_3$-$C_6$-cycloalkyl, $C_2$-$C_6$-alkenyl, $C_2$-$C_6$-alkynyl, halo-$C_2$-$C_6$-alkynyl, $C_1$-$C_4$-alkoxyalkyl, halo-$C_1$-$C_4$-alkoxy-$C_1$-$C_6$-alkyl, $C_3$-$C_6$-cycloalkoxy-$C_1$-$C_6$-alkyl and halo-$C_3$-$C_6$-cycloalkoxy-$C_1$-$C_6$-alkyl, or represents benzoyl, which is optionally mono- or polysubstituted by identical or different substituents from the group consisting of halogen, cyano, nitro, $C_1$-$C_6$-alkyl, halo-$C_1$-$C_6$-alkyl, $C_3$-$C_6$-cycloalkyl and halo-$C_3$-$C_6$-cycloalkyl, $R^7$ represents hydrogen, represents in each case optionally substituted $C_1$-$C_6$-alkyl, $C_3$-$C_6$-cycloalkyl, $C_2$-$C_6$-alkenyl or represents a cation E, $R^8$ and $R^9$ independently of one another are identical or different and represent hydrogen, $C_1$-$C_6$-alkyl, $C_2$-$C_6$-alkenyl, $C_2$-$C_6$-alkynyl, $C_3$-$C_6$-cycloalkyl, phenyl, benzyl, represent phenyl or benzyl, each of which is mono- or polysubstituted by identical or different substituents from the group consisting of halogen, nitro, cyano and $C_1$-$C_3$-alkyl or $R^8$ and $R^9$ together with the adjacent nitrogen atom form a morpholino, piperidino or pyrrolidino group, $R^{10}$ represents hydrogen, $C_1$-$C_6$-alkyl, halo-$C_1$-$C_4$ alkyl, $C_2$-$C_6$-alkenyl, halo-$C_2$-$C_6$-alkenyl, $C_2$-$C_6$-alkynyl, $C_3$-$C_6$-cycloalkyl, represents phenyl or benzyl, each of which is optionally mono- or polysubstituted by identical or different substituents from the group consisting of halogen, $C_1$-$C_6$-alkyl and halo-$C_1$-$C_6$-alkyl, $R^{11}$ and $R^{12}$ independently of one another are identical or different and represent hydrogen, $C_1$-$C_6$-alkyl, $C_2$-$C_6$-alkenyl, $C_2$-$C_6$-alkynyl, $C_3$-$C_6$-cycloalkyl, phenyl, benzyl, represent phenyl or benzyl, each of which is mono- or polysubstituted by identical or different substituents from the group consisting of halogen, nitro, cyano and $C_1$-$C_3$-alkyl or $R^{11}$ and $R^{12}$ together with the adjacent nitrogen atom form a morpholino, piperidino or pyrrolidino group, $R^{13}$ represents hydrogen or represents $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_3$-alkyl, each of which is optionally interrupted once or more by oxygen or sulphur and is optionally mono- or polysubstituted by halogen, represents benzyl or —$CH_2$-heterocyclyl, each of which is optionally mono- or polysubstituted by identical or different substituents from the group consisting of halogen, nitro, cyano and $C_1$-$C_3$-alkyl, $R^{14}$ represents hydrogen, $C_1$-$C_6$-alkyl, halo-$C_1$-$C_6$-alkyl, $C_2$-$C_6$-alkenyl, halo-$C_2$-$C_6$-alkenyl, $C_2$-$C_6$-alkynyl, halo-$C_2$-$C_6$-alkynyl, phenyl, benzyl or represents phenyl or benzyl, each of which is mono- or polysubstituted by identical or different substituents from the group consisting of halogen, $C_1$-$C_3$-alkyl, halo-$C_1$-$C_3$-alkyl, $C_3$-$C_6$-cycloalkyl, halo-$C_3$-$C_6$-cycloalkyl, nitro and cyano, $R^{15}$ and $R^{16}$ independently of one another are identical or different and represent hydrogen, $C_1$-$C_5$-alkyl, $C_2$-$C_6$-alkenyl, $C_2$-$C_6$-alkynyl, $C_3$-$C_6$-cycloalkyl, phenyl, benzyl, represent phenyl or benzyl, each of which is mono- or polysubstituted by identical or different substituents from the group consisting of halogen, nitro, cyano and $C_1$-$C_3$-alkyl or $R^{15}$ and $R^{16}$ together with the adjacent nitrogen atom form a morpholino, piperidino or pyrrolidino group, $R^{17}$ represents hydrogen, represents $C_1$-$C_6$-alkyl, benzyl or halo-$C_1$-$C_6$-alkyl, each of which is optionally interrupted once or more by identical or different radicals from the group consisting of oxygen and sulphur, $R^{18}$ represents hydrogen, represents $C_1$-$C_6$-alkyl, benzyl or halo-$C_1$-$C_6$-alkyl, each of which is optionally interrupted once or more by identical or different radicals from the group consisting of oxygen and sulphur, $R^{19}$ represents optionally halogen-substituted $C_1$-$C_6$-alkyl, $C_2$-$C_6$-alkenyl, $C_1$-$C_4$-alkoxy-$C_1$-$C_4$-alkyl, $C_1$-$C_3$-alkylthio-$C_1$-$C_4$-alkyl, poly-$C_1$-$C_4$-alkoxy-$C_1$-$C_4$-alkyl or represents $C_3$-$C_6$-cycloalkyl which is optionally mono- or polysubstituted by identical or different substituents from the group consisting of halogen, $C_1$-$C_4$-alkyl and $C_1$-$C_4$-alkoxy and may optionally be interrupted in the ring by oxygen or sulphur, represents phenyl, phenyl-$C_1$-$C_4$-alkyl, hetaryl, phenoxy-$C_1$-$C_4$-alkyl or hetaryloxy-$C_1$-$C_4$-alkyl, each of which is optionally substituted by halogen or $C_1$-$C_4$-alkyl, $R^{20}$ represents $C_1$-$C_6$-alkyl, $C_2$-$C_6$-alkenyl, $C_1$-$C_4$-alkoxy-$C_1$-$C_4$-alkyl, poly-$C_1$-$C_4$-alkoxy-$C_1$-$C_4$-alkyl, each of which is optionally mono- or polysubstituted by identical or different halogen, or represents $C_3$-$C_6$-cycloalkyl which may optionally be interrupted in the ring by oxygen or sulphur, or represents benzyl, $R^{21}$, $R^{22}$ and $R^{23}$ independently of one another are identical or different and represent $C_1$-$C_6$-alkyl, $C_1$-$C_6$-alkoxy, $C_1$-$C_6$-alkylamino, $C_1$-$C_6$-dialkylamino, $C_1$-$C_3$-alkylthio, $C_2$-$C_4$-alkenylthio, $C_3$-$C_6$-cycloalkylthio, each of which is optionally mono- or polysubstituted by identical or different halogen, or represent phenyl, benzyl, phenoxy or phenylthio, $R^{24}$ and $R^{25}$ independently of one another are identical or different and represent hydrogen, represent $C_1$-$C_6$-alkyl, $C_3$-$C_6$-cycloalkyl, $C_2$-$C_6$-alkenyl, $C_1$-$C_6$-alkoxy, $C_1$-$C_6$-alkoxy-$C_1$-$C_4$-alkyl, each of which is optionally mono- or polysubstituted by identical or different halogen, represent phenyl or benzyl, optionally mono- or polysubstituted by identical or different substituents from the group consisting of halogen and $C_1$-$C_4$-alkyl or $R^{24}$ and $R^{25}$ together with the adjacent nitrogen atom form a morpholino, piperidino or pyrrolidino group, p represents the number 0, 1 or 2, or if Q, Y and $R^5$ together represent the group $CH_2$=, then G represents methyl, ethyl or benzyl (a).

Substituent G may be attached according to formula (I-A), (I-B) or (I-C).

DETAILED DESCRIPTION OF A PREFERRED EMBODIMENT

In this context, the term "halogen" comprises fluorine, chlorine, bromine and iodine.

The terms "alkyl", "alkenyl" and "alkynyl" are to be understood as meaning both straight-chain and branched hydrocarbon radicals.

Depending inter alia on the nature of the substituents, the compounds of the formula (I) may be present as geometric and/or optical isomers or isomer mixtures of varying composition which, if appropriate, may be separated in a customary manner. The present invention provides both the pure isomers and the isomer mixtures, their preparation and use and compositions comprising them. However, for the sake of simplicity, hereinbelow only compounds of the formula (I) are referred to, although what is meant is both the pure compounds and, if appropriate, mixtures having various proportions of isomeric compounds.

Depending on the position of the substituent G, the compounds of the formula (I) can be present in the two isomeric forms of the formulae (I-A) and (I-B)

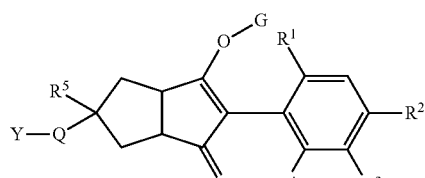

(I-A)

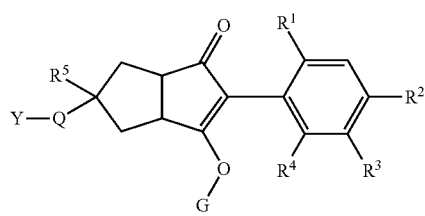

(I-B)

which is meant to be indicated by the broken line in formula (I).

For the specific case in which the substituent G in the formula (I) is hydrogen, an additional isomeric form may also be present having the formula (I-C)

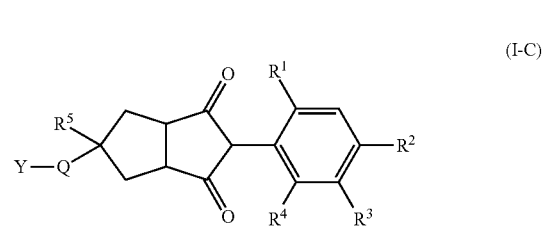

(I-C)

The compounds of the formulae (I-A), (I-B) and (I-C) can be present both as mixtures and in the form of their pure isomers. If appropriate, mixtures of the compounds of the formulae (I-A), (I-B) and (I-C) can be separated by physical methods, for example by way of chromatographic methods.

For reasons of clarity, hereinbelow only one of the possible isomers is shown in each case. This does not exclude that, if appropriate, the compounds may be present in the form of the isomer mixtures or in the respective other isomeric form.

For reasons of simplicity, in the case of the compounds of the formula (I-a), in most cases only the isomeric form (I-C), in which G represents hydrogen, is shown. However, in the compounds of the formula (I-a), the G substituent may also represent methyl, ethyl or benzyl, in which case the compounds are present in the isomeric forms (I-A) and (I-B).

Including the different meanings (a), (b), (c), (d), (e), (f) and (g) of group G, the following principle structures (I-a) to (I-g) result:

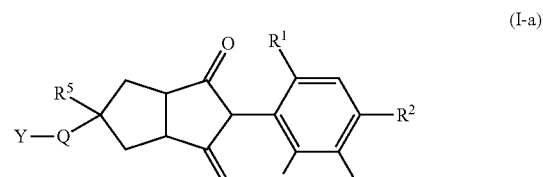

(I-a)

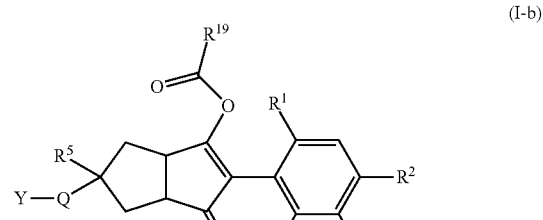

(I-b)

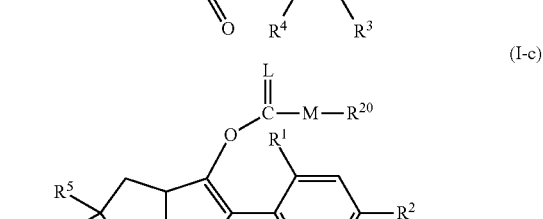

(I-c)

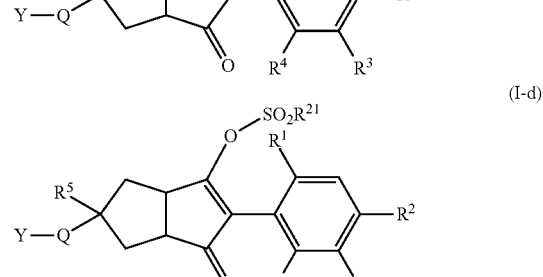

(I-d)

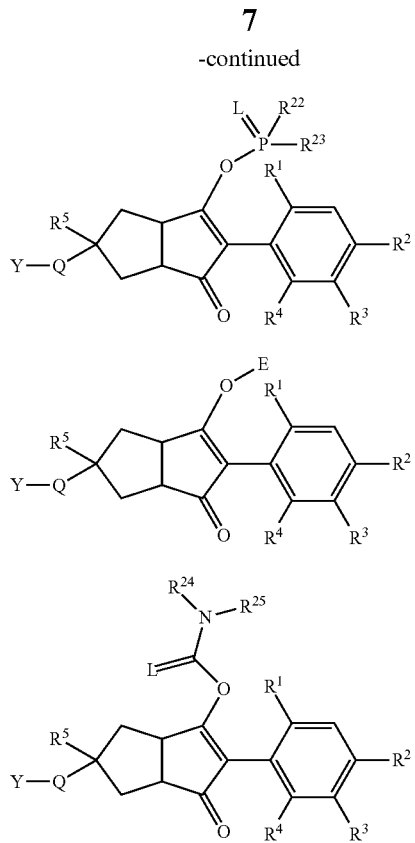
(I-e)
(I-f)
(I-g)

in which

Q, Y, E, L, M, R$^1$, R$^2$, R$^3$, R$^4$, R$^5$, R$^{19}$, R$^{20}$, R$^{21}$, R$^{22}$, R$^{23}$, R$^{24}$ and R$^{25}$ have the meanings given above.

A further form of stereoisomerism results from the cis-attachment of the two carbacyclic five-membered rings. Depending on the spatial arrangement of the grouping Q-Y or R$^5$, two different spatial isomers are formed.

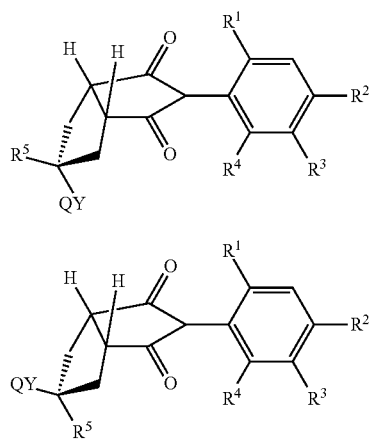

syn-(Ia)

anti-(Ia)

Hereinbelow, these isomers are referred to as "syn" and "anti", respectively, depending on whether the grouping Q-Y in the compounds according to the invention is in the anti- or syn-position to the cyclopentanedione ring. For example, if R$^5$ is hydrogen, Q is a —CH$_2$— group, Y is —CO$_2$CH$_3$ and R$^1$, R$^2$, R$^3$ and R$^4$ have the meaning given in the formula (I-a), syn- and anti-isomers are defined as follows:

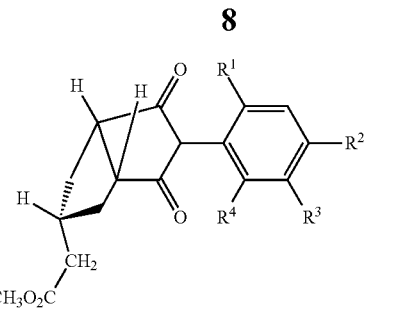

syn-isomer

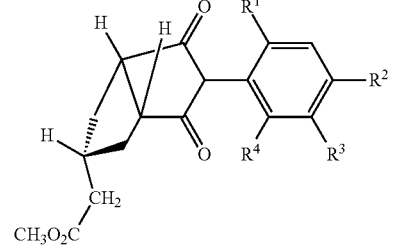

anti-isomer

Furthermore, it has been found that the novel compounds of the formula (I) are obtained by one of the processes described below:

(A) Compounds of the formula (I-a)

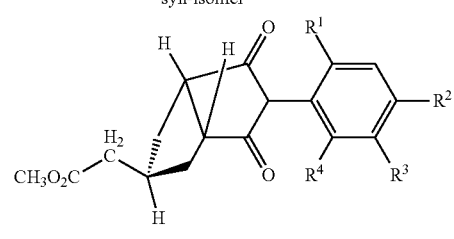

(I-a)

in which
Q, Y, R$^1$, R$^2$, R$^3$, R$^4$ and R$^5$ have the meaning given above are obtained when
ketocarboxylic esters of the formula (II)

(II)

in which
Q, Y, R$^1$, R$^2$, R$^3$, R$^4$ and R$^5$ have the meaning given above and
R$^{26}$ represents alkyl (in particular C$_1$-C$_8$-alkyl)
are cyclized intramolecularly, if appropriate in the presence of a diluent in the presence of a base.

Compounds of the formula (I-a) are furthermore obtained by further functionalization of compounds which are already known, for example the synthesis examples I-a-4 and I-a-5 from WO2010/040460, the preparation of which is known from the literature.

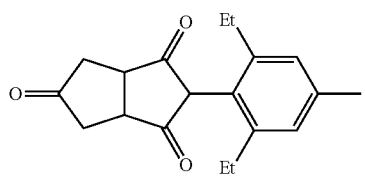

Example I-a-4
from WO 2010/040060

-continued

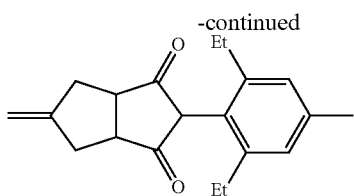

Example I-a-5
from WO 2010/040060

The synthetic transformation of these substances and analogous substances into the compounds of the formula (I) according to the invention can be carried out by known standard processes of organic chemistry familiar to the person skilled in the art, for example hydroboration, alkylation, acylation, oxidation, reduction, acetalization, condensation, Wittig reaction, Grignard or organometal addition, halogenation or nucleophilic substitution reactions. Some of these processes are outlined in an exemplary manner in schemes 1 and 2. Further details can additionally also be found in the preparation examples shown.

If the substituent G represents methyl, ethyl or benzyl, the substituent G is introduced by alkylation or benzylation starting with the compound in which G represents hydrogen.

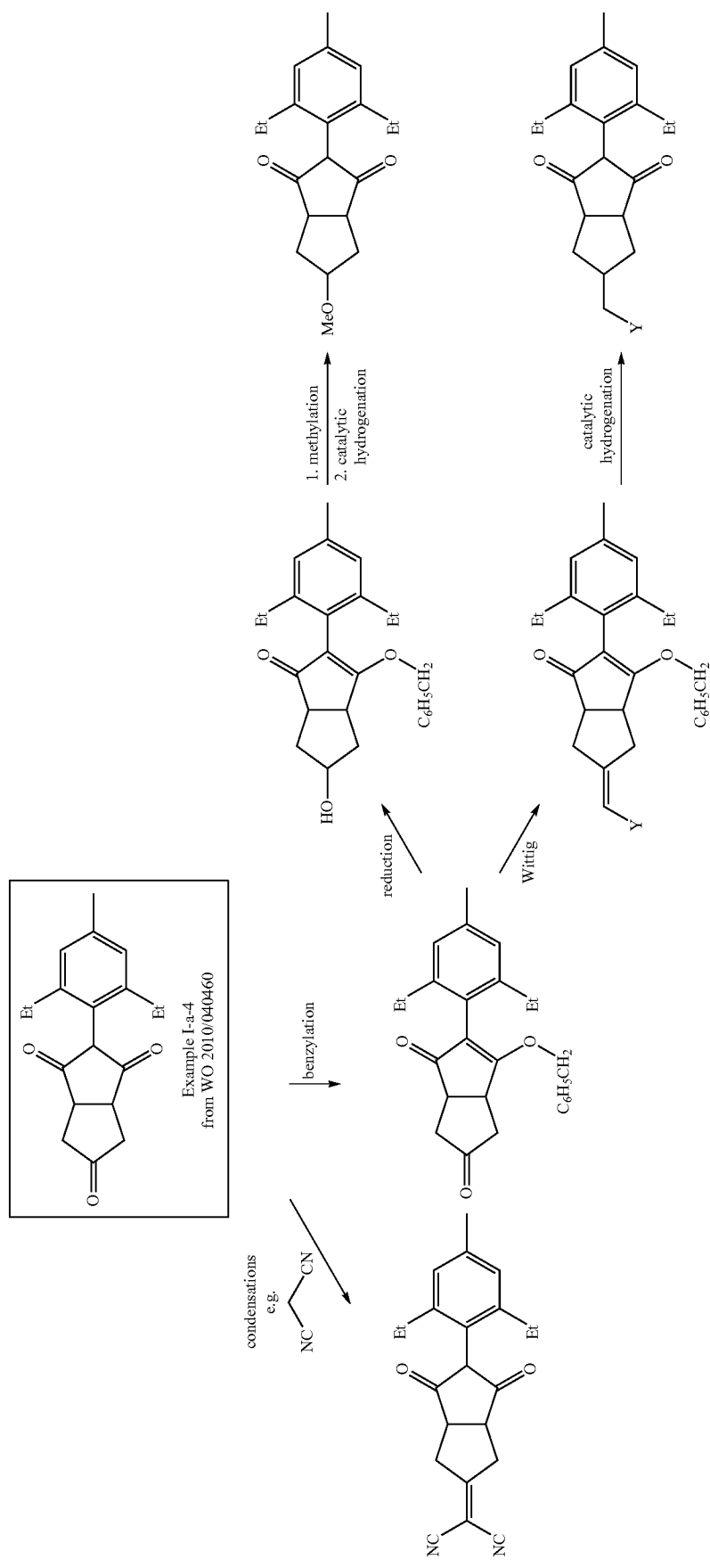
Scheme 1: Preparation process for the compounds of the formula (I-a) according to the invention illustrated in an exemplary manner with compound I-a-4 from WO 2010/040460

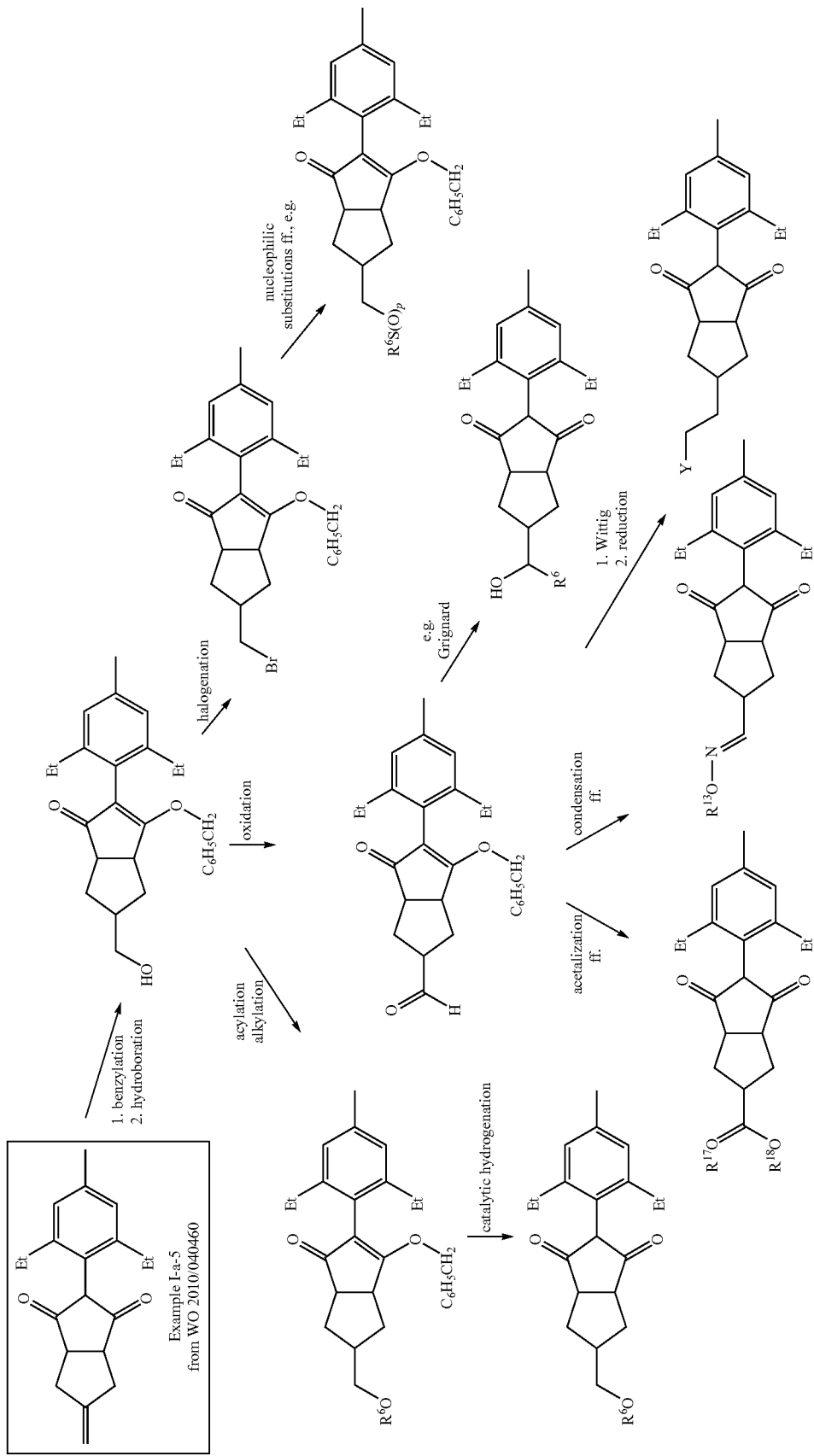

Moreover, it has been found (B) that the compounds of the formula (I-b) shown above in which G, Q, Y, $R^1$, $R^2$, $R^3$, $R^4$ and $R^5$ have the meaning given above are obtained when compounds of the formula (I-a) shown above in which Q, Y, $R^1$, $R^2$, $R^3$, $R^4$ and $R^5$ have the meaning given above are in each case reacted (α) with acid halides of the formula (III)

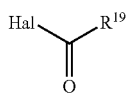           (III)

in which $R^{19}$ has the meaning given above and

Hal represents halogen (in particular chlorine or bromine)

or (β) with carboxylic anhydrides of the formula (IV)

$$R^{19}-CO-O-CO-R^{19} \qquad (IV)$$

in which $R^{19}$ has the meaning given above, if appropriate in the presence of a diluent and if appropriate in the presence of an acid binder;

(C) that the compounds of the formula (I-c) shown above in which Q, Y, $R^1$, $R^2$, $R^3$, $R^4$ and $R^5$ have the meaning given above and L represents oxygen are obtained when the compounds of the formula (I-a) shown above in which Q, Y, $R^1$, $R^2$, $R^3$, $R^4$ and $R^5$ have the meaning given above are in each case reacted with chloroformic esters or chloroformic thio esters of the formula (V)

$$R^{20}\text{-M-CO}-Cl \qquad (V)$$

in which $R^{20}$ and M have the meanings given above, if appropriate in the presence of a diluent and if appropriate in the presence of an acid binder;

(D) that compounds of the formula (I-c) shown above in which Q, Y, $R^1$, $R^2$, $R^3$, $R^4$ and $R^5$ have the meaning given above and L represents sulphur are obtained when compounds of the formula (I-a) shown above in which Q, Y, $R^1$, $R^2$, $R^3$, $R^4$ and $R^5$ have the meaning given above are in each case reacted with chloromonothioformic esters or chlordithioformic esters of the formula (VI)

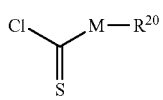           (VI)

in which

M and $R^{20}$ have the meanings given above, if appropriate in the presence of a diluent and if appropriate in the presence of an acid binder;

(E) that compounds of the formula (I-d) shown above in which Q, Y, $R^1$, $R^2$, $R^3$, $R^4$ and $R^5$ have the meaning given above are obtained when compounds of the formula (I-a) shown above in which Q, Y, $R^1$, $R^2$, $R^3$, $R^4$ and $R^5$ have the meaning given above are in each case reacted with sulphonyl chlorides of the formula (VII)

$$R^{21}-SO_2-Cl \qquad (VII)$$

in which $R^{21}$ has the meaning given above, if appropriate in the presence of a diluent and if appropriate in the presence of an acid binder, (F) that compounds of the formula (I-e) shown above in which Q, Y, $R^1$, $R^2$, $R^3$, $R^4$ and $R^5$ have the meaning given above are obtained when compounds of the formula (I-a) shown above in which Q, Y, $R^1$, $R^2$, $R^3$, $R^4$ and $R^5$ have the meaning given above are in each case reacted with phosphorus compounds of the formula (VIII)

           (VIII)

in which

L, $R^{22}$ and $R^{23}$ have the meanings given above and

Hal represents halogen (in particular chlorine or bromine), if appropriate in the presence of a diluent and if appropriate in the presence of an acid binder, (G) that compounds of the formula (I-f) shown above in which Q, Y, $R^1$, $R^2$, $R^3$, $R^4$ and $R^5$ have the meaning given above are obtained when compounds of the formula (I-a) in which Q, Y, $R^1$, $R^2$, $R^3$, $R^4$ and $R^5$ have the meaning given above are in each case reacted with metal compounds or amines of the formulae (IX) or (X), respectively $$\text{Met}(OR^{27})_t \qquad (IX)$$

           (X)

in which

Met represents a mono- or divalent metal (preferably an alkali metal or alkaline earth metal, such as lithium, sodium, potassium, magnesium or calcium), t represents the number 1 or 2 and $R^{27}$, $R^{28}$, $R^{29}$ and $R^{30}$ independently of one another represent hydrogen or alkyl (preferably $C_1$-$C_8$-alkyl), if appropriate in the presence of a diluent, (H) that compounds of the formula (I-g) shown above in which Q, Y, $R^1$, $R^2$, $R^3$, $R^4$, $R^5$ and $R^{24}$ have the meaning given above and $R^{25}$ is hydrogen are obtained when compounds of the formula (I-a) shown above in which Q, Y, $R^1$, $R^2$, $R^3$, $R^4$ and $R^5$ have the meaning given above are in each case reacted (α) with isocyanates or isothiocyanates of the formula (XI)

$$R^{24}-N=C=L \qquad (XI)$$

in which $R^{24}$ and L have the meanings given above, if appropriate in the presence of a diluent and if appropriate in the presence of a catalyst, or (β) with carbamoyl chlorides or thiocarbamoyl chlorides of the formula (XII)

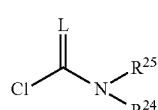           (XII)

in which

L, $R^{24}$ and $R^{25}$ have the meanings given above, if appropriate in the presence of a diluent and if appropriate in the presence of an acid binder.

Furthermore, it has been found that the novel compounds of the formula (I) are very effective as pesticides, preferably as insecticides, acaricides and/or as herbicides.

The formula (I) provides a general definition of the compounds according to the invention. Preferred substituents or ranges of the radicals given in the formulae mentioned above and below are illustrated below:

Preference is given to compounds of the formula (I) in which if

Q represents a bond, a $C_1$-$C_3$-alkylene, a $C_2$-$C_3$-alkenylene or a $C_2$-$C_3$-alkynylene chain, then Y represents the groups —$OR^6$, —$S(O)_pR^6$, —$CO_2R^7$, —CH=$CH_2$, cyano, —SCN, —$CONR^8R^9$, —$SO_2NR^8R^9$, $CR^{10}$=O, —$NR^{11}R^{12}$, —$CR^{10}$=N—$OR^{13}$, —$CR^{10}$=N—$R^{14}$, $CR^{10}$=N—$NR^{15}R^{16}$, —$CR^{10}(OR^{17}OR^{18})$, —$CR^{10}(SR^{17}OR^{18})$, —$CR^{10}(SR^{17}SR^{18})$, —$CR^{10}(NHR^{17}NHR^{18})$, —$CR^{10}(NHR^{17}OR^{18})$, —$CR^{10}(NHR^{17}SR^{18})$, —$CH(CN)_2$, —$CH(OH)R^6$, halogen, —O(C=M)$R^{10}$, —S(C=M)$R^{10}$, —O(C=M)$NR^{11}R^{12}$, —S(C=M)$NR^{11}R^{12}$, —NH(C=M)$NR^{11}R^{12}$, —O(C=M)$OR^7$, —S(C=M)$OR^7$, —NH(C=M)$OR^7$ or represents the group W, or Q, Y and $R^5$ together form one of the groups CHCN=, CH($CO_2C_1$-$C_6$-alkyl)=,

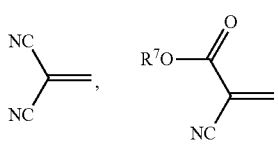 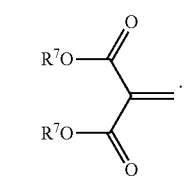 or

W represents one of the 3- to 7-membered saturated or partially saturated heterocycles listed below, which may be attached in various ways and may be mono- or polysubstituted by identical or different substituents from the group consisting of $R^{31}$ and $R^{32}$

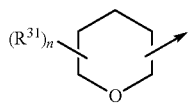 $W_1$

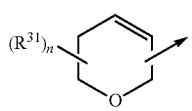 $W_2$

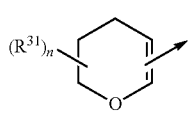 $W_3$

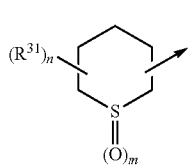 $W_4$

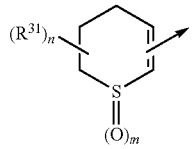 $W_5$

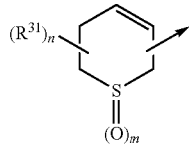 $W_6$

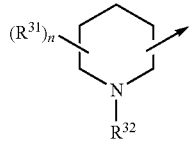 $W_7$

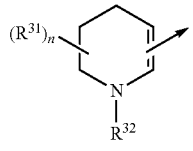 $W_8$

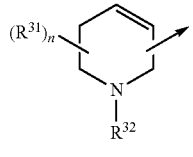 $W_9$

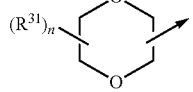 $W_{10}$

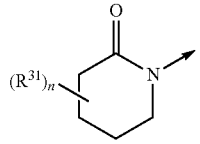 $W_{11}$

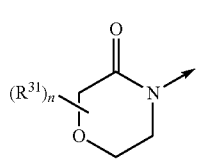 $W_{12}$

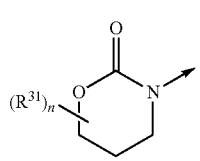 $W_{13}$

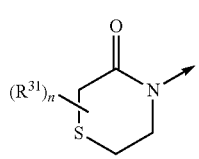 $W_{14}$

US 9,101,133 B2

19 -continued

W15, W16, W17, W18, W19, W20, W21, W22, W23, W24, W25, W26

20 -continued

W27, W28, W29, W30, W31, W32, W33, W34, W35, W36, W37, W38

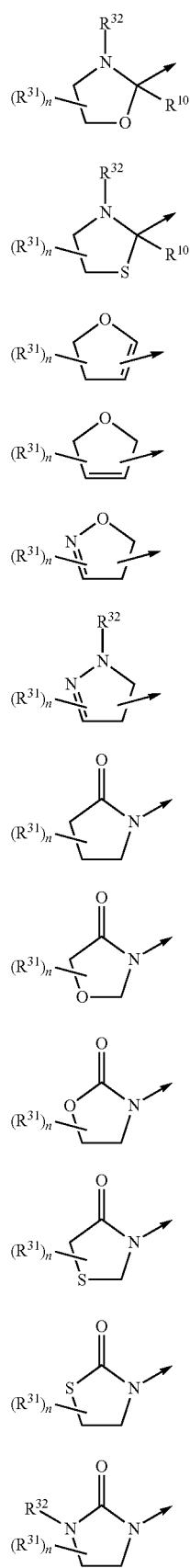
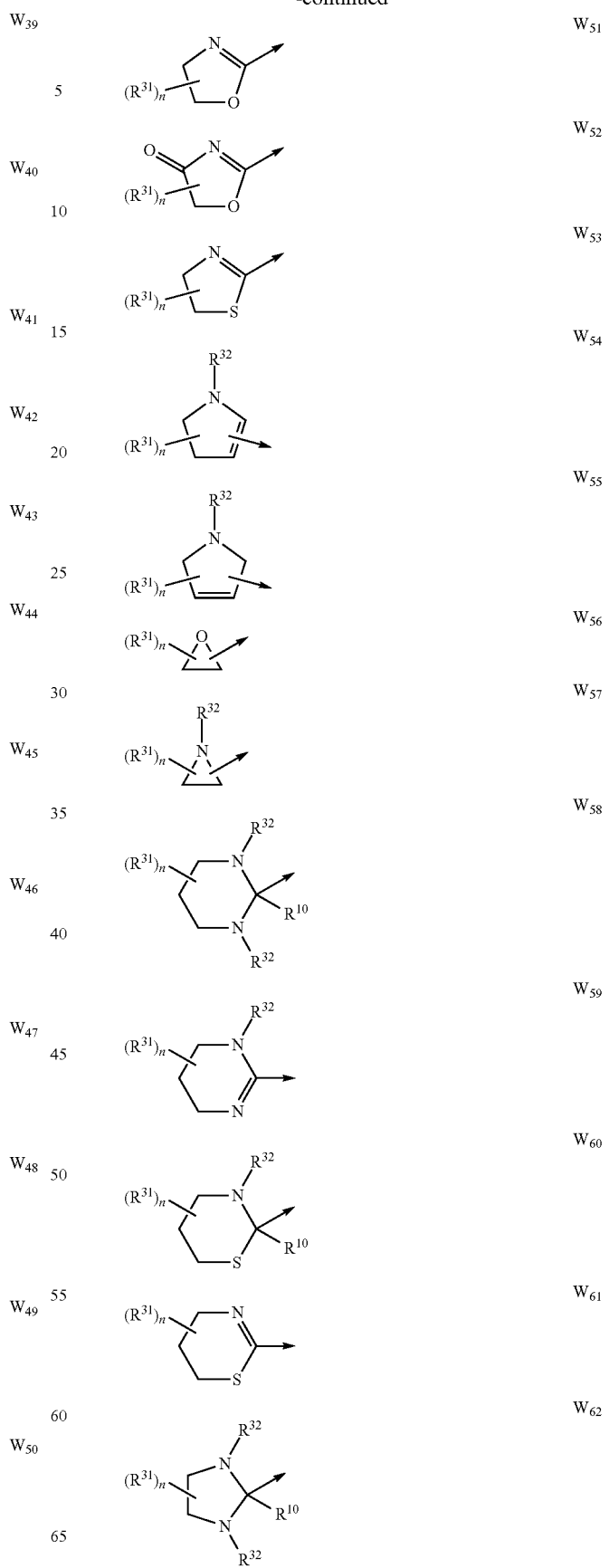

-continued

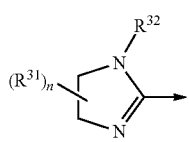

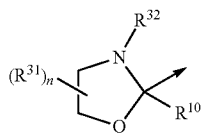

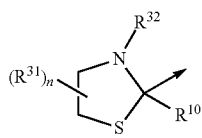

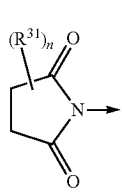

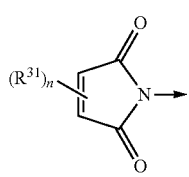

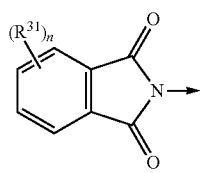

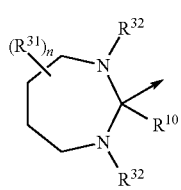

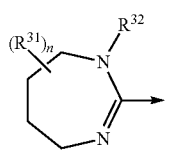

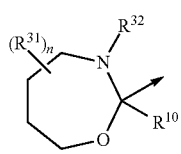

-continued

W₆₃ 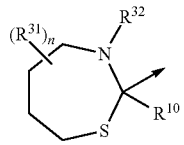

W₆₄ 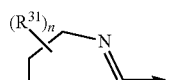

W₆₅ 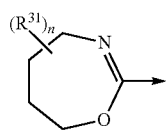

G represents hydrogen, methyl, ethyl or benzyl (a) or represents one of the groups

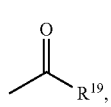 (b)

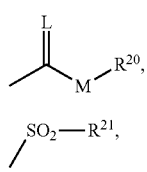 (c)

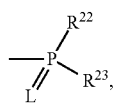 (d)

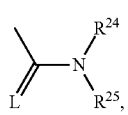 (e)

E (f)

(g)

E represents a metal ion equivalent, a tertiary sulphonium ion or an ammonium ion,
L represents oxygen or sulphur,
M represents oxygen or sulphur,
$R^1$ represents hydrogen, halogen, $C_1$-$C_4$-alkyl, halo-$C_1$-$C_4$-alkyl, $C_3$-$C_6$-cycloalkyl, halo-$C_3$-$C_6$-cycloalkyl, $C_2$-$C_4$-alkenyl, halo-$C_2$-$C_4$-alkenyl, $C_2$-$C_4$-alkynyl, halo-$C_2$-$C_4$-alkynyl, $C_1$-$C_4$-alkoxy, halo-$C_1$-$C_4$-alkoxy, $C_2$-$C_4$-alkynyloxy, halo-$C_2$-$C_4$-alkynyloxy, $C_2$-$C_4$-alkenyloxy, halo-$C_2$-$C_4$-alkenyloxy, $C_1$-$C_3$-alkylthio, $C_1$-$C_3$-alkylsulphinyl, $C_1$-$C_3$-alkylsulphonyl, halo-$C_1$-$C_3$-alkylthio, halo-$C_1$-$C_3$-alkylsulphinyl or halo-$C_1$-$C_3$-alkylsulphonyl,
$R^2$ and $R^3$ independently of one another are identical or different and represent hydrogen, halogen, $C_1$-$C_4$-alkyl, halo-$C_1$-$C_4$-alkyl, $C_2$-$C_4$-alkenyl, halo-$C_2$-$C_4$-alkenyl, $C_2$-$C_4$-alkynyl, halo-$C_2$-$C_4$-alkynyl, $C_1$-$C_4$-alkoxy, halo-$C_1$-$C_4$-alkoxy, $C_3$-$C_6$-cycloalkyl, $C_3$-$C_6$-cycloalkoxy, halo-$C_3$-$C_6$-cycloalkoxy, $C_2$-$C_4$-alkynyloxy, halo-$C_2$-$C_4$-alkynyloxy, $C_2$-$C_4$-alkenyloxy, halo-$C_2$-$C_4$-alkenyloxy, $C_1$-$C_3$-alkylthio, $C_1$-$C_3$-alkylsulphinyl, $C_1$-$C_3$-alkylsulphonyl, halo-$C_1$-$C_3$-alkylthio, halo-$C_1$-$C_3$-alkylsulphinyl, halo-$C_1$-$C_3$-alkylsulphonyl, phenyl or phenyl which is optionally mono- or polysubstituted by identical or different substituents from the group consisting of halogen, $C_1$-$C_4$-alkyl, halo-$C_1$-$C_4$-alkyl, $R^4$ represents hydrogen, halogen, $C_1$-$C_4$-alkyl, halo-$C_1$-$C_4$-alkyl, $C_3$-$C_6$-cycloalkyl, halo-$C_3$-$C_6$-cycloalkyl, $C_1$-$C_4$-alkoxy, halo-$C_1$-$C_4$-alkoxy, $C_3$-$C_4$-cycloalkoxy, or halo-$C_3$-$C_6$-cycloalkoxy, $R^5$ represents hydrogen or $C_1$-$C_4$-alkyl, $R^6$ represents hydrogen, $C_1$-$C_4$-alkyl, halo-$C_1$-$C_4$-alkyl, $C_3$-$C_6$-cycloalkyl, halo-$C_3$-$C_6$-cycloalkyl, $C_2$-$C_4$-alkenyl, halo-$C_2$-$C_4$-alkenyl, $C_2$-$C_4$-alkynyl, halo-$C_2$-$C_4$-alkynyl, $C_1$-$C_4$-alkoxy-$C_1$-$C_4$-alkyl, halo-$C_1$-$C_4$-alkoxy-$C_1$-$C_4$-alkyl, $C_3$-$C_6$-cycloalkoxy-$C_1$-$C_4$-alkyl, halo-$C_3$-$C_4$-cycloalkoxy-$C_1$-$C_4$-alkyl, represents benzyl, phenyl, heteroaryl, —CH$_2$-heteroaryl, —CH$_2$CH$_2$-heteroaryl, (for example pyranyl, tetrahydrofuranyl, pyrazolyl, thiazolyl, pyridyl, pyrimidyl, furanyl, thienyl, benzoxazolyl, oxazolyl), $C_1$-$C_4$-alkanoyl, halo-$C_1$-$C_4$-alkanoyl, benzoyl, each of which is optionally mono- or polysubstituted by identical or different substituents from the group consisting of halogen, cyano, nitro, $C_1$-$C_4$-alkyl, halo-$C_1$-$C_4$-alkyl, $C_3$-$C_6$-cycloalkyl, halo-$C_3$-$C_6$-cycloalkyl, halo-$C_2$-$C_4$-alkenyl, $C_2$-$C_4$-alkynyl, halo-$C_2$-$C_4$-alkynyl, $C_1$-$C_4$-alkoxyalkyl, halo-$C_1$-$C_4$-alkoxy-$C_1$-$C_6$-alkyl, $C_3$-$C_6$-cycloalkoxy-$C_1$-$C_6$-alkyl and halo-$C_3$-$C_6$-cycloalkoxy-$C_1$-$C_6$-alkyl, or represents benzoyl which is optionally mono- or polysubstituted by identical or different substituents from the group consisting of halogen, cyano, nitro, $C_1$-$C_4$-alkyl, halo-$C_1$-$C_4$-alkyl, $C_3$-$C_6$-cycloalkyl and halo-$C_3$-$C_6$-cycloalkyl, $R^7$ represents hydrogen, represents $C_1$-$C_4$-alkyl, $C_3$-$C_6$-cycloalkyl, $C_2$-$C_4$-alkenyl, each of which is optionally mono- or polysubstituted by identical or different substituents from the group consisting of halogen and $C_1$-$C_4$-alkoxy, or represents a cation E, $R^8$ and $R^9$ independently of one another are identical or different and represent hydrogen, $C_1$-$C_4$-alkyl, $C_2$-$C_4$-alkenyl, $C_2$-$C_4$-alkynyl, $C_3$-$C_6$-cycloalkyl, phenyl, benzyl, represent phenyl or benzyl, each of which is mono- or polysubstituted by identical or different substituents from the group consisting of halogen, nitro, cyano and $C_1$-$C_3$-alkyl or $R^8$ and $R^9$ together with the adjacent nitrogen atom form a morpholino, piperidino or pyrrolidino group, $R^{10}$ represents hydrogen, $C_1$-$C_4$-alkyl, halo-$C_1$-$C_4$ alkyl, $C_2$-$C_4$-alkenyl, halo-$C_2$-$C_4$-alkenyl, $C_2$-$C_4$-alkynyl, $C_3$-$C_6$-cycloalkyl, represents phenyl or benzyl, each of which is optionally mono- or polysubstituted by identical or different substituents from the group consisting of halogen, $C_1$-$C_4$-alkyl and halo-$C_1$-$C_4$-alkyl, $R^{11}$ and $R^{12}$ independently of one another are identical or different and represent hydrogen, $C_1$-$C_4$-alkyl, $C_2$-$C_4$-alkenyl, $C_2$-$C_4$-alkynyl, $C_3$-$C_6$-cycloalkyl, phenyl, benzyl, represent phenyl or benzyl, each of which is mono- or polysubstituted by identical or different substituents from the group consisting of halogen and $C_1$-$C_3$-alkyl or $R^{11}$ and $R^{12}$ together with the adjacent nitrogen atom form a morpholino, piperidino or pyrrolidino group, $R^{13}$ represents hydrogen or represents $C_1$-$C_4$-alkyl, $C_2$-$C_4$-alkenyl, $C_2$-$C_4$-alkynyl, $C_3$-$C_4$-cycloalkyl, $C_3$-$C_6$-cycloalkyl-$C_1$-$C_3$-alkyl, each of which is optionally mono- or polysubstituted by halogen, represents benzyl or —CH$_2$-heterocyclyl, each of which is optionally mono- or polysubstituted by identical or different substituents from the group consisting of halogen and $C_1$-$C_3$-alkyl, $R^{14}$ represents hydrogen, $C_1$-$C_4$-alkyl, halo-$C_1$-$C_4$ alkyl, $C_2$-$C_4$-alkenyl, $C_2$-$C_4$-alkynyl, halo-$C_2$-$C_4$-alkynyl, phenyl, benzyl or represents phenyl or benzyl, each of which is mono- or polysubstituted by identical or different substituents from the group consisting of halogen, $C_1$-$C_3$-alkyl, halo-$C_1$-$C_3$-alkyl, $C_3$-$C_6$-cycloalkyl, halo-$C_3$-$C_6$-cycloalkyl, $R^{15}$ and $R^{16}$ independently of one another are identical or different and represent hydrogen, $C_1$-$C_4$-alkyl, $C_2$-$C_4$-alkenyl, $C_2$-$C_4$-alkynyl, $C_3$-$C_6$-cycloalkyl, phenyl, benzyl, represent phenyl or benzyl, each of which is mono- or polysubstituted by identical or different substituents from the group consisting of halogen and $C_1$-$C_3$-alkyl or $R^{15}$ and $R^{16}$ together with the adjacent nitrogen atom form a morpholino, piperidino or pyrrolidino group, $R^{17}$ represents hydrogen, represents $C_1$-$C_4$-alkyl, benzyl or halo-$C_1$-$C_4$-alkyl, each of which is optionally interrupted once or more by identical or different radicals from the group consisting of oxygen and sulphur, $R^{18}$ represents hydrogen, represents $C_1$-$C_4$-alkyl, benzyl or halo-$C_1$-$C_4$-alkyl, each of which is optionally interrupted once or more by identical or different radicals from the group consisting of oxygen and sulphur, $R^{19}$ represents optionally halogen-substituted $C_1$-$C_6$-alkyl, $C_2$-$C_6$-alkenyl, $C_1$-$C_4$-alkoxy-$C_1$-$C_4$-alkyl, $C_1$-$C_3$-alkylthio-$C_1$-$C_4$-alkyl, poly-$C_1$-$C_4$-alkoxy-$C_1$-$C_4$-alkyl or represents $C_3$-$C_6$-cycloalkyl which is optionally mono- or polysubstituted by identical or different substituents from the group consisting of halogen, $C_1$-$C_4$-alkyl and $C_1$-$C_4$-alkoxy and in which optionally one or more (preferably not more than two) not directly adjacent ring members are replaced by oxygen and/or sulphur, represents in each case optionally halogen- or $C_1$-$C_4$-alkyl-substituted phenyl, phenyl-$C_1$-$C_4$-alkyl, hetaryl (for example pyrazolyl, thiazolyl, pyridyl, pyrimidyl, furanyl or thienyl), phenoxy-$C_1$-$C_4$-alkyl or hetaryloxy-$C_1$-$C_4$-alkyl (for example pyridyloxy-$C_1$-$C_4$-alkyl, pyrimidyloxy-$C_1$-$C_4$-alkyl or thiazolyloxy-$C_1$-$C_4$-alkyl), $R^{20}$ represents $C_1$-$C_6$-alkyl, $C_2$-$C_6$-alkenyl, $C_1$-$C_4$-alkoxy-$C_1$-$C_4$-alkyl, poly-$C_1$-$C_4$-alkoxy-$C_1$-$C_4$-alkyl, each of which is optionally mono- or polysubstituted by identical or different halogen, or represents $C_3$-$C_6$-cycloalkyl in which optionally one or more (preferably not more than two) not directly adjacent ring members are replaced by oxygen and/or sulphur, or represents benzyl, $R^{21}$, $R^{22}$ and $R^{23}$ independently of one another are identical or different and represent $C_1$-$C_4$-alkyl, $C_1$-$C_4$-alkoxy, $C_1$-$C_4$-alkylamino, $C_1$-$C_4$-dialkylamino, $C_1$-$C_3$-alkylthio, $C_2$-$C_4$-alkenylthio, $C_3$-$C_6$-cycloalkylthio, each of which is optionally mono- or polysubstituted by identical or different halogen, or represent phenyl, benzyl, phenoxy or phenylthio, each of which is optionally mono- or polysubstituted by identical or different substituents from the group consisting of halogen, $C_1$-$C_6$-alkyl, $C_1$-$C_6$-alkoxy, $C_1$-$C_4$-haloalkyl, $C_1$-$C_4$-haloalkoxy, cyano and nitro, $R^{24}$ and $R^{25}$ independently of one another are identical or different and represent hydrogen, represent $C_1$-$C_6$-alkyl, $C_3$-$C_6$-cycloalkyl, $C_2$-$C_6$-alkenyl, $C_1$-$C_6$-alkoxy, $C_1$-$C_6$-alkoxy-$C_1$-$C_4$-alkyl, each of which is optionally mono- or polysubstituted by identical or different halogen, represent benzyl or phenyl, optionally mono- or polysubstituted by identical or different substituents from the group consisting of halogen and $C_1$-$C_4$-alkyl or $R^{24}$ and $R^{25}$ together with the adjacent nitrogen atom form a morpholino, piperidino or pyrrolidino group, $R^{31}$ represents halogen, cyano, nitro, $C_1$-$C_6$-alkyl, halo-$C_1$-$C_6$-alkyl, $C_3$-$C_6$-cycloalkyl, halo-$C_3$-$C_6$-cycloalkyl, $C_2$-$C_6$-alkenyl, halo-$C_2$-$C_6$-alkenyl, $C_2$-$C_6$-alkynyl, halo-$C_2$-$C_6$-alkynyl, $C_1$-$C_6$-alkoxy, halo-$C_1$-$C_6$-alkoxy, $C_3$-$C_6$-cycloalkoxy, halo-$C_3$-$C_6$-cycloalkoxy, $C_1$-$C_6$-alkynyloxy, halo-$C_1$-$C_6$-alkynyloxy, $C_2$-$C_6$-alkenyloxy, halo-$C_2$-$C_6$-alkenyloxy, $C_1$-$C_3$-alkylthio, $C_1$-$C_3$-alkylsulphinyl, $C_1$-$C_3$-alkylsulphonyl, halo-$C_1$-$C_3$-alkylthio, halo-$C_1$-$C_3$-alkylsulphinyl, $C_1$-$C_3$-alkylsulphonyl, $C_1$-$C_6$-alkylcarbonyl, $C_1$-$C_6$-alkoxycarbonyl, $C_1$-$C_6$-alkylcarbamoyl, amino, $C_1$-$C_6$-alkylamino or $C_1$-$C_6$-dialkylamino, $R^{32}$ represents hydrogen, halogen, cyano, nitro, $C_1$-$C_6$-alkyl, halo-$C_1$-$C_6$-alkyl, $C_3$-$C_6$-cycloalkyl, halo-$C_3$-$C_6$-cycloalkyl, $C_2$-$C_6$-alkenyl, halo-$C_2$-$C_6$-alkenyl, $C_2$-$C_6$-alkynyl, halo-$C_2$-$C_6$-alkynyl, $C_1$-$C_3$-alkylsulphonyl, $C_1$-$C_3$-alkylsulphonyl, $C_1$-$C_6$-alkylcarbonyl, $C_1$-$C_6$-alkoxycarbonyl, $C_1$-$C_6$-alkylcarbamoyl, amino, $C_1$-$C_6$-alkylamino or $C_1$-$C_6$-dialkylamino, n represents the number 0, 1, 2, 3, 4, 5 or 6, P represents the number 0, 1 or 2, or if Q, Y and $R^5$ together represent the group $CH_2$=, then G represents methyl, ethyl or benzyl (a).

Particular preference is given to compounds of the formula (I) in which if

Q represents a bond, —$CH_2$—, —CH=CH— or —$CH_2CH_2$—, then

Y represents the groups —$OR^6$, —$CO_2R^7$, —CH=$CH_2$, cyano, —$CR^{10}$=O, —$CR^{10}$=N—$OR^{13}$, —CH($OR^{17}OR^{18}$), S(O)$_pR^6$, —SCN, —$CONR^8R^9$, —CH(CN)$_2$, —CH(OH)$R^6$, halogen, —OC=$MR^{10}$, —S(C=M)$R^{10}$, —O(C=M)NR$^{11}R^{12}$, —O(C=M)O$R^7$, —NH(C=M)O$R^7$, or represents the group W, or Q, Y and $R^5$ together form one of the groups W represents G represents hydrogen, ethyl or benzyl or represents one of the groups $R^1$ represents methyl, ethyl, methoxy, ethoxy, halogen or cyclopropyl, $R^2$ represents methyl, ethyl or 4-chlorophenyl, $R^3$ represents hydrogen, methyl, ethyl or cyclopropyl, $R^4$ represents hydrogen, methyl or ethyl, $R^5$ represents hydrogen, $R^6$ represents hydrogen, methyl, ethyl, —$CH_2$—CH(CH$_3$)$_2$, —$CH_2$—CH=$CH_2$, cyano, trifluoromethyl, methoxymethyl, 2-benzoxazolyl, 4,5-dimethylthiazol-2-yl, 2-oxazolyl, 2-tetrahydrofuryl or the 2-pyranyl group, $R^7$ represents hydrogen, methyl, ethyl, isopropyl or n-propyl, $R^8$ represents hydrogen or methyl, $R^9$ represents hydrogen or methyl, or $R^8$ and $R^9$ together with the nitrogen atom form the group $R^{10}$ represents hydrogen, methyl, t-butyl, fluoromethyl, difluoromethyl or trifluoromethyl, $R^{11}$ represents hydrogen or methyl, $R^{12}$ represents hydrogen, methyl, benzyl or phenyl, $R^{13}$ represents hydrogen, methyl, isopropyl, —$CH_2CH$=$CCl_2$, —$CH_2CH$=$CH_2$, —$CH_2C$≡CH or —$CH_2C_3H_5$, $R^{17}$ represents methyl, ethyl or n-propyl $R^{18}$ represents methyl, ethyl or n-propyl, $R^{19}$ represents $C_1$-$C_4$-alkyl $R^{20}$ represents methyl, ethyl or isopropyl, p represents 0 or 2, M represents oxygen or sulphur, or if Q, Y and $R^5$ together represent the group $CH_2$=, then G represents methyl, ethyl or benzyl (a).

Very particular preference is given to compounds of the formula (I) in which

Q represents a bond, —CH$_2$—, —CH$_2$CH$_2$— or —CH=CH—,

Y represents the groups —OR$^6$, —CO$_2$R$^7$, —CH=CH$_2$, cyano, —CR$^{10}$=O, —CR$^{10}$=N—OR$^{13}$, —CH(OR$^{17}$OR$^{18}$), S(O)$_p$R$^6$, —SCN, —CONR$^8$R$^9$, —CH(CN)$_2$, —CH(OH)R$^6$, bromine, —O(C=O)R$^{10}$, —S(C=P)R$^{10}$, —O(C=O)NR$^{11}$R$^{12}$, or represents the group W, or Q, Y and R$^5$ together form one of the groups

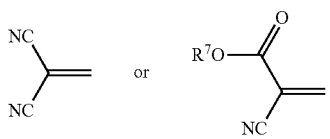

W represents

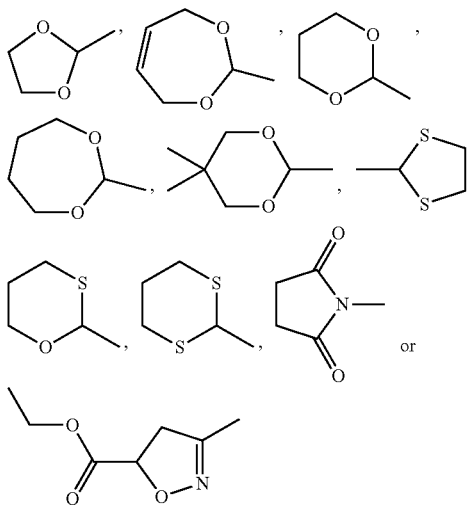

G represents hydrogen, ethyl, benzyl (a) or represents one of the groups

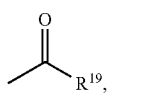

(b)

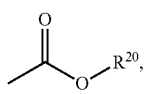

(c)

R$^1$ represents methyl or ethyl (ethyl is especially preferred),
R$^2$ represents methyl,
R$^3$ represents hydrogen,
R$^4$ represents methyl or ethyl (ethyl is especially preferred),
R$^5$ represents hydrogen,
R$^6$ represents hydrogen, methyl, ethyl, —CH$_2$—CH(CH$_3$)$_2$, —CH$_2$—CH=CH$_2$, trifluoromethyl, methoxymethyl, 2-benzoxazolyl, 4,5-dimethylthiazol-2-yl, 2-oxazolyl, 2-tetrahydrofuryl or the 2-pyranyl group,
R$^7$ represents hydrogen, methyl or ethyl,
R$^8$ represents hydrogen or methyl,
R$^9$ represents hydrogen or methyl,
or R$^8$ and R$^9$ together with the nitrogen atom represent the group

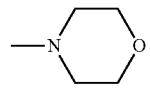

R$^{10}$ represents hydrogen, methyl, t-butyl or trifluoromethyl,
R$^{11}$ represents hydrogen or methyl,
R$^{12}$ represents hydrogen, methyl, benzyl or phenyl,
R$^{13}$ represents hydrogen, methyl, isopropyl, —CH$_2$CH=CCl$_2$, —CH$_2$CH=CH$_2$, —CH$_2$C≡CH or —CH$_2$C$_3$H$_5$,
R$^{17}$ represents methyl or ethyl,
R$^{18}$ represents methyl or ethyl,
R$^{19}$ represents ethyl, tert-butyl or isopropyl,
R$^{20}$ represents methyl, ethyl or isopropyl,
p represents 0 or 2.

Emphasis is given to compounds of the formula (I) in which

Q, Y and R$^5$ together represent the group CH$_2$=,
G represents benzyl (a),
R$^1$ represents ethyl,
R$^2$ represents methyl,
R$^3$ represents hydrogen,
R$^4$ represents ethyl.

The general or preferred radical definitions or illustrations listed above can be combined with one another as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Emphasis according to the invention is given to the compounds of the formula (I) which contain a combination of the meanings listed above as emphasized.

Special preference according to the invention is given to the compounds of the formula (I) which contain a combination of the meanings listed above as being especially preferred.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Optionally substituted radicals may be mono- or polysubstituted unless indicated otherwise, and in the case of multiple substitutions the substituents can be identical or different.

With particular emphasis, G represents hydrogen.

In addition to the compounds mentioned in the Preparation Examples, the following compounds of the formula (I-1-a) may be specifically mentioned:

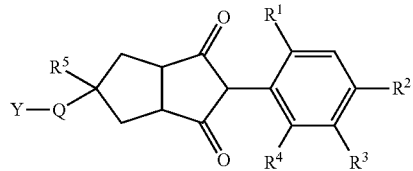

TABLE 1

| R¹ = CH₃, R² = CH₃, R³ = CH₃, R⁴ = H, R⁵ = H, | |
|---|---|
| Y | Q |
| —CO₂H | bond |
| —CO₂Me | bond |
| —CO₂Et | bond |
| —CO₂$^i$Pr | bond |
| —CONH₂ | bond |
| —CONHCH₃ | bond |
| —CON(CH₃)₂ | bond |
| 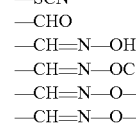 | bond |
| —CN | bond |
| —SCN | bond |
| —CHO | bond |
| —CH=N—OH | bond |
| —CH=N—OCH₃ | bond |
| —CH=N—O—CH₂C=CH₂ | bond |
| —CH=N—O—CH₂C=CCl₃ | bond |
| —CH=N—O—CH₂C≡CH | bond |
| —CH=N—O$^i$Pr | bond |
| CH₃(C=O)— | bond |
| 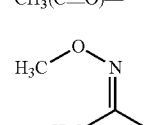 | bond |
| —CH=CH₃ | bond |
| —CH(CN)₃ | bond |
| —C(CN)(CO₂CH₃) | bond |
| —C(CO₂CH₃)₂ | bond |
| 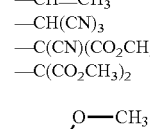 | bond |
| 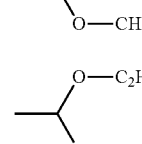 | bond |
| 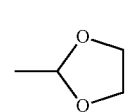 | bond |

TABLE 1-continued

| R¹ = CH₃, R² = CH₃, R³ = CH₃, R⁴ = H, R⁵ = H, | |
|---|---|
| Y | Q |
| 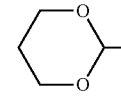 | bond |
| 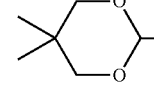 | bond |
| 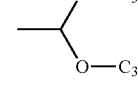 | bond |
| 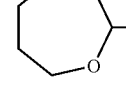 | bond |
| 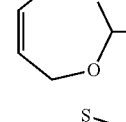 | bond |
| 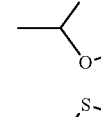 | bond |
| 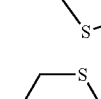 | bond |
| 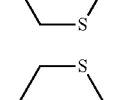 | bond |
| 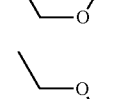 | bond |
| 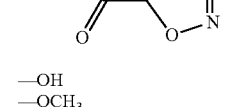 | bond |
| —OH | —CH₂— |
| —OCH₃ | —CH₂— |
| —OCF₂ | —CH₂— |
| —OCHF₂ | —CH₂— |
| —OCH₂F | —CH₂— |
| —OCH₂CH₃ | —CH₂— |
| —OCH₂OCH₃ | —CH₂— |
| 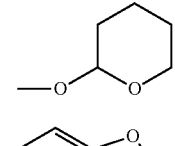 | —CH₂— |
| 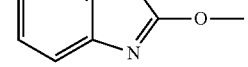 | —CH₂— |

TABLE 1-continued

R¹ = CH₃, R² = CH₃, R³ = CH₃, R⁴ = H, R⁵ = H,

| Y | Q |
|---|---|
| 2-methoxy-thiazole | —CH₂— |
| —O(C=O)—OCH₃ | —CH₂— |
| —O(C=O)—OCF₃ | —CH₂— |
| —O(C=O)—OC₂H₅ | —CH₂— |
| —O(C=O)—N(CH₃)₂ | —CH₂— |
| —O(C=O)—NHC₆H₅ | —CH₂— |
| —O(C=O)—NHCH₂C₆H₅ | —CH₂— |
| —O(C=O)—NHCH₃ | —CH₂— |
| —O(C=S)—NHC₆H₅ | —CH₂— |
| —CHO | —CH₂— |
| —CO₂H | —CH₂— |
| —CO₂Me | —CH₂— |
| —CO₂Et | —CH₂— |
| —CO₂ⁱPr | —CH₂— |
| —CONH₂ | —CH₂— |
| —CONHCH₃ | —CH₂— |
| —CON(CH₃)₂ | —CH₂— |
| 4-acetyl-thiomorpholine | —CH₂— |
| 2-tetrahydrofuryl | —CH₂— |
| 4-tetrahydropyranyl | —CH₂— |
| 4-piperidinyl | —CH₂— |
| 1-acetyl-4-piperidinyl | —CH₂— |
| CH(OCH₃)₂ | —CH₂— |
| CH(OC₂H₅)₂ | —CH₂— |
| 2-(1,3-dioxolanyl) | —CH₂— |
| 2-(1,3-dioxanyl) | —CH₂— |
| 2,5,5-trimethyl-1,3-dioxanyl | —CH₂— |
| CH(OC₃H₇)₂ | —CH₂— |
| 2-(1,3-dioxepanyl) | —CH₂— |
| 2-(4,7-dihydro-1,3-dioxepinyl) | —CH₂— |
| 2-(1,3-oxathiolanyl) | —CH₂— |
| 2-(1,3-dithiolanyl) | —CH₂— |
| 2-(1,3-dithianyl) | —CH₂— |
| 2-(1,3-oxathianyl) | —CH₂— |
| —CN | —CH₂— |
| —Cl | —CH₂— |
| —Br | —CH₂— |
| —SCN | —CH₂— |
| —CH=N—OH | —CH₂— |
| —CH=N—OCH₃ | —CH₂— |
| —CH=N—O—CH₂C=CH₂ | —CH₂— |
| —CH=N—O—CH₂C=CCl₃ | —CH₂— |
| —CH=N—O—CH₂C≡CH | —CH₂— |
| —CH=N—OⁱPr | —CH₂— |
| (CH₃)₂C=N—OCH₃ | —CH₂— |
| —SCH₂CH=CH₂ | —CH₂— |
| —SCH₃ | —CH₂— |
| —SO₂CH₃ | —CH₂— |
| CH₃(C=O)S— | —CH₂— |
| (CH₃)₂CHCH₂SO₂— | —CH₂— |
| (CH₃)₂CHCH₂S— | —CH₂— |
| 2-methylthio-oxazole | —CH₂— |

TABLE 1-continued

R¹ = CH₃, R² = CH₃, R³ = CH₃, R⁴ = H, R⁵ = H,

| Y | Q |
|---|---|
| 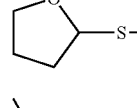 | —CH₂— |
| 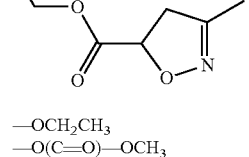 | —CH₂— |
| —OCH₂CH₃ | —CH=CH— |
| —O(C=O)—OCH₃ | —CH=CH— |
| —O(C=O)—OC₂H₅ | —CH=CH— |
| —O(C=O)—N(CH₃)₂ | —CH=CH— |
| —O(C=O)—NHC₆H₅ | —CH=CH— |
| —O(C=O)—NHCH₃ | —CH=CH— |
| —O(C=S)—NHC₆H₅ | —CH=CH— |
| —CO₂H | —CH=CH— |
| —CO₂Me | —CH=CH— |
| —CO₂Et | —CH=CH— |
| —CO₂ⁱPr | —CH=CH— |
| —CONH₂ | —CH=CH— |
| 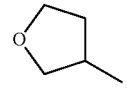 | —CH=CH— |
|  | —CH=CH— |
|  | —CH=CH— |
| 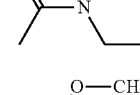 | —CH=CH— |
| 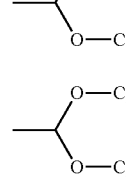 | —CH=CH— |
| 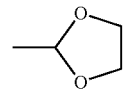 | —CH=CH— |
|  | —CH=CH— |
| 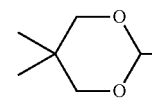 | —CH=CH— |
| 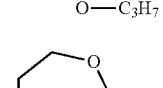 | —CH=CH— |

TABLE 1-continued

R¹ = CH₃, R² = CH₃, R³ = CH₃, R⁴ = H, R⁵ = H,

| Y | Q |
|---|---|
| 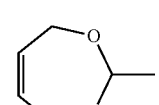 | —CH=CH— |
| 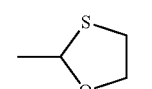 | —CH=CH— |
| 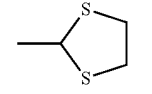 | —CH=CH— |
| 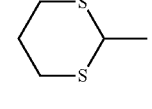 | —CH=CH— |
| 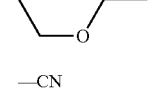 | —CH=CH— |
| 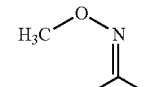 | —CH=CH— |
| 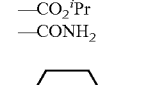 | —CH=CH— |
| —CN | —CH₂CH₂— |
| CH₃(C=O)— | —CH₂CH₂— |
|  | —CH₂CH₂— |
| —CHO | —CH₂CH₂— |
| —OCH₃ | —CH₂CH₂— |
| —OCH₂CH₃ | —CH₂CH₂— |
| —O(C=O)—OCH₃ | —CH₂CH₂— |
| —O(C=O)—OC₂H₅ | —CH₂CH₂— |
| —O(C=O)—N(CH₃)₂ | —CH₂CH₂— |
| —O(C=O)—NHC₆H₅ | —CH₂CH₂— |
| —O(C=O)—NHCH₃ | —CH₂CH₂— |
| —O(C=S)—NHC₆H₅ | —CH₂CH₂— |
| —CO₂H | —CH₂CH₂— |
| —CO₂Me | —CH₂CH₂— |
| —CO₂Et | —CH₂CH₂— |
| —CO₂ⁱPr | —CH₂CH₂— |
| —CONH₂ | —CH₂CH₂— |
|  | —CH₂CH₂— |

TABLE 1-continued

R¹ = CH₃, R² = CH₃, R³ = CH₃, R⁴ = H, R⁵ = H,

| Y | Q |
|---|---|
| (tetrahydrofuran-3-yl, methyl) | —CH₂CH₂— |
| (tetrahydrofuran-2-yl, methyl) | —CH₂CH₂— |
| (4-methylpiperidin-4-yl, HN) | —CH₂CH₂— |
| (1-acetyl-4-methylpiperidin-4-yl) | —CH₂CH₂— |
| (1,1-dimethoxyethyl) | —CH₂CH₂— |
| (1,1-diethoxyethyl) | —CH₂CH₂— |
| (2-methyl-1,3-dioxolan-2-yl) | —CH₂CH₂— |
| (2-methyl-1,3-dioxan-2-yl) | —CH₂CH₂— |
| (2,5,5-trimethyl-1,3-dioxan-2-yl) | —CH₂CH₂— |
| (1,1-dipropoxyethyl) | —CH₂CH₂— |
| (2-methyl-1,3-dioxepan-2-yl) | —CH₂CH₂— |
| (2-methyl-4,7-dihydro-1,3-dioxepin-2-yl) | —CH₂CH₂— |
| (2-methyl-1,3-oxathiolan-2-yl) | —CH₂CH₂— |
| (2-methyl-1,3-dithiolan-2-yl) | —CH₂CH₂— |

TABLE 1-continued

R¹ = CH₃, R² = CH₃, R³ = CH₃, R⁴ = H, R⁵ = H,

| Y | Q |
|---|---|
| (2-methyl-1,3-dithian-2-yl) | —CH₂CH₂— |
| (2-methyl-1,3-oxathian-2-yl) | —CH₂CH₂— |

Table 2: Q and Y as mentioned in Table 1 and
R¹=C₂H₅, R²=CH₃, R³=CH₃, R⁴=H, R⁵=H,
Table 3: Q and Y as mentioned in Table 1 and
R¹=C₂H₅, R²=CH₃, R³=C₂H₅, R⁴=H, R⁵=H,
Table 4: Q and Y as mentioned in Table 1 and
R¹=C₂H₅; R²=C₂H₅; R³=C₂H₅, R⁴=H, R⁵=H,
Table 5: Q and Y as mentioned in Table 1 and
R¹=▷- ; R²=CH₃; R³=CH₃; R⁴=H, R⁵=H,
Table 6: Q and Y as mentioned in Table 1 and
R¹=▷- ; R²=CH₃; R³=C₂H₅, R⁴=H, R⁵=H,
Table 7: Q and Y as mentioned in Table 1 and
R¹=OCH₃; R²=CH₃; R³=CH₃, R⁴=H, R⁵=H,
Table 8: Q and Y as mentioned in Table 1 and
R¹=OC₂H₅; R²=CH₃; R³=CH₃, R⁴=H, R⁵=H,
Table 9: Q and Y as mentioned in Table 1 and
R¹=OCH₃; R²=CH₃; R³=C₂H₅, R⁴=H, R⁵=H,
Table 10: Q and Y as mentioned in Table 1 and
R¹=OC₂H₅; R²=CH₃; R³=C₂H₅, R⁴=H, R⁵=H,
Table 11: Q and Y as mentioned in Table 1 and
R¹=C₂H₅; R²=CH₃; R³=H, R⁴=H, R⁵=H,
Table 12: Q and Y as mentioned in Table 1 and
R¹=▷- R²=CH₃; R³=▷- , R⁴=H, R⁵=H,
Table 13: Q and Y as mentioned in Table 1 and
R¹=C₂H₅; R²=C₂H₅; R³=CH₃, R⁴=H, R⁵=H,
Table 14: Q and Y as mentioned in Table 1 and
R¹=CH₃; R²=4-chlorophenyl; R³=H, R⁴=CH₃, R⁵=H.

Surprisingly, it has now also been found that the compounds of the formula (I), when used together with the crop plant compatibility-improving compounds (safener/antidotes) described below, efficiently prevent damage to the crop plants and can be used in a particularly advantageous manner as broad-spectrum combination preparations for the selective control of unwanted plants in crops of useful plants, such as, for example, in cereals, but also in maize, soya beans and rice.

The invention also provides selective herbicidal compositions comprising an effective amount of an active compound combination comprising, as components, a') at least one compound of the formula (I), in which R¹, R², R³, R⁴, R⁵, Y, Q and G have the meaning given above and (b') at least one crop plant compatibility-improving compound (safener).

Suitable safeners are, for example, the following groups of compounds:

S1) Compounds of the formula (S1)

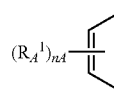

where the symbols and indices have the following meanings:

$n_A$ is a natural number from 0 to 5, preferably from 0 to 3;

$R_A^1$ is halogen, $(C_1-C_4)$-alkyl, $(C_1-C_4)$-alkoxy, nitro or $(C_1-C_4)$-haloalkyl;

$W_A$ is an unsubstituted or substituted divalent heterocyclic radical from the group consisting of partially unsaturated or aromatic five-membered heterocycles having 1 to 3 hetero ring atoms from the group consisting of N and O, where at least one nitrogen atom and at most one oxygen atom is present in the ring, preferably a radical from the group consisting of $(W_A^1)$ to $(W_A^4)$,

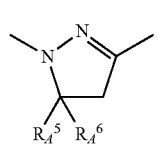
$(W_A^1)$

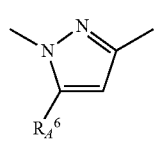
$(W_A^2)$

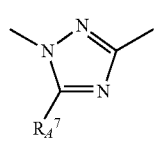
$(W_A^3)$

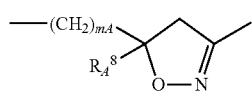
$(W_A^4)$ $m_A$ is 0 or 1;

$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S1) and which is unsubstituted or substituted by radicals from the group consisting of $(C_1-C_4)$-alkyl, $(C_1-C_4)$-alkoxy and optionally substituted phenyl, preferably a radical of the formula $OR_A^3$, $NHR_A^4$ or $N(CH_3)_2$, in particular of the formula $OR_A^3$;

$R_A^3$ is hydrogen or an unsubstituted or substituted aliphatic hydrocarbon radical having preferably a total of 1 to 18 carbon atoms;

$R^4$ is hydrogen, $(C_1-C_6)$-alkyl, $(C_1-C_6)$-alkoxy or substituted or unsubstituted phenyl;

$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$ where $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the type of the dichlorophenylpyrazoline-3-carboxylic acid ($S1^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds, as described in WO-A-91/07874;

b) derivatives of dichlorophenylpyrazolecarboxylic acid ($S1^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds, as described in EP-A-333 131 and EP-A-269 806;

c) derivatives of 1,5-diphenylpyrazole-3-carboxylic acid ($S1^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds, as described, for example, in EP-A-268554;

d) compounds of the type of the triazolecarboxylic acids ($S1^d$), preferably compounds such as fenchlorazole(-ethyl), i.e. ethyl 1-(2,4-dichlorophenyl)-5-trichloromethyl-(1H)-1,2,4-triazole-3-carboxylate (S1-7), and related compounds, as described in EP-A-174 562 and EP-A-346 620;

e) compounds of the type of the 5-benzyl- or 5-phenyl-2-isoxazoline-3-carboxylic acid or the 5,5-diphenyl-2-isoxazoline-3-carboxylic acid ($S1^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds, as described in WO-A-91/08202, or 5,5-diphenyl-2-isoxazolinecarboxylic acid (S1-10) or ethyl 5,5-diphenyl-2-isoxazolinecarboxylate (S1-11) ("isoxadifen-ethyl") or n-propyl 5,5-diphenyl-2-isoxazolinecarboxylate (S1-12) or ethyl 5-(4-fluorophenyl)-5-phenyl-2-isoxazoline-3-carboxylate (S1-13), as described in the patent application WO-A-95/07897.

S2) Quinoline derivatives of the formula (S2)

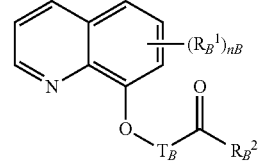
(S2)

where the symbols and indices have the following meanings:

$R_B^1$ is halogen, $(C_1-C_4)$-alkyl, $(C_1-C_4)$-alkoxy, nitro or $(C_1-C_4)$-haloalkyl;

$n_B$ is a natural number from 0 to 5, preferably from 0 to 3;

$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S2) and which is unsubstituted or substituted by radicals from the group consisting of $(C_1-C_4)$-alkyl, $(C_1-C_4)$-alkoxy and optionally substituted phenyl, preferably a radical of the formula $OR_B^3$, $NHR_B^4$ or $N(CH_3)_2$, in particular of the formula $OR_B^3$;

$R_B^3$ is hydrogen or an unsubstituted or substituted aliphatic hydrocarbon radical having preferably a total of 1 to 18 carbon atoms;

$R_B^4$ is hydrogen, $(C_1-C_6)$-alkyl, $(C_1-C_6)$-alkoxy or substituted or unsubstituted phenyl;

$T_B$ is a ($C_1$- or $C_2$)-alkanediyl chain which is unsubstituted or substituted by one or two ($C_1$-$C_4$)-alkyl radicals or by [($C_1$-$C_3$)-alkoxy]carbonyl;

preferably:

a) compounds of the type of the 8-quinolinoxyacetic acid ($S2^a$), preferably 1-methylhexyl (5-chloro-8-quinolinoxy)acetate ("cloquintocet-mexyl") (S2-1), 1,3-dimethyl-but-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxo-prop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), its hydrates and salts, for example its lithium, sodium, potassium, calcium, magnesium, aluminium, iron, ammonium, quaternary ammonium, sulphonium or phosphonium salts, as described in WO-A-2002/34048;

b) compounds of the type of the (5-chloro-8-quinolinoxy) malonic acid ($S2^b$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Compounds of the formula (S3)

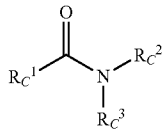

(S3)

where the symbols and indices have the following meanings:

$R_C^1$ is ($C_1$-$C_4$)-alkyl, ($C_1$-$C_4$)-haloalkyl, ($C_2$-$C_4$)-alkenyl, ($C_2$-$C_4$)-haloalkenyl, ($C_3$-$C_7$)-cycloalkyl, preferably dichloromethyl;

$R_C^2$, $R_C^3$ are identical or different and are hydrogen, ($C_1$-$C_4$)-alkyl, ($C_2$-$C_4$)-alkenyl, ($C_2$-$C_4$)-alkynyl, ($C_1$-$C_4$)-haloalkyl, ($C_2$-$C_4$)-haloalkenyl, ($C_1$-$C_4$)-alkylcarbamoyl-($C_1$-$C_4$)-alkyl, ($C_2$-$C_4$)-alkenylcarbamoyl-($C_1$-$C_4$)-alkyl, ($C_1$-$C_4$)-alkoxy-($C_1$-$C_4$)-alkyl, dioxolanyl-($C_1$-$C_4$)-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:

active compounds of the type of the dichloroacetamides which are frequently used as pre-emergence safeners (soil-acting safeners), such as, for example, "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl] dichloroacetamide) from PPG Industries (S3-5), "DKA-24" (N-allyl-N-[(allylaminocarbonyl)methyl] dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TRI-Chemical RT (S3-8)

"diclonon" (dicyclonon) or "BAS145138" or "LAB145138" (S3-9) (3-dichloroacetyl-2,5,5-trimethyl-1,3-diazabicyclo[4.3.0]nonane) from BASF, "furilazole" or "MON 13900" ((RS)-3-dichloroacetyl-5-(2-furyl)-2,2-dimethyloxazolidine) (S3-10) and also its (R)-isomer (S3-11).

S4) N-Acylsulphonamides of the formula (S4) and their salts

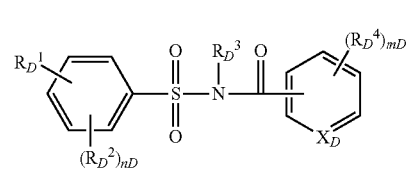

(S4)

where the symbols and indices have the following meanings:

$X_D$ is CH or N;

$R_D^1$ is CO—$NR_D^5R_D^6$ or NHCO—$R_D^7$;

$R_D^2$ is halogen, ($C_1$-$C_4$)-haloalkyl, ($C_1$-$C_4$)-haloalkoxy, nitro, ($C_1$-$C_4$)-alkyl, ($C_1$-$C_4$)-alkoxy, ($C_1$-$C_4$)-alkylsulphonyl, ($C_1$-$C_4$)-alkoxycarbonyl or ($C_1$-$C_4$)-alkylcarbonyl;

$R_D^3$ is hydrogen, ($C_1$-$C_4$)-alkyl, ($C_2$-$C_4$)-alkenyl or ($C_2$-$C_4$)-alkynyl;

$R_D^4$ is halogen, nitro, ($C_1$-$C_4$)-alkyl, ($C_1$-$C_4$)-haloalkyl, ($C_1$-$C_4$)-haloalkoxy, ($C_3$-$C_6$)-cycloalkyl, phenyl, ($C_1$-$C_4$)-alkoxy, cyano, ($C_1$-$C_4$)-alkylthio, ($C_1$-$C_4$)-alkylsulphinyl, ($C_1$-$C_4$)-alkylsulphonyl, ($C_1$-$C_4$)-alkoxycarbonyl or ($C_1$-$C_4$)-alkylcarbonyl;

$R_D^5$ is hydrogen, ($C_1$-$C_6$)-alkyl, ($C_3$-$C_6$)-cycloalkyl, ($C_2$-$C_6$)-alkenyl, ($C_2$-$C_6$)-alkynyl, ($C_5$-$C_6$)-cycloalkenyl, phenyl or 3- to 6-membered heterocyclyl which contains $v_D$ heteroatoms from the group consisting of nitrogen, oxygen and sulphur, where the seven last-mentioned radicals are substituted by $v_D$ substituents from the group consisting of halogen, ($C_1$-$C_6$)-alkoxy, ($C_1$-$C_6$)-haloalkoxy, ($C_1$-$C_2$)-alkylsulphinyl, ($C_1$-$C_2$)-alkylsulphonyl, ($C_3$-$C_6$)-cycloalkyl, ($C_1$-$C_4$)-alkoxycarbonyl, ($C_1$-$C_4$)-alkylcarbonyl and phenyl and, in the case of cyclic radicals, also ($C_1$-$C_4$)-alkyl and ($C_1$-$C_4$)-haloalkyl;

$R_D^6$ is hydrogen, ($C_1$-$C_6$)-alkyl, ($C_2$-$C_6$)-alkenyl or ($C_2$-$C_6$)-alkynyl, where the three last-mentioned radicals are substituted by $v_D$ radicals from the group consisting of halogen, hydroxy, ($C_1$-$C_4$)-alkyl, ($C_1$-$C_4$)-alkoxy and ($C_1$-$C_4$)-alkylthio, or $R_D^5$ and $R_D^6$ together with the nitrogen atom carrying them form a pyrrolidinyl or piperidinyl radical;

$R_D^7$ is hydrogen, ($C_1$-$C_4$)-alkylamino, di-($C_1$-$C_4$)-alkylamino, ($C_1$-$C_6$)-alkyl, ($C_3$-$C_6$)-cycloalkyl, where the 2 last-mentioned radicals are substituted by $v_D$ substituents from the group consisting of halogen, ($C_1$-$C_4$)- alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;

$n_D$ is 0, 1 or 2;

$m_D$ is 1 or 2;

$v_D$ is 0, 1, 2 or 3;

from among these, preference is given to compounds of the type of the N-acylsulphonamides, for example of the formula (S4$^a$) below, which are known, for example, from WO-A-97/4subchamber16

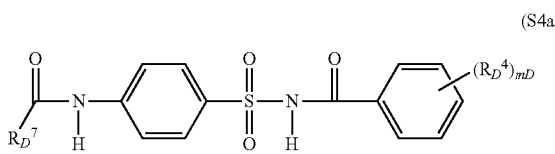

(S4a)

in which $R_D^7$ is $(C_1-C_6)$-alkyl, $(C_3-C_6)$-cycloalkyl, where the 2 last-mentioned radicals are substituted by $v_D$ substituents from the group consisting of halogen, $(C_1-C_4)$-alkoxy, halo-$(C_1-C_6)$-alkoxy and $(C_1-C_4)$-alkylthio and, in the case of cyclic radicals, also $(C_1-C_4)$-alkyl and $(C_1-C_4)$-haloalkyl;

$R_D^4$ is halogen, $(C_1-C_4)$-alkyl, $(C_1-C_4)$-alkoxy, $CF_3$;

$m_D$ 1 or 2;

$v_D$ is 0, 1, 2 or 3;

and also acylsulphamoylbenzamides, for example of the formula (S4$^b$) below, which are known, for example, from WO-A-99/16744,

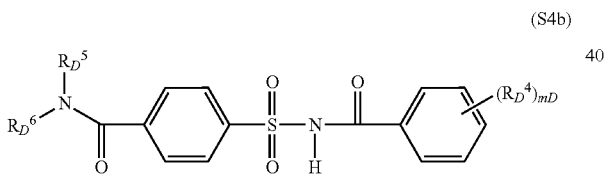

(S4b)

in which $R_D^5$, $R_D^6$ independently of one another are hydrogen, $(C_1-C_6)$-alkyl, $(C_3-C_6)$-cycloalkyl, $(C_3-C_6)$-alkenyl, $(C_3-C_6)$-alkynyl, $R_D^4$ is halogen, $(C_1-C_4)$-alkyl, $(C_1-C_4)$-haloalkyl or $(C_1-C_4)$-alkoxy and $m_D$ is 1 or 2, for example those in which $R_D^5$=cyclopropyl and $(R_D^4)$=2-OMe ("cyprosulphamide", S4-1), $R_D^5$=cyclopropyl and $(R_D^4)$=5-Cl-2-OMe (S4-2), $R_D^5$=ethyl and $(R_D^4)$=2-OMe (S4-3), $R_D^5$=isopropyl and $(R_D^4)$=5-$C_{1-2}$-OMe (S4-4) and $R_D^5$=isopropyl and $(R_D^4)$=2-OMe (S4-5)

and also compounds of the type of the N-acylsulphamoylphenylureas of the formula (S4$^c$), which are known, for example, from EP-A-365484,

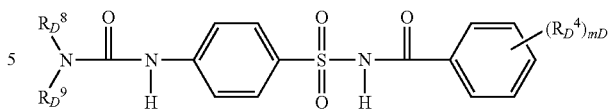

(S4c)

in which $R_D^8$ and $R_D^9$ independently of one another are hydrogen, $(C_1-C_8)$-alkyl, $(C_3-C_8)$-cycloalkyl, $(C_3-C_6)$-alkenyl, $(C_3-C_6)$-alkynyl, $R_D^4$ is halogen, $(C_1-C_4)$-alkyl, $(C_1-C_4)$-alkoxy, $CF_3$, $m_D$ is 1 or 2;

for example

1-[4-(N-2-methoxybenzoylsulphamoyl)phenyl]-3-methylurea,

1-[4-(N-2-methoxybenzoylsulphamoyl)phenyl]-3,3-dimethylurea,

1-[4-(N-4,5-dimethylbenzoylsulphamoyl)phenyl]-3-methylurea.

S5) Active compounds from the class of the hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 1,2-dihydro-2-oxo-6-trifluoromethylpyridine-3-carboxamide, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-[2-(diethylamino)ethyl]-6,7-dimethyl-3-thiophen-2-ylquinoxalin-2(1H)-one, 1-(2-methylsulphonylaminoethyl)-3-(2-thienyl)-1,2-dihydroquinoxalin-2-one, as described in WO-A-2005/112630.

S7) Compounds of the formula (S7), as described in WO-A-1998/38856,

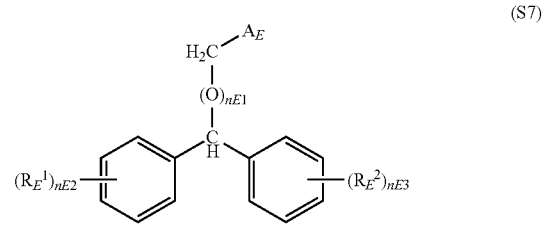

(S7)

where the symbols and indices have the following meanings:

$R_E^1$, $R_E^2$ independently of one another are halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;

$A_E$ is $COOR_E^3$ or $COSR_E^4$ $R_E^3$, $R_E^4$ independently of one another are hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl or alkylammonium, $n_E$ is 0 or 1;

$n_E^2$, $n_E^3$ independently of one another are 0, 1 or 2, preferably:
diphenylmethoxyacetic acid,
ethyl diphenylmethoxyacetate,
methyl diphenylmethoxyacetate (CAS Reg. No.: 41858-19-9) (S7-1).
S8) Compounds of the formula (S8), as described in WO-A-98/27049,

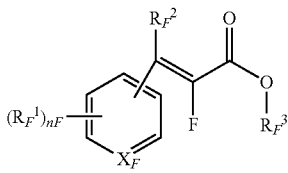

(S8)

in which
$X_F$ is CH or N,
$n_F$ is, if $X_F$=N, an integer from 0 to 4 and is, if $X_F$=CH, an integer from 0 to 5,
$R_F^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulphonyl, $(C_1-C_4)$-alkoxycarbonyl, optionally substituted phenyl, optionally substituted phenoxy,
$R_F^2$ is hydrogen or $(C_1-C_4)$-alkyl,
$R_F^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or more, preferably by up to three, identical or different radicals from the group consisting of halogen and alkoxy; or salts thereof,
preferably compounds in which
$X_F$ is CH,
$n_F$ is an integer from 0 to 2,
$R_F^1$ is halogen, $(C_1-C_4)$-alkyl, $(C_1-C_4)$-haloalkyl, $(C_1-C_4)$-alkoxy, $(C_1-C_4)$-haloalkoxy,
$R_F^2$ is hydrogen or $(C_1-C_4)$-alkyl,
$R_F^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or more, preferably by up to three, identical or different radicals from the group consisting of halogen and alkoxy;
or salts thereof,
S9) Active compounds from the class of the 3-(5-tetrazolylcarbonyl)-2-quinolones (S9), for example
1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No.: 95855-00-8), as described in WO-A-1999/000020.
S10) Compounds of the formula (S10$^a$) or (S10$^b$) as described in WO-A-2007/023719 and WO-A-2007/023764

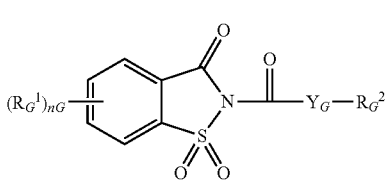

(S10a)

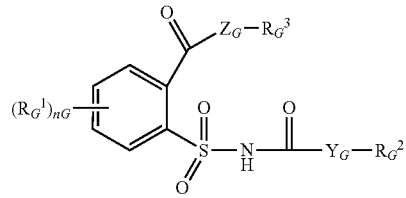

(S10b)

in which
$R_G^1$ is halogen, $(C_1-C_4)$-alkyl, methoxy, nitro, cyano, $CF_3$, $OCF_3$
$Y_G$, $Z_G$ independently of one another are O or S,
$n_G$ is an integer from 0 to 4,
$R_G^2$ is $(C_1-C_{16})$-alkyl, $(C_2-C_6)$-alkenyl, $(C_3-C_6)$-cycloalkyl, aryl; benzyl, halobenzyl,
$R_G^3$ is hydrogen or $(C_1-C_6)$-alkyl.
S11) Active compounds of the type of the oxyimino compounds (S11), which are known as seed dressings, such as, for example, "oxabetrinil" ((Z)-1,3-dioxolan2-ylmethoxyimino(phenyl)acetonitrile) (S11-1), which is known as seed dressing safener for millet against metolachlor damage,
"fluxofenim" (1-(4-chlorophenyl)-2,2,2-trifluoro-1-ethanone O-(1,3-dioxolan-2-ylmethyl)oxime) (S11-2), which is known as seed dressing safener for millet against metolachlor damage, and
"cyometrinil" or "CGA-43089" ((Z)-cyanomethoxyimino (phenyl)acetonitrile) (S11-3), which is known as seed dressing safener for millet against metolachlor damage.
S12) Active compounds from the class of the isothiochromanones (S12), such as, for example, methyl[(3-oxo-1H-2-benzothiopyran-4(3H)-ylidene)methoxy]acetate (CAS Reg. No.: 205121-04-6) (S12-1) and related compounds from WO-A-1998/13361.
S13) One or more compounds from group (S13):
"naphthalic anhydride" (1,8-naphthalenedicarboxylic anhydride) (S13-1), which is known as seed dressing safener for corn against thiocarbamate herbicide damage,
"fenclorim" (4,6-dichloro-2-phenylpyrimidine) (S13-2), which is known as safener for pretilachlor in sown rice,
"flurazole" (benzyl 2-chloro-4-trifluoromethyl-1,3-thiazole-5-carboxylate) (S13-3), which is known as seed dressing safener for millet against alachlor and metolachlor damage,
"CL-304415" (CAS Reg. No.: 31541-57-8) (4-carboxy-3,4-dihydro-2H-1-benzopyran-4-acetic acid) (S13-4) from American Cyanamid, which is known as safener for corn against imidazolinone damage,
"MG-191" (CAS Reg. No.: 96420-72-3) (2-dichloromethyl-2-methyl-1,3-dioxolane) (S13-5) from Nitrokemia, which is known as safener for corn,
"MG-838" (CAS Reg. No.: 133993-74-5) (2-propenyl 1-oxa-4-azaspiro[4.5]decane-4-carbodithioate) (S13-6) from Nitrokemia,
"disulfoton" (O,O-diethyl S-2-ethylthioethyl phosphorodithioate) (S13-7),
"dietholate" (O,O-diethyl O-phenyl phosphorothioate) (S13-8),
"mephenate" (4-chlorophenyl methylcarbamate) (S13-9).
S14) Active compounds which, besides a herbicidal effect against harmful plants, also have a safener effect on crop plants such as rice, such as, for example, "dimepiperate" or "MY-93" (S-1-methyl-1-phenylethyl piperidine-1-carbothioate), which is known as safener for rice against molinate herbicide damage, "daimuron" or "SK 23" (1-(1-methyl-1-phenylethyl)-3-p-tolylurea), which is known as safener for rice against imazosulphuron herbicide damage, "cumyluron"="JC-940" (3-(2-chlorophenylmethyl)-1-(1-methyl-1-phenyl-ethyl)urea, see JP-A-60087254), which is known as safener for rice against some herbicide damage, "methoxyphenone" or "NK 049" (3,3'-dimethyl-4-methoxybenzophenone), which is known as safener for rice against some herbicide damage, "CSB" (1-bromo-4-(chloromethylsulphonyl)benzene) from Kumiai, (CAS Reg. No. 54091-06-4), which is known as safener against some herbicide damage in rice.

S15) Compounds of the formula (S15) or tautomers thereof

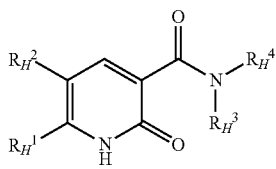

(S15)

as described in WO-A-2008/131861 and WO-A-2008/131860
in which
$R_H^1$ is a $(C_1-C_6)$-haloalkyl radical and
$R_H^2$ is hydrogen or halogen and
$R_H^3$, $R_H^4$ independently of one another are hydrogen, $(C_1-C_{16})$-alkyl, $(C_2-C_{16})$-alkenyl or $(C_2-C_{16})$-alkynyl,
where each of the 3 last mentioned radicals is unsubstituted or substituted by one or more radicals from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di$[(C_1-C_4)$-alkyl]amino, $[(C_1-C_4)$-alkoxy]carbonyl, $[(C_1-C_4)$-haloalkoxy]carbonyl, unsubstituted or substituted $(C_3-C_6)$-cycloalkyl, unsubstituted or substituted phenyl and unsubstituted or substituted heterocyclyl,
or $(C_3-C_6)$-cycloalkyl, $(C_4-C_6)$-cycloalkenyl, $(C_3-C_6)$-cycloalkyl which is fused at one side of the ring to a 4- to 6-membered saturated or unsaturated carbocyclic ring, or $(C_4-C_6)$-cycloalkenyl which is fused at one side of the ring to a 4- to 6-membered saturated or unsaturated carbocyclic ring,
where each of the 4 last mentioned radicals is unsubstituted or substituted by one or more radicals from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di$[(C_1-C_4)$-alkyl]amino, $[(C_1-C_4)$-alkoxy]carbonyl, $[(C_1-C_4)$-haloalkoxy]carbonyl, unsubstituted or substituted $(C_3-C_6)$-cycloalkyl, unsubstituted or substituted phenyl and unsubstituted or substituted heterocyclyl,
or
$R_H^3$ is $(C_1-C_4)$-alkoxy, $(C_2-C_4)$-alkenyloxy, $(C_2-C_6)$-alkynyloxy or $(C_2-C_4)$-haloalkoxy and
$R_H^4$ is hydrogen or $(C_1-C_4)$-alkyl or
$R_H^3$ and $R_H^4$ together with the directly attached nitrogen atom are a 4- to 8-membered heterocyclic ring which, in addition to the nitrogen atom, may also contain further hetero ring atoms, preferably up to two further hetero ring atoms from the group consisting of N, O and S, and which is unsubstituted or substituted by one or more radicals from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio.

S16) Active compounds which are primarily used as herbicides, but also have safener effect on crop plants, for example
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

Most preferred crop plant compatibility-improving compounds are cloquintocet-mexyl, fenchlorazole-ethyl, isoxadifen-ethyl, mefenpyr-diethyl, fenclorim, cumyluron, S4-1 and S4-5, and particular emphasis is given to cloquintocet-mexyl and mefenpyr-diethyl.

It has now surprisingly been found that the above-defined active compound combinations of compounds of the general formula (I) and safeners (antidotes) from group (b') set out above combine very good compatibility with useful plants with a particularly high herbicidal activity and can be used in various crops, in particular in cereals (especially wheat), but also in soya beans, potatoes, maize and rice, for the selective control of weeds.

In this context, it is considered surprising that, from a multiplicity of known safeners or antidotes capable of antagonizing the damaging effect of a herbicidal crop plant, it is specifically the compounds of group (b') set out above which are suitable for compensating—almost completely—the damaging effect of compounds of the formula (I) on the crop plants, without at the same time having any substantial adverse effect on the herbicidal activity against the weeds.

Emphasis may be given here to the particularly advantageous effect of the preferred and most preferred combination partners from group (b'), particularly with regard to the sparing of cereal plants, such as, for example, wheat, barley and rye, but also maize and rice, as crop plants.

According to the invention, the preparation of the compounds of the formula (I) can be carried out by processes A to H.

Using, for example, according to process (A) methyl-2-[(2,6-diethyl-4-methylphenyl)acetyl]-4-(1,3-dioxolan-2-yl)cyclopentane carboxylate, the course of the process according to the invention can be represented by the reaction scheme below:

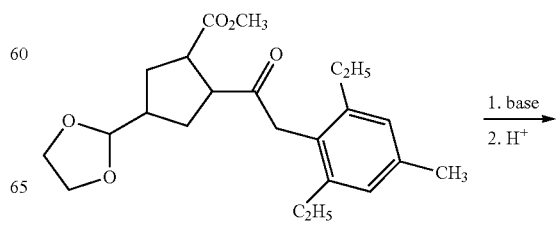

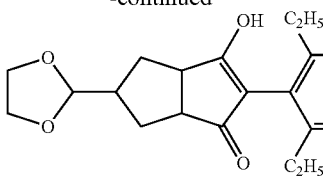

Using, for example, according to process (B) 2-(2,6-diethyl-4-methylphenyl)-5-(1,3-dioxolan-2-yl)-3-hydroxy-4,5,6,6a-tetrahydropentalen-1(3aH)-one and pivaloyl chloride as starting materials, the course of the process according to the invention can be represented by the reaction scheme below:

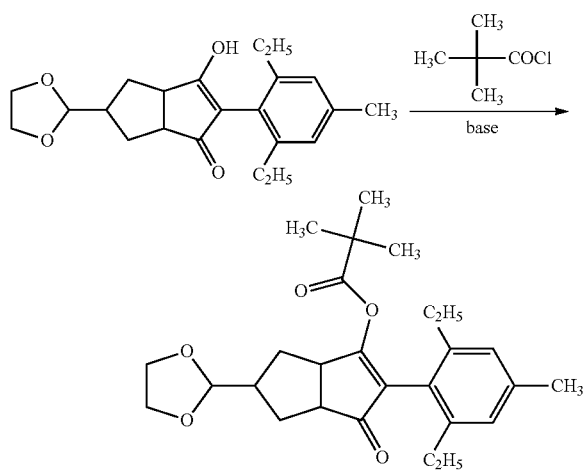

Using, for example, according to process (B) 2-(2,6-diethyl-4-methylphenyl)-5-(1,3-dioxolan-2-yl)-3-hydroxy-4,5,6,6a-tetrahydropentalen-1(3aH)-one and acetic anhydride as starting materials, the course of the process according to the invention can be represented by the reaction scheme below:

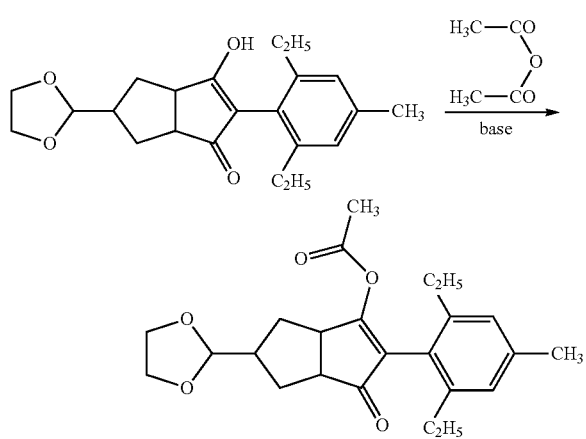

Using, for example, according to process (C) 2-(2,6-diethyl-4-methylphenyl)-5-(1,3-dioxolan-2-yl)-3-hydroxy-4,5,6,6a-tetrahydropentalen-1(3aH)-one and ethyl chloroformate as starting materials, the course of the process according to the invention can be represented by the reaction scheme below:

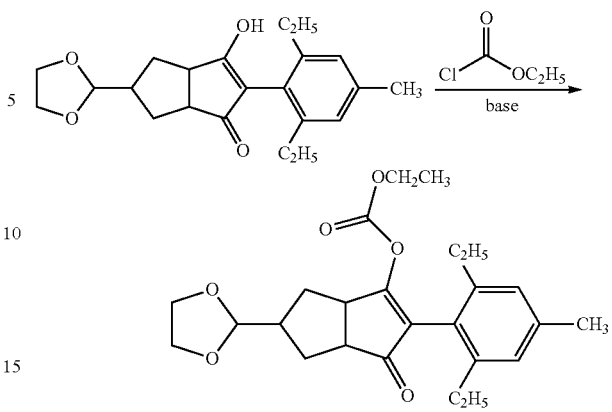

Using, for example, according to process (D) 2-(2,6-diethyl-4-methylphenyl)-5-(1,3-dioxolan-2-yl)-3-hydroxy-4,5,6,6a-tetrahydropentalen-1(3aH)-one and methyl chloromonothioformate as starting materials, the course of the process according to the invention can be represented by the reaction scheme below:

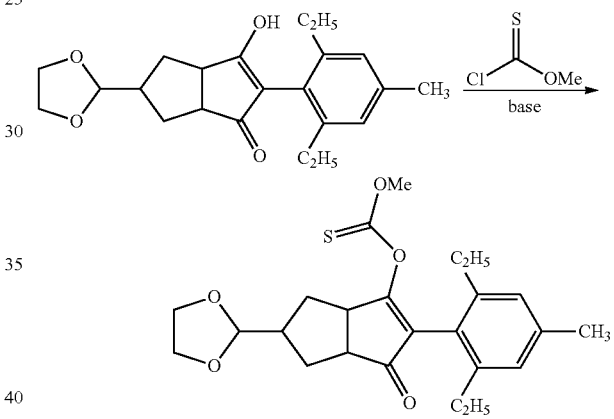

Using, for example, according to process (E) 5'-(2,6-diethyl-4-methylphenyl)-6'-hydroxy-2,2-dimethyl-1',3',3a',6a'-tetrahydro-4'H-spiro[1,3-dioxolan-4,2'-pentalen]-4'-one and methanesulphonyl chloride as starting materials, the course of the reaction can be represented by the reaction scheme below:

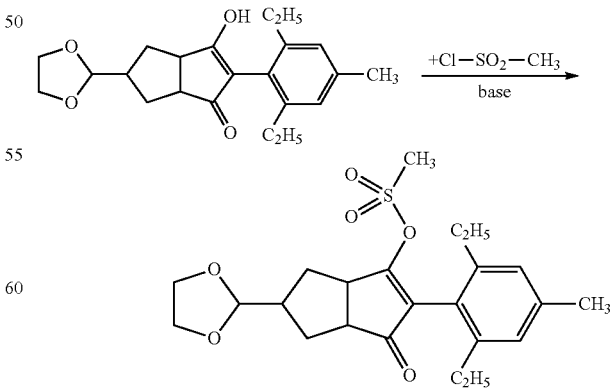

Using, for example, according to process (F) 2-(2,6-diethyl-4-methylphenyl)-5-(1,3-dioxolan-2-yl)-3-hydroxy-4, 5,6,6a-tetrahydropentalen-1 (3aH)-one and 2,2,2-trifluoroethylmethanethiophosphonyl chloride as starting materials, the course of the reaction can be represented by the reaction scheme below:

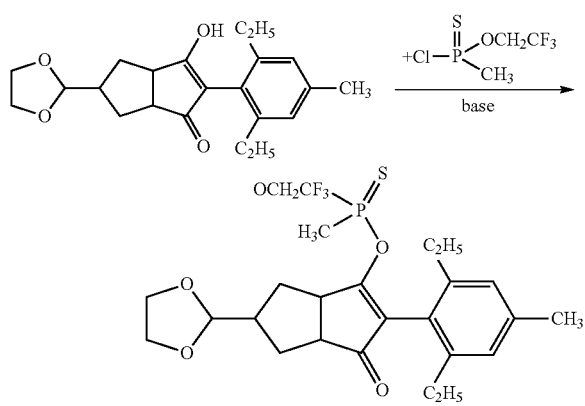

Using, for example, according to process (G) 2-(2,6-diethyl-4-methylphenyl)-5-(1,3-dioxolan-2-yl)-3-hydroxy-4,5,6,6a-tetrahydropentalen-1(3aH)-one and NaOH as components, the course of the process according to the invention can be represented by the reaction scheme below:

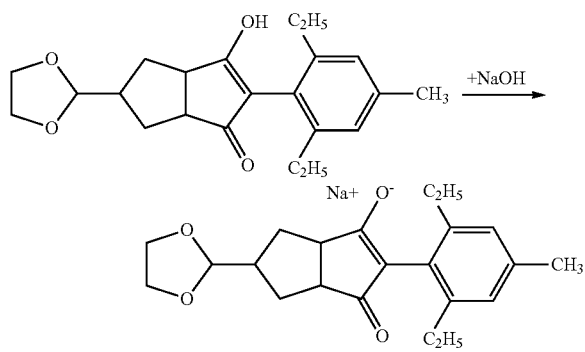

Using, for example, according to process (H), variant a, 2-(2,6-diethyl-4-methylphenyl)-5-(1,3-dioxolan-2-yl)-3-hydroxy-4,5,6,6a-tetrahydropentalen-1(3aH)-one and ethyl isocyanate as starting materials, the course of the reaction can be represented by the reaction scheme below:

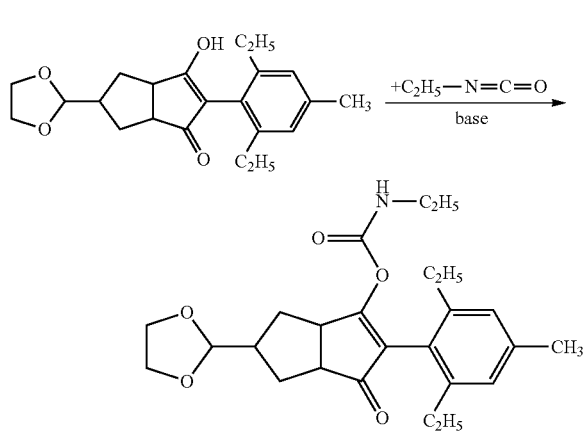

Using, for example, according to process (H), variant B, 2-(2,6-diethyl-4-methylphenyl)-5-(1,3-dioxolan-2-yl)-3-hydroxy-4,5,6,6a-tetrahydropentalen-1 (3aH)-one and dimethylcarbamoyl chloride as starting materials, the course of the reaction may be represented by the scheme below:

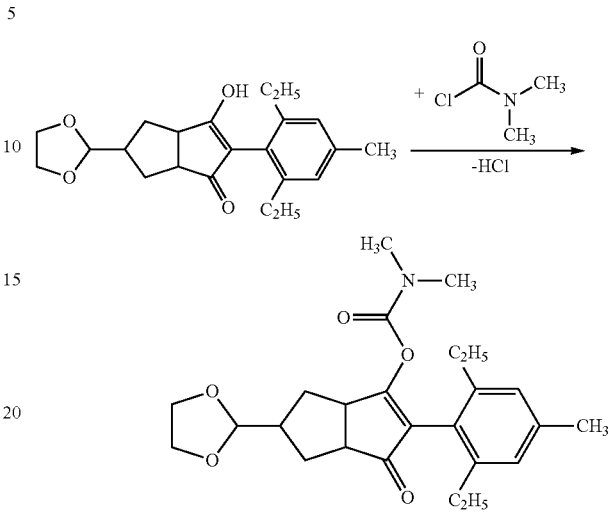

The compounds, required as starting material in process (A) according to the invention, of the formula (II)

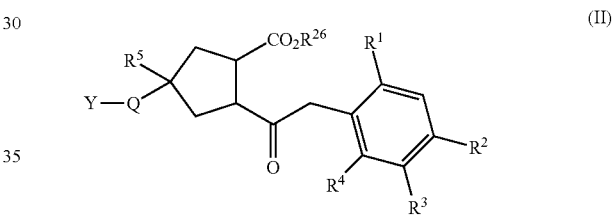

in which

Q, Y, $R^1$, $R^2$, $R^3$, $R^4$ and $R^5$ have the meaning given above, and $R^{26}$ represents alkyl (in particular $C_1$-$C_8$-alkyl)

are novel. They can be prepared by methods known in principle by esterifying 5-aryl-4-ketocarboxylic acids of the formula (XIII)

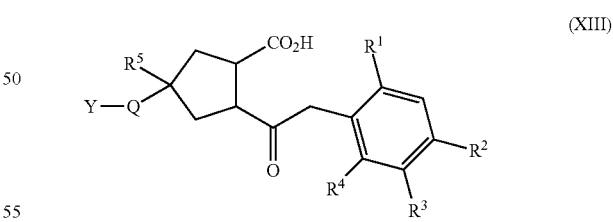

in which

Q, Y, $R^1$, $R^2$, $R^3$, $R^4$ and $R^5$ have the meaning given above in a conventional manner (cf., for example, Organikum, 15th Edition, Berlin, 1977, page 499 or Preparation Example).

Compounds of the formula (XIII) are likewise novel, they can be prepared by methods known in principle (WO 07/080,066, WO 96/01 798, WO 97/14667, WO 98/39281, WO 01/74770), for example, by decarboxylating 2-phenyl-3-oxoadipic esters of the formula (XIV)

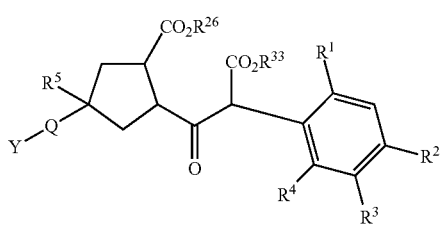
(XIV)

in which Q, Y, $R^1$, $R^2$, $R^3$, $R^4$ and $R^5 R^{26}$ have the meaning given above and $R^{26}$ represents alkyl (in particular $C_1$-$C_8$-alkyl) or, if the preparation uses the anhydrides of the formula (XVI), represents hydrogen, $R^{33}$ represents alkyl (in particular $C_1$-$C_8$-alkyl), if appropriate in the presence of a diluent and if appropriate in the presence of a base or acid according to conventional methods (cf., for example, Organikum, 15th Edition, Berlin, 1977, pages 519-521).

The compounds of the formula (XIV) are likewise novel in principle and can be prepared in accordance with known methods. The compounds of the formula (XIV) are obtained, for example, by reacting dicarboxylic semiester chlorides of the formula (XV)

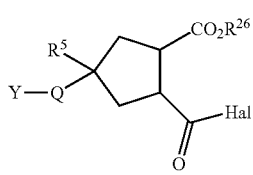
(XV)

in which
Q, Y, R and $R^5$ have the meaning given above and
Hal represents chlorine or bromine
or carboxylic anhydrides of the formula (XVI)

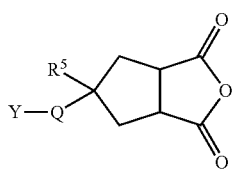
(XVI)

in which
Q, Y and $R^5$ have the meaning given above
with a phenylacetic ester of the formula (XVII)

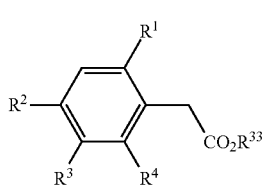
(XVII)

in which
R, $R^1$, $R^2$, $R^3$, $R^4$, $R^5$ and $R^{33}$ have the meaning given above in the presence of a diluent and in the presence of a base (cf., for example, M. S. Chambers, E. J. Thomas, D. J. Williams, J. Chem. Soc. Chem. Commun, (1987), 1228).

A further proven method for preparing the compounds, required as starting materials for process (A), of the formula (II)

in which
Q, Y, $R^1$, $R^2$, $R^3$, $R^4$ and $R^5$ have the meaning given above
is also, for example, the coupling of benzyl zinc compounds of the formula (XVIII)

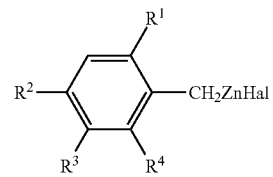
(XVIII)

in which $R^1$, $R^2$, $R^3$ and $R^4$ have the meaning given above and Hal represents a halogen atom, preferably chlorine or bromine, if appropriate in the presence of a catalyst, with a dicarboxylic semiester chloride of the formula (XV) or a carboxylic anhydride of the formula (XVI).

Both the preparation and the reaction of organic zinc compounds with carbonyl chlorides and carboxylic anhydrides are known in principle and can be carried out in close analogy to the processes described in the literature. More details are described, for example, in Chem. Commun 2008, 5824, WO 2007/113294, WO 2010/040460, Tetrahedron Letters 30, 5069-5072 (1989) or Chem. Rev. 1993, 93, 2117-2188.

The acid halides of the formula (III), carboxylic anhydrides of the formula (IV), chloroformic esters or chloroformic thioesters of the formula (V), chloromonothioformic esters or chlorodithioformic esters of the formula (VI), sulphonyl chlorides of the formula (VII), phosphorus compounds of the formula (VIII) and metal hydroxides, metal alkoxides or amines of the formulae (IX) and (X) and isocyanates of the formula (XI) and carbamoyl chlorides of the formula (XII) furthermore required as starting materials for carrying out the processes (B), (C), (D), (E), (F), (G) and (H) according to the invention are generally known compounds of organic of inorganic chemistry.

The compounds of the formulae (XV), (XVI), (XVII) and (XVIII) are known compounds of organic chemistry or known from the patent applications cited at the outset and/or can be prepared in a simple manner by methods known in principle or can be prepared by the methods described in the patent applications cited at the outset.

The process (A) is characterized in that compounds of the formula (II), in which Q, Y, $R^1$, $R^2$, $R^3$, $R^4$ and $R^5$ have the meaning given above are subjected to an intramolecular condensation in the presence of a base.

Suitable for use as diluents in the process (A) according to the invention are all organic solvents which are inert towards the reaction participants. Preference is given to using hydrocarbons, such as toluene and xylene, furthermore ethers, such as bibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol, tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which may also be used in the presence of phase-transfer catalysts, such as, for example, triethylbenzylammonium chloride molar amounts. However, it is also possible to use a relatively large excess (up to 3 mol) of one component or the other.

The process (B-α) is characterized in that compounds of the formula (I-a) are in each case reacted with carbonyl halides of the formula (III), if appropriate in the presence of a diluent and if appropriate in the presence of an acid binder.

Suitable for use as diluents in the process (B-α) according to the invention are all solvents which are inert towards the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholan. If the acid halide is sufficiently stable to hydrolysis, the reaction can also be carried out in the presence of water.

Suitable acid binders for the reaction according to process (B-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig-Base and N,N-dimethylaniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

The reaction temperatures in the process (B-α) according to the invention can be varied within a relatively wide range. In general, the process is carried out at temperatures between −20° C. and +150° C., preferably between 0° C. and 100° C.

When carrying out the process (B-α) according to the invention, the starting materials of the formula (I-a) and the carbonyl halide of the formula (III) are generally each employed in approximately equivalent amounts. However, it is also possible to use a relatively large excess (up to 5 mol) of the carbonyl halide. Work-up is carried out by customary methods.

The process (B-β) is characterized in that compounds of the formula (I-a) are reacted with carboxylic anhydrides of the formula (IV), if appropriate in the presence of a diluent and if appropriate in the presence of an acid binder.

Suitable diluents for use in the process (B-β) according to the invention are, preferably, the diluents which are also preferred when using acid halides. Besides this a carboxylic anhydride used in excess may simultaneously act as diluent.

Suitable acid binders, which are added, if appropriate, for process (B-β) are, preferably, the acid binders which are also preferred when using acid halides.

The reaction temperatures in the process (B-β) according to the invention may be varied within a relatively wide range. In general, the process is carried out at temperatures between −20° C. and +150° C., preferably between 0° C. and 100° C.

When carrying out the process (B-β) according to the invention, the starting materials of the formula (I-a) and the carboxylic anhydride of the formula (IV) are generally each employed in approximately equivalent amounts. However, it is also possible to use a relatively large excess (up to 5 mol) of carboxylic anhydride. Work-up is carried out by customary methods.

In general, diluent and excess carboxylic anhydride and the carboxylic acid formed are removed by distillation or by washing with an organic solvent or with water.

The process (C) is characterized in that compounds of the formula (I-a) are in each case reacted with chloroformic esters or chloroformic thio esters of the formula (V), if appropriate in the presence of a diluent and if appropriate in the presence of an acid binder.

Suitable acid binders for the reaction according to the process (C) according to the invention are all customary acid acceptors. Preference is given to use tertiary amines, such as triethylamine, pyrridine, DABCO, DBU, DBA, Hünig-Base and N,N-dimethylaniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

Suitable diluents for use in the process (C) according to the invention are all solvents which are inert towards the chloroformic esters or chloroformic thio esters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholan.

When carrying out the process (C) according to the invention, the reaction temperatures can be varied within a relatively wide range. If the process is carried out in the presence of a diluent and an acid binder, the reaction temperatures are generally between −20° C. and +100° C., preferably between 0° C. and 50° C.

The process (C) according to the invention is generally carried out under atmospheric pressure.

When carrying out the process (C) according to the invention, the starting materials of the formula (I-a) and the appropriate chloroformic ester or chloroformic thio ester of the formula (V) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (D) according to the invention is characterized in that compounds of the formula (I-a) are in each case reacted with compounds of the formula (VI) in the presence of a diluent and, if appropriate, in the presence of an acid binder.

In preparation process (D), about one mol of chloromonothioformic ester or chlorodithioformic ester of the formula (VI) is employed per mole of the starting material of the formula (I-a) at from 0 to 120° C., preferably from 20 to 60° C.

Suitable diluents which are added, if appropriate, are all inert polar organic solvents, such as ethers, amides, sulphones, sulphoxides, and also halogenated alkanes.

Preference is given to using dimethyl sulphoxide, tetrahydrofuran, dimethylformamide or methylene chloride.

If, in a preferred embodiment, the enolate salt of the compounds (1-a) is prepared by addition of strong deprotonating agents, such as, for example, sodium hydride or potassium tert-butoxide, the further addition of acid binders may be dispensed with.

If acid binders are used, these are customary inorganic or organic bases; sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods.

The process (E) according to the invention is characterized in that compounds of the formula (I-a) are in each case reacted with sulphonyl chlorides of the formula (VII), if appropriate in the presence of a diluent and if appropriate in the presence of an acid binder.

In preparation process (E), about one mol of sulphonyl chloride of the formula (VII) is reacted per mole of the starting material of the formula (I-a) at from −20 to 150° C., preferably from 20 to 70° C.

Suitable diluents which are added, if appropriate, are all inert polar organic solvents, such as ethers, amides, nitriles, sulphones, sulphoxides or halogenated hydrocarbons, such as methylene chloride.

Preference is given to using dimethyl sulphoxide, tetrahydrofuran, dimethylformamide, methylene chloride.

If, in a preferred embodiment, the enolate salt of the compounds (1-a) is prepared by addition of strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, pyridine and triethylamine.

The reaction can be carried out at atmospheric pressure or under elevated pressure and is preferably carried out at atmospheric pressure. Work-up is carried out by customary methods.

The process (F) according to the invention is characterized in that compounds of the formula (I-a) are in each case reacted with phosphorus compounds of the formula (VIII), if appropriate in the presence of a diluent and if appropriate in the presence of an acid binder.

In preparation process (F), to obtain compounds of the formula (I-e), from 1 to 2, preferably from 1 to 1.3, mol of the phosphorus compound of the formula (VIII) are reacted per mole of the compounds of the formula (I-a), at temperatures between −40° C. and 150° C., preferably between −10 and 110° C.

Suitable diluents which are added, if appropriate, are all inert polar organic solvents, such as ethers, amides, nitriles, alcohols, sulphides, sulphones, sulphoxides, etc.

Preference is given to using acetonitrile, dimethyl sulphoxide, tetrahydrofuran, dimethylformamide, methylene chloride.

Suitable acid binders which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods of organic chemistry. The arising end products are preferably purified by crystallization, chromatographic purification or "incipient distillation" i.e. removal of the volatile components under reduced pressure.

The process (G) is characterized in that compounds of the formula (I-a) are reacted with metal hydroxides or metal alkoxides of the formula (IX) or amines of the formula (X), if appropriate in the presence of a diluent.

Suitable diluents for use in the process (G) according to the invention are, preferably, ethers, such as tetrahydrofuran, dioxane, diethyl ether, or else alcohols, such as methanol, ethanol, isopropanol, and also water.

The process (G) according to the invention is generally carried out under atmospheric pressure.

The reaction temperatures are generally between −20° C. and 100° C., preferably between 0° C. and 50° C.

The process (H) according to the invention is characterized in that compounds of the formula (I-a) are in each case reacted with (H-α) compounds of the formula (XI), if appropriate in the presence of a diluent and if appropriate in the presence of a catalyst, or (H-β) with compounds of the formula (XII), if appropriate in the presence of a diluent and if appropriate in the presence of an acid binder.

In preparation process (H-α), about 1 mol of isocyanate of the formula (XI) is reacted per mole of starting material of the formula (I-a), at from 0 to 100° C., preferably from 20 to 50° C.

Suitable diluents which are added, if appropriate, are all inert organic solvents, such as ethers, amides, nitrides, sulphones, sulphoxides.

If appropriate, catalysts may be added to accelerate the reaction. Suitable for use as catalysts are, very advantageously, organotin compounds, such as, for example dibutyl tin dilaurate. The reaction is preferably carried out at atmospheric pressure.

In preparation process (H-β), about 1 mol of carbamoyl chloride of the formula (XII) is reacted per mole of starting material of the formula (I-a), at from −20 to 150° C., preferably at from 0 to 70° C.

Suitable diluents which are added, if appropriate, are all inert polar organic solvents, such as ethers, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compound of the formula (I-a) is prepared by addition of strong deprotonating agents (such as, for example, sodium hydride or potassium tert-butoxide), the further addition of acid binders may be dispensed with.

If acid binders are used, then customary inorganic or organic bases are suitable, for example sodium hydroxide, sodium carbonate, potassium carbonate, triethylamine or pyridine.

The reaction can be carried at an atmospheric pressure or under elevated pressure and is preferably carried out at atmospheric pressure. Work-up is carried out by customary methods.

In the literature it has already been described how the action of various active compounds can be boosted by addition of ammonium salts. The salts in question, however, are detersive salts (for example WO 95/017817) or salts which have relatively long alkyl substituents and/or aryl substituents and which have a permeabilizing action or which increase the active compound's solubility (for example EP-A 0 453 086, EP-A 0 664 081, FR-A 2 600 494, U.S. Pat. No. 4,844,734, U.S. Pat. No. 5,462,912, U.S. Pat. No. 5,538,937, US-A 03/0224939, US-A 05/0009880, US-A 05/0096386). Moreover, the prior art describes the action only for particular active compounds and/or particular applications of the corresponding compositions. In other cases, in turn, the salts in question are those of sulphonic acids, where the acids themselves have a paralytic action on insects (U.S. Pat. No. 2,842, 476). A boost to action by ammonium sulphate, for example, is described by way of example for the herbicides glyphosate, phosphinothricin and for phenyl-substituted cyclic ketoenols (U.S. Pat. No. 6,645,914, EP-A2 0 036 106, WO 07/068,427). A corresponding boost of action in the case of insecticides has already been described in WO 07/068,428.

The use of ammonium sulphate as a formulating assistant has also been described for certain active compounds and applications (WO 92/16108), but its purpose therein is to stabilize the formulation, not to boost the action.

It has now been found, surprisingly, that the action of insecticides and/or acaricides and/or herbicides from the class of the phenyl-substituted bicyclooctane-1,3-dione derivatives of the formula (I) can be boosted significantly through the addition of ammonium salts or phosphonium salts to the application solution or through the incorporation of these salts into a formulation comprising phenyl-substituted bicyclooctane-1,3-dione derivatives of the formula (I). The present invention therefore provides for the use of ammonium salts or phosphonium salts for boosting the action of crop protection compositions which comprise as their active compound herbicidal and/or insecticidal and/or acaricidal phenyl-substituted bicyclooctane-1,3-dione derivatives of the formula (I). The invention likewise provides compositions which comprise herbicidal and/or acaricidal and/or insecticidal phenyl-substituted bicyclooctane-1,3-dione derivatives of the formula (I) and action-boosting ammonium salts or phosphonium salts, including not only formulated active compounds but also ready-to-use compositions (spray liquors). The invention further provides, finally, for the use of these compositions for controlling insect pests and/or spider mites and/or unwanted vegetation.

The active compounds can be used in the compositions according to the invention in a broad concentration range. The concentration of the active compounds in the formulation is typically 0.1%-50% by weight.

Formula (III') provides a definition of the ammonium salts and phosphonium salts which, according to the invention, boost the activity of crop protection compositions comprising fatty acid biosynthesis inhibitors

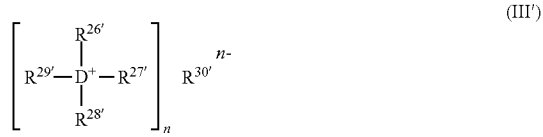

(III')

in which
D represents nitrogen or phosphorus,
D preferably represents nitrogen,
$R^{26'}$, $R^{27'}$, $R^{28'}$ and $R^{29'}$ independently of one another represent hydrogen or in each case optionally substituted $C_1$-$C_8$-alkyl or mono- or polyunsaturated, optionally substituted $C_1$-$C_8$-alkylene, the substituents being selectable from halogen, nitro and cyano,
$R^{26'}$, $R^{27'}$, $R^{28'}$ and $R^{29'}$ independently of one another preferably represent hydrogen or in each case optionally substituted $C_1$-$C_4$-alkyl, the substituents being selectable from halogen, nitro and cyano,
$R^{26'}$, $R^{27'}$, $R^{28'}$ and $R^{29'}$ independently of one another particularly preferably represent hydrogen, methyl, ethyl, n-propyl, isopropyl, n-butyl, isobutyl, sec-butyl or tert-butyl,
$R^{26'}$, $R^{27'}$, $R^{28'}$ and $R^{29'}$ very particularly preferably represent hydrogen,
n represents 1, 2, 3 or 4,
n preferably represents 1 or 2,
$R^{30'}$ represents an organic or inorganic anion,
$R^{30'}$ preferably represents hydrogencarbonate, tetraborate, fluoride, bromide, iodide, chloride, monohydrogenphosphate, dihydrogenphosphate, hydrogensulphate, tartrate, sulphate, nitrate, thiosulphate, thiocyanate, formate, lactate, acetate, propionate, butyrate, pentanoate or oxalate,
$R^{30'}$ particularly preferably represents lactate, sulphate, nitrate, thiosulphate, thiocyanate, oxalate or formate.
$R^{30'}$ very particularly preferably represents sulphate.

The ammonium salts and phosphonium salts of the formula (III') can be used in a broad concentration range to boost the activity of crop protection compositions comprising phenyl-substituted bicyclooctane-1,3-dione derivatives of the formula (I). In general the ammonium salts or phosphonium salts are used in the ready-to-use crop protection composition in a concentration of 0.5 to 80 mmol/l, preferably 0.75 to 37.5 mmol/l, more preferably 1.5 to 25 mmol/l. In the case of a formulated product the ammonium salt and/or phosphonium salt concentration in the formulation is chosen such that it is within these stated general, preferred or particularly preferred ranges after the formulation has been diluted to the desired active compound concentration. The concentration of the salt in the formulation is typically 1%-50% by weight.

In one preferred embodiment of the invention the activity is boosted by adding to the crop protection compositions not only an ammonium salt and/or phosphonium salt but also, additionally, a penetrant. It is considered entirely surprising that even in these cases an even greater boost to activity is observed. The present invention therefore likewise provides for the use of a combination of penetrant and ammonium salts and/or phosphonium salts to boost the activity of crop protection compositions which comprise insecticidal and/or acaricidal and/or herbicidal phenyl-substituted bicyclooctane-1, 3-dione derivatives of the formula (I) as active compound. The invention likewise provides compositions which comprise herbicidal and/or acaricidal and/or insecticidal phenyl-substituted bicyclooctane-1,3-dione derivatives of the formula (I), penetrants and ammonium salts and/or phosphonium salts, including specifically not only formulated active compounds but also ready-to-use compositions (spray liquors). The invention additionally provides, finally, for the use of these compositions for controlling harmful insects and/or spider mites and/or unwanted vegetation.

In the present context, suitable penetrants are all those substances which are usually employed to improve penetration of agrochemically active compounds into plants. In this context, penetrants are defined in that they penetrate from the aqueous spray liquor and/or the spray coating into the cuticles of the plant, thus increasing the mobility of active compounds in the cuticles. The method described in the literature (Baur et al., 1997, *Pesticide Science* 51, 131-152) can be used for determining this property.

Examples of suitable penetrants include alkanol alkoxylates. Penetrants of the invention are alkanol alkoxylates of the formula (IV')

R—O-(-AO)$_v$—R' (IV')

in which
R represents straight-chain or branched alkyl having 4 to 20 carbon atoms,
R' represents hydrogen, methyl, ethyl, n-propyl, isopropyl, n-butyl, isobutyl, tert-butyl, n-pentyl or n-hexyl, AO represents an ethylene oxide radical, a propylene oxide radical, a butylene oxide radical or represents mixtures of ethylene oxide and propylene oxide radicals or butylene oxide radicals, and v represents a number from 2 to 30.

One preferred group of penetrants are alkanol alkoxylates of the formula $$R—O-(-EO—)_n—R' \qquad (IV'\text{-}a)$$

in which
R is as defined above,
R' is as defined above,
EO represents —CH$_2$—CH$_2$—O—, and
n represents a number from 2 to 20.

A further preferred group of penetrants are alkanol alkoxylates of the formula $$R—O—(-EO—)_p—(—PO—)_q—R' \qquad (IV'\text{-}b)$$

in which
R is as defined above,
R' is as defined above,
EO represents —CH$_2$—CH$_2$—O—,
PO represents

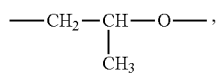

p represents a number from 1 to 10, and
q represents a number from 1 to 10.

A further preferred group of penetrants are alkanol alkoxylates of the formula $$R—O—(—PO—)_r\text{-}(EO—)_s—R' \qquad (IV'\text{-}c)$$

in which
R is as defined above,
R' is as defined above,
EO represents —CH$_2$—CH$_2$—O—,
PO represents

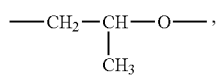

r is a number from 1 to 10, and
s is a number from 1 to 10.

A further preferred group of penetrants are alkanol alkoxylates of the formula $$R—O-(-EO—)_p—(—BO—)_q—R' \qquad (IV'\text{-}d)$$

in which
R and R are as defined above,
EO represents —CH$_2$—CH$_2$—O—,
BO represents

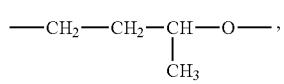

p is a number from 1 to 10 and
q is a number from 1 to 10.

A further preferred group of penetrants are alkanol alkoxylates of the formula $$R—O—(—BO-)_r\text{-}(—EO—)_s—R' \qquad (IV'\text{-}e)$$

in which
R and R' are as defined above,
BO represents

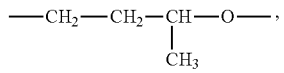

EO represents —CH$_2$—CH$_2$—O—,
r represents a number from 1 to 10 and
s represents a number from 1 to 10.

A further preferred group of penetrants are alkanol alkoxylates of the formula $$CH_3—(CH_2)_t—CH_2—O—(—CH_2—CH_2—O—)_u R' \qquad (IV'\text{-}f)$$

in which
R' is as defined above,
t represents a number from 8 to 13,
u represents a number from 6 to 17.

In the formulae indicated above,
R preferably represents butyl, isobutyl, n-pentyl, isopentyl, neopentyl, n-hexyl, isohexyl, n-octyl, isooctyl, 2-ethylhexyl, nonyl, isononyl, decyl, n-dodecyl, isododecyl, lauryl, myristyl, isotridecyl, trimethylnonyl, palmityl, stearyl or eicosyl.

As an example of an alkanol alkoxylate of the formula (IV'-c) mention may be made of 2-ethylhexyl alkoxylate of the formula

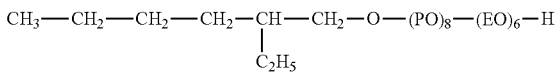

in which
EO represents —CH$_2$—CH$_2$—O—,
PO represents

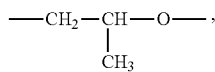

and
the numbers 8 and 6 represent average values.

As an example of an alkanol alkoxylate of the formula (IV'-d) mention may be made of the formula $$CH_3—(CH_2)_{10}—O\text{-}(-EO—)_6—(-BO—)_2—CH_3 \qquad (IV'\text{-}d\text{-}1)$$

in which
EO represents —CH$_2$—CH$_2$—O—,
BO represents

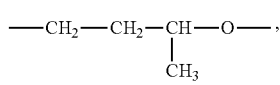

and
the numbers 10, 6 and 2 represent average values.

Particularly preferred alkanol alkoxylates of the formula (IV'-f) are compounds of this formula in which
t represents a number from 9 to 12 and
u represents a number from 7 to 9.

Mention may be made with very particular preference of alkanol alkoxylate of the formula (IV'-f-1)

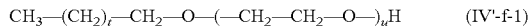  (IV'-f-1)

in which
t represents the average value 10.5 and
u represents the average value 8.4.

A general definition of the alkanol alkoxylates is given by the formulae above. These substances are mixtures of compounds of the stated type with different chain lengths. The indices therefore have average values which may also deviate from whole numbers.

The alkanol alkoxylates of the formulae stated are known and in some cases are available commercially or can be prepared by known methods (cf. WO 98/35 553, WO 00/35 278 and EP-A 0 681 865).

Suitable penetrants also include, for example, substances which promote the availability of the compounds of the formula (I) in the spray coating. These include, for example, mineral or vegetable oils. Suitable oils are all mineral or vegetable oils—modified or otherwise—which can typically be used in agrochemical compositions. Mention may be made by way of example of sunflower oil, rapeseed oil, olive oil, castor oil, colza oil, maize seed oil, cotton seed oil and soya bean oil, or the esters of said oils. Preference is given to rapeseed oil, sunflower oil and their methyl or ethyl esters.

The concentration of penetrant in the compositions of the invention can be varied within a wide range. In the case of a formulated crop protection composition it is in general 1% to 95%, preferably 1% to 55%, more preferably 15%-40% by weight. In the ready-to-use compositions (spray liquors) the concentrations are generally between 0.1 and 10 g/l, preferably between 0.5 and 5 g/l.

Crop protection compositions of the invention may also comprise further components, examples being surfactants and/or dispersing assistants or emulsifiers.

Suitable nonionic surfactants and/or dispersing assistants include all substances of this type that can typically be used in agrochemical compositions. Preferably mention may be made of polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, and copolymers of (meth)acrylic acid and (meth) acrylic esters, and additionally alkyl ethoxylates and alkylaryl ethoxylates, which optionally may be phosphated and optionally may be neutralized with bases, mention being made, by way of example, of sorbitol ethoxylates, and, as well, polyoxyalkylenamine derivatives.

Suitable anionic surfactants include all substances of this type that can typically be used in agrochemical compositions. Preference is given to alkali metal salts and alkaline earth metal salts of alkylsulphonic acids or alkylarylsulphonic acids.

A further preferred group of anionic surfactants and/or dispersing assistants are the following salts that are of low solubility in plant oil: salts of polystyrenesulphonic acids, salts of polyvinylsulphonic acids, salts of naphthalenesulphonic acid-formaldehyde condensation products, salts of condensation products of naphthalenesulphonic acid, phenolsulphonic acid and formaldehyde, and salts of lignosulphonic acid.

Suitable additives which may be included in the formulations of the invention are emulsifiers, foam inhibitors, preservatives, antioxidants, colorants and inert filling materials.

Preferred emulsifiers are ethoxylated nonylphenols, reaction products of alkylphenols with ethylene oxide and/or propylene oxide, ethoxylated arylalkylphenols, and also ethoxylated and propoxylated arylalkylphenols, and also sulphated or phosphated arylalkyl ethoxylates and/or arylalkyl ethoxypropoxylates, mention being made by way of example of sorbitan derivatives, such as polyethylene oxide-sorbitan fatty acid esters, and sorbitan fatty acid esters.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus mactans*, *Metatetranychus* spp., *Nuphersa* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acalymma vittatum*, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Psylliodes* spp., *Ptinus* spp., *Rhizobius ventralis*, *Rhizopertha dominica*, *Sitophilus* spp., *Sphenophorus* spp., *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Cochliomyia* spp., *Contarinia* spp., *Cordylobia anthropophaga*, *Culex* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia* spp., *Phorbia* spp., *Prodiplosis* spp., *Psila rosae*, *Rhagoletis* spp., *Stomoxys* spp., *Tabanus* spp., *Tannia* spp., *Tetanops* spp., *Tipula* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp, *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudospiralis*, *Trichostrongulus* spp., *Trichuris trichuria*, *Wuchereria bancrofti*.

It is furthermore possible to control protozoans, such as Eimeria.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes* spp., *Trioza* spp., *Typhlocyba* spp., *Unaspis* spp., *Viteus vitifolii*, *Zygina* spp.

From the order of the Hymenoptera, for example, *Athalia* spp., *Diprion* spp., *Hoplocampa* spp., *Lasius* spp., *Monomorium pharaonis*, *Vespa* spp.

From the order of the Isopoda, for example, *Armadillidium vulgare*, *Oniscus asellus*, *Porcellio scaber*.

From the order of the Isoptera, for example, *Acromyrmex* spp., *Atta* spp., *Cornitermes cumulans*, *Microtermes obesi*, *Odontotermes* spp., *Reticulitermes* spp.

From the order of the Lepidoptera, for example, *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Chematobia brumata*, *Chilo* spp., *Choristoneura* spp., *Clysia ambiguella*, *Cnaphalocerus* spp., *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia kuehniella*, *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamestra brassicae*, *Mocis* spp., *Mythimna separata*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plusia* spp., *Plutella xylostella*, *Prays* spp., *Prodenia* spp., *Protoparce* spp., *Pseudaletia* spp., *Pseudoplusia includens*, *Pyrausta nubilalis*, *Rachiplusia nu*, *Schoenobius* spp., *Scirpophaga* spp., *Scotia segetum*, *Sesamia* spp., *Sparganothis* spp., *Spodoptera* spp., *Stathmopoda* spp., *Stomopteryx subsecivella*, *Synanthe-*

*don* spp., *Tecia solanivora, Thermesia gemmatalis, Tinea pellionella, Tineola bisselliella, Tortrix* spp., *Trichoplusia* spp., *Tuta absoluta, Virachola* spp.

From the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta americana, Schistocerca gregaria*.

From the order of the Siphonaptera, for example, *Ceratophyllus* spp., *Xenopsylla cheopis*.

From the order of the Symphyla, for example, *Scutigerella* spp.

From the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina*.

The plant-parasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

According to the invention, a carrier is a natural or synthetic organic or inorganic substance which may be solid or liquid and with which the active compounds are mixed or bonded for better applicability, in particular for application to plants or parts of plants. The solid or liquid carrier is generally inert and should be suitable for use in agriculture.

Suitable solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergist added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparted particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The compounds of the formula (I) according to the invention (active compounds) have excellent herbicidal activity against a broad spectrum of economically important monocotylidonous and dicotylidonous annual harmful plants. The active compounds also act efficiently on perennial harmful plants which produce shoots from rhizomes, root stocks or other perennial organs and which are difficult to control.

The amount of active compound used may vary within a relatively wide range. It depends essentially on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, from 0.001 to 1000 parts by weight, preferably from 0.01 to 100 parts by weight, particularly preferably from 0.05 to 20 parts by weight, of one of the crop plant compatibility-improving compounds (antidotes/safeners) mentioned above under (b') are present per part by weight of active compound of the formula (I).

The active compound combinations according to the invention are generally applied in the form of finished formulations. However, the active compounds present in the active compound combinations can, as individual formulations, also be mixed during use, i.e. be applied in the form of tank mixtures.

For certain applications, in particular in the post-emergence method, it may furthermore be advantageous to include in the formulations, as further additives, mineral or vegetable oils which are tolerated by plants (for example the commercial preparation "Rako Binol"), or ammonium salts, such as, for example, ammonium sulphate or ammonium thiocyanate.

The novel active compound combinations can be used as such, in the form of their formulations or the use forms prepared therefrom by further dilution, such as ready-to-use solutions, suspensions, emulsions, powders, pastes and granules. The application is in the customary manner, for example by watering, spraying, atomizing, dusting or broadcasting.

The application rates of the active compound combinations according to the invention can be varied within a certain range; they depend, inter alia, on the weather and on soil factors. In general, the application rates are from 0.001 to 5 kg per ha, preferably from 0.005 to 2 kg per ha, particularly preferably from 0.01 to 0.5 kg per ha.

Depending on their properties, the safeners to be used according to the invention can be used for pretreating the seed of the crop plant (seed dressing) or can be introduced into the seed ferrules prior to the seed or be used separately prior to the herbicide or together with the herbicide, before or after emergence of the plants.

Examples of plants which may be mentioned are important crop plants, such as cereals (wheat, barley, rice), maize, soya beans, potatoes, cotton, oilseed rape, beet, sugar cane and also fruit plants (with the fruits apples, pears, citrus fruits and grapevines), greater emphasis being given to cereals, maize, soya beans, potatoes, cotton and oilseed rape.

All plants and plant parts can be treated with the active compounds according to the invention. Here, plants are to be understood as meaning all plants and plant populations such as wanted and unwanted wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders rights. Plant parts are to be understood as meaning all parts and organs of plants above and below the ground, such as shoot, leaf, flower and root, examples which may be mentioned being leaves, needles, stalks, stems, flowers, fruit bodies, fruits and seed and also roots, tubers and rhizomes. The plant parts also include harvested material, and also vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, broadcasting, painting on or injection and, in the case of propagation material, in particular in the case of seed, also by applying one or more coats.

The present invention therefore also relates to a method of controlling unwanted plants or for regulating the growth of plants, preferably in crops of plants, where one or more compound(s) according to the invention is/are applied to the plants (for example harmful plants such as monocotyledonous or dicotyledonous weeds or unwanted crop plants), to the seed (for example grains, seeds or vegetative propagules such as tubers or shoot parts with buds) or to the area on which the plants grow (for example the area under cultivation). In this context, the compounds according to the invention can be applied for example pre-planting (if appropriate also by incorporation into the soil), pre-emergence or post-emergence. Examples of individual representatives of the monocotyledonous and dicotyledonous weed flora which can be controlled by the compounds according to the invention shall be mentioned, without the mention being intended as a limitation to certain species.

Monocotyledonous Harmful Plants of the Genera:

*Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous Weeds of the Genera:

*Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

If the compounds according to the invention are applied to the soil surface before germination, either the emergence of the weed seedlings is prevented completely or the weeds grow until they have reached the cotyledon stage, but then stop their growth and, finally, die completely after three to four weeks have elapsed.

When the active compounds are applied post-emergence to the green plant parts, growth stops after the treatment, and the harmful plants remain in the growth stage of the time of application or die fully after a certain period of time, so that competition by weeds, which is harmful to the crop plants, is thus eliminated at an early point in time and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, are damaged only to an insignificant extent, or not at all, depending on the structure of the respective compound according to the invention and its application rate. This is why the present compounds are highly suitable for the selective control of unwanted vegetation in plant crops such as agriculturally useful plants or ornamentals.

Moreover, the compounds according to the invention (depending on their respective structure and the application rate applied) have outstanding growth-regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process.

Inhibiting the vegetative growth plays an important role in many monocotyledonous and dicotyledonous crops since for example lodging can be reduced, or prevented completely, hereby.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

Owing to their herbicidal and plant-growth-regulatory properties, the active compounds can also be employed for controlling harmful plants in crops of known genetically modified plants or genetically modified plants which are still to be developed. As a rule, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other special properties relate for example to the harvested material with regard to quantity, quality, storability, composition and specific constituents. Thus, transgenic plants with an increased starch content or a modified starch quality or those with a different fatty acid composition of the harvested material are known. Further particular properties may be tolerance or resistance to abiotec stresses, for example heat, cold, drought, salt and ultraviolet radiation.

It is preferred to use the compounds of the formula (I) according to the invention in economically important transgenic crops of useful plants and ornamentals, for example of cereals such as wheat, barley, rye, oats, sorghum and millet, rice, cassava and maize or else crops of sugar beet, cotton, soya bean, oilseed rape, potato, tomato, peas and other vegetables.

It is preferred to employ the compounds of the formula (I) as herbicides in crops of useful plants which are resistant, or have been made resistant by recombinant means, to the phytotoxic effects of the herbicides.

Conventional ways of generating novel plants which, in comparison with existing plants, have modified properties are, for example, traditional breeding methods and the generation of mutants. Alternatively, novel plants with modified properties can be generated with the aid of recombinant methods (see, for example, EP-A-0221044, EP-A-0131624). For example, the following have been described in several cases:

- recombinant modifications of crop plants for the purposes of modifying the starch synthesized in the plants (for example WO 92/11376, WO 92/14827, WO 91/19806),
- transgenic crop plants which are resistant to certain herbicides of the glufosinate type (cf., for example, EP-A-0242236, EP-A-242246) or of the glyphosate type (WO 92/00377) or of the sulphonylurea type (EP-A-0257993, U.S. Pat. No. 5,013,659),
- transgenic crop plants, for example cotton, which is capable of producing Bacillus thuringiensis toxins (Bt toxins), which make the plants resistant to certain pests (EP-A-0142924, EP-A-0193259),
- transgenic crop plants with a modified fatty acid composition (WO 91/13972),
- genetically modified crop plants with novel constituents or secondary metabolites, for example novel phytoalexins, which bring about an increased disease resistance (EPA 309862, EPA0464461),
- genetically modified plants with reduced photorespiration which feature higher yields and higher stress tolerance (EPA 0305398),
- transgenic crop plants which produce pharmaceutically or diagnostically important proteins ("molecular pharming"),
- transgenic crop plants which are distinguished by higher yields or better quality,
- transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

To carry out such recombinant manipulations, it is possible to introduce nucleic acid molecules into plasmids, which permit a mutagenesis or sequence modification by recombination of DNA sequences. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim 2nd ed., 1996

The generation of plant cells with a reduced activity for a gene product can be achieved for example by the expression of at least one corresponding antisense RNA, a sense RNA for achieving a cosuppression effect or by the expression of at least one correspondingly constructed ribozyme, which specifically cleaves transcripts of the abovementioned gene product.

To this end, it is possible firstly to use DNA molecules which comprise all of the coding sequence of a gene product, including any flanking sequences which may be present, or else DNA molecules which only comprise parts of the coding sequence, it being necessary for these parts to be long enough to bring about an antisense effect in the cells. It is also possible to use DNA sequences which have a high degree of homology with the coding sequences of a gene product, but which are not entirely identical.

When expressing nucleic acid molecules in plants, the protein synthesized may be localized in any compartment of the plant cell. In order to achieve localization in a particular compartment, however, it is possible for example to link the coding region to DNA sequences which ensure the localization in a specific compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give intact plants. In principle, the transgenic plants may be plants of any plant species, that is to say both monocotyledonous and dicotyledonous plants.

Thus, transgenic plants can be obtained which feature modified properties as the result of overexpression, suppression or inhibition of homologous (=natural) genes or gene sequences or expression of heterologous (=foreign) genes or gene sequences.

It is preferred to employ the compounds (I) according to the invention in transgenic crops which are resistant to growth regulators such as, for example, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulphonylureas, glyphosate, glufosinate or benzoylisoxazoles and analogous active compounds.

When the active compounds according to the invention are used in transgenic crops, effects are frequently observed—in addition to the effects on harmful plants which can be observed in other crops—which are specific for the application in the transgenic crop in question, for example a modified or specifically widened spectrum of weeds which can be controlled, modified application rates which may be employed for application, preferably good combinability with the herbicides to which the transgenic crop is resistant, and an effect on growth and yield of the transgenic crop plants.

The invention therefore also relates to the use of the compounds of the formula (I) according to the invention as herbicides for controlling harmful plants in transgenic crop plants.

The compounds according to the invention can be used in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell, Stuttgart 1976; Winnacker-Küchler, "Chemische Technologie", Volume 7, C. Hanser Verlag Munich, 4th Ed. 1986.

Based on these formulations, it is also possible to prepare combinations with other pesticidally active compounds, such as, for example, insecticides, acaracides, berbicides, fungicides, and also with safeners, fertilizers and/or growth regulators, for example in the form of a finished formulation or as a tank mix.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulphates, alkanesulphonates, alkylbenzenesulphonates, sodium lignosulphonate, sodium 2,2'-dinaphthylmethane-6,6'-disulphonate, sodium dibutylnaphthalenesulphonate or else sodium oleylmethyltauride. To prepare the wettable powders, the active herbicidal compounds are ground finely, for example in customary apparatus such as hammer mills, blower mills and air-jet mills and simultaneously or subsequently mixed with the formulation assistants.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulphonates such as calcium dodecylbenzenesulphonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active compound with finely divided solid substances, for example talc, natural clays such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be produced either by spraying the active compound onto adsorptive granulated inert material or by applying active compound concentrates by means of adhesives, for example polyvinyl alcohol, sodium polyacrylate or else mineral oils, onto the surface of carriers such as sand, kaolinites or of granulated inert material. It is also possible to granulate suitable active compounds in the manner customary for the production of fertilizer granules—if desired in a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of compounds according to the invention.

In wettable powders, the active compound concentration is, for example, from about 10 to 90% by weight; the remainder to 100% by weight consists of customary formulation constituents. In the case of emulsifiable concentrates, the active compound concentration may be from about 1 to 90% by weight, preferably from 5 to 80% by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In water-dispersible granules, the active compound content depends partly on whether the active compound is present in solid or liquid form and which granulation assistants, fillers, etc. are used. In the granules dispersible in water, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity.

The term "active compounds" or "compounds" in each case also includes the active compound combinations mentioned herein.

The preparation and the use of the active compounds according to the invention is illustrated by the examples below.

PREPARATION EXAMPLES

Examples I-a-0 and I-a-1

3-(Benzyloxy)-2-(2,6-diethyl-4-methylphenyl)-5-methylene-4,5,6,6a-tetrahydropentalen-1(3aH)-one and 3-(benzyloxy)-2-(2,6-diethyl-4-methylphenyl)-5-(hydroxymethyl)-4,5,6,6a-tetrahydropentalen-1(3aH)-one

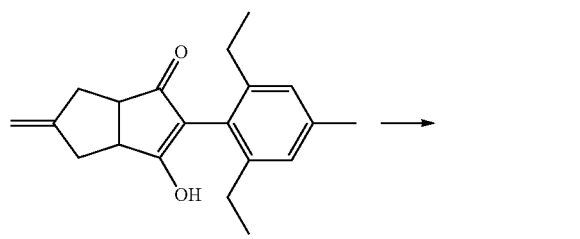

known from WO 2010/040460
Preparation Example I-a-5

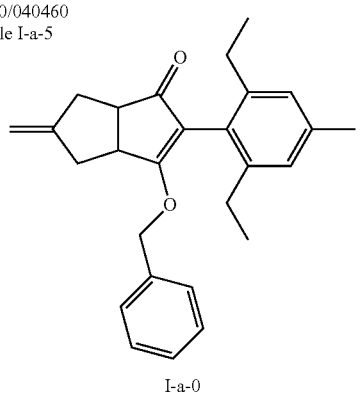

I-a-0

6.80 g (22.94 mmol) of 2-(2,6-diethyl-4-methylphenyl)-3-hydroxy-5-methylene-4,5,6,6a-tetrahydropentalen-1(3aH)-one (Preparation Example I-a-5 known from WO 2010/040460), 8.71 g (68.82 mmol) of benzyl chloride and 9.51 g of potassium carbonate in 50 ml of acetone are heated at reflux for 2 h, the solvent is then distilled off and the residue is chromatographed on silica gel using ethyl acetate/hexane 1:4. This gives 6.40 g (72%) of 3-(benzyloxy)-2-(2,6-diethyl-4-methylphenyl)-5-methylene-4,5,6,6a-tetrahydropentalen-1(3aH)-one in the form of colourless crystals of m.p. 87-88° C.

$^1$H-NMR (400 MHz, CDCl$_3$): δ=1.03 and 1.12 (in each case t, in each case 3H), 3.03 and 3.37 (in each case mc, in each case 1H), AB system: δ$_A$=4.73, δ$_B$=4.79, J=13 Hz (benzyl-C$\underline{H}_2$), 4.90 (mc, 2H), 6.88 and 7.12 (in each case mc, in each case 2H), 7.32 (mc, 3H)

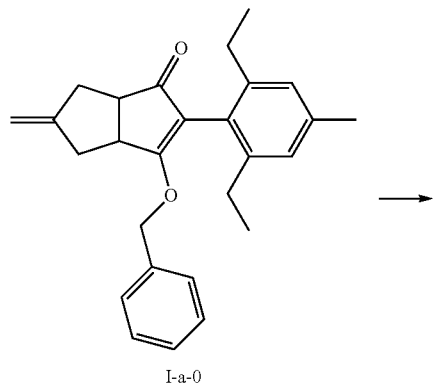

I-a-0

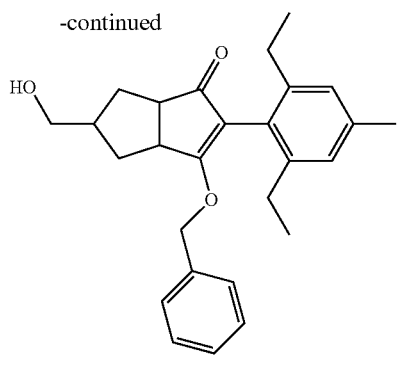

I-a-1

Over a period of 30 min, 17 ml of borane/THF (tetrahydrofuran) complex (1 molar solution, 17 mmol) are added dropwise to 6.00 g (15.52 mmol) of 3-(benzyloxy)-2-(2,6-diethyl-4-methylphenyl)-5-methylene-4,5,6,6a-tetrahydropentalen-1(3aH)-one in 100 ml of THF, and the mixture is then stirred at room temperature for another 1 h. 6 ml of water and 3 ml of 3 molar aqueous sodium hydroxide solution are added to this mixture, and 2.3 ml of 35% strength hydrogen peroxide are then metered in such that the internal temperature remains between 30 and 50° C. The mixture is stirred at room temperature for another 1 h and then concentrated using a rotary evaporator, taken up in dichloromethane, washed twice with water and dried (magnesium sulphate), and the solvent is distilled off. Chromatography on silica gel (ethyl acetate/hexane 1:4) gives 4.39 g (70%) of the desired product (I-a-1) as a viscous, colourless oil. The syn/anti-isomer ratio according to $^1$H-NMR is about 85:15.

$^1$H-NMR (400 MHz, CDCl$_3$): δ=1.10 (mc, 6H), 3.02-3.15 (m, 1H), 3.40 (mc, 1H), 3.55-3.69 (m, 2H), AB system: δ$_A$=4.78, δ$_B$=4.82, J=13 Hz (benzyl-C$\underline{H}_2$ anti-isosomer), 4.85 (s, benzyl-C$\underline{H}_2$ syn-isomer, 6.88 (mc, 2H), 7.12 (mc, 2H), 7.30 (mc, 3H).

Example I-a-2

6-(Benzyloxy)-5-(2,6-diethyl-4-methylphenyl)-4-oxo-1,2,3,3a,4,6a-hexahydropentalene-2-carbaldehyde

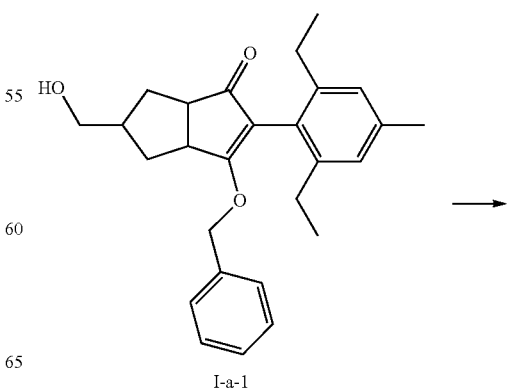

I-a-1

-continued

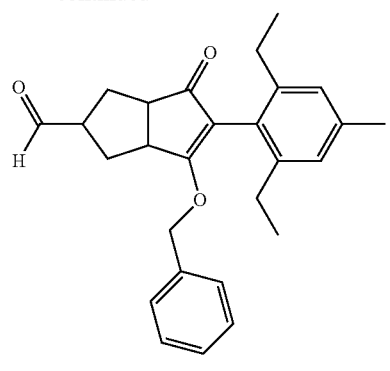

I-a-2

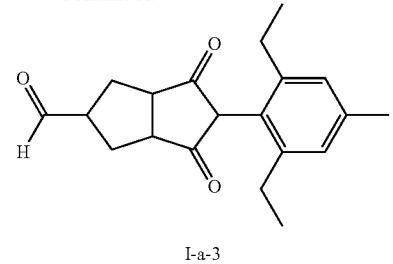

I-a-3

20 mg of palladium on activated carbon (10%) are added to 1.10 g (2.72 mmol) of 6-(benzyloxy)-5-(2,6-diethyl-4-methylphenyl)-4-oxo-1,2,3,3a,4,6a-hexahydropentalene-2-carbaldehyde in 20 ml of methanol, and the mixture is hydrogenated (15 bar, room temperature) for 20 h. The filtration and concentration on a rotary evaporator give 0.82 g (97%) of the title compound (I-a-3, isomer ratio according to $^1$H-NMR 4:1).

$^1$H-NMR (400 MHz, CDCl$_3$): δ=1.05 (mc, 6H), 2.90 (mc, 1H), 3.09-3.40 (m, br, 2H), 6.91 (mc, 2H), 9.62 (mc, CHO isomer 1), 9.68 (mc, CHO isomer 2).

At −78° C., 1.31 g (16.8 mmol) of dimethyl sulphoxide are slowly added dropwise to 1.067 g (8.4 mmol) of oxalyl chloride in 40 ml of dichloromethane, and the mixture is stirred at this temperature for 20 min. 1.70 g (4.20 mmol) of 3-(benzyloxy)-2-(2,6-diethyl-4-methylphenyl)-5-(hydroxymethyl)-4,5,6,6a-tetrahydropentalen-1(3aH)-one (Example I-a-1), dissolved in 30 ml of dichloromethane, are then slowly added dropwise, and the mixture is stirred for another hour. 2.13 g (21 mmol) of triethylamine are then added slowly, and the mixture is brought to room temperature. Addition of 50 ml of saturated ammonium chloride solution, separation, washing of the organic phase with water, drying (magnesium sulphate), concentration on a rotary evaporator and chromatographic purification of the resulting crude product on silica gel (mobile phase ethyl acetate/hexane 1:5) gives 1.24 g (73%) of the title compound as a colourless oil.

$^1$H-NMR (400 MHz, CDCl$_3$): δ=1.08 and 1.12 (in each case t, in each case 3H), 2.30 (s, 3H), 2.90 (mc, 1H), 3.12 (mc, 1H), 3.41 (mc, 1H), 4.72 (s, 2H), 6.89 (mc, 2H), 9.70 (mc, 1H).

Example I-a-3

5-(2,6-Diethyl-4-methylphenyl)-4,6-dioxooctahydropentalene-2-carbaldehyde

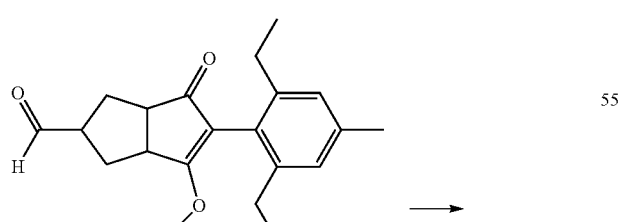

I-a-2

Example I-a-4

5-(2,6-Diethyl-4-methylphenyl)-4,6-dioxooctahydropentalene-2-carbonitrile

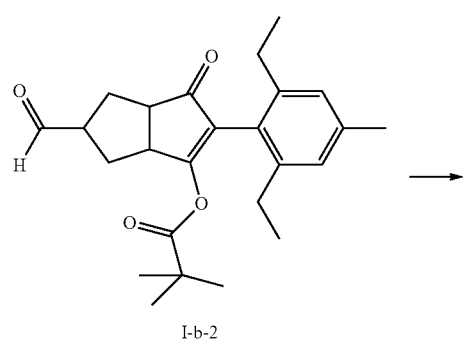

I-b-2

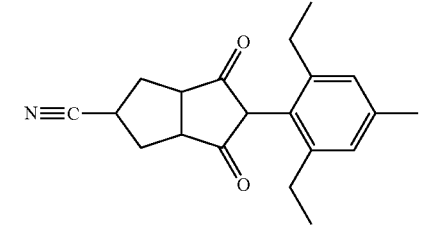

I-a-4

0.91 g (2.30 mmol) of 2-(2,6-diethyl-4-methylphenyl)-5-formyl-3-oxooctahydropentalen-1-yl 2,2-dimethylpropanoate (Example I-b-2), 0.78 g (11.48 mmol) of sodium formate and 0.80 g (11.48 mmol) of hydroxylamine hydrochloride in 30 ml of formic acid are heated at reflux for 72 h. 50 ml of water are then added, and the mixture is stirred at room temperature for 1 h, taken up in ethyl acetate, washed twice with water, dried (magnesium sulphate) and concentrated using a rotary evaporator. The residue is chromatographed on silica gel (mobile phase ethyl acetate/hexane 1:6). This gives 0.31 g (44%) of the desired compound as a colourless oil.

¹H-NMR (400 MHz, CDCl₃): δ=1.08 and 1.11 (in each case t, in each case 3H), 2.00 (mc, 2H), 2.48 (mc, 2H), 2.99 (mc, 1H), 6.95 (mc, 2H).

Example I-a-5

2-(2,6-Diethyl-4-methylphenyl)-5-(1,3-dioxan-2-yl)tetrahydropentalene-1,3(2H,3aH)-dione

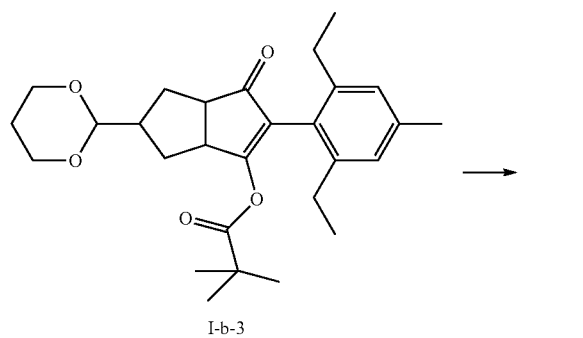

I-b-3

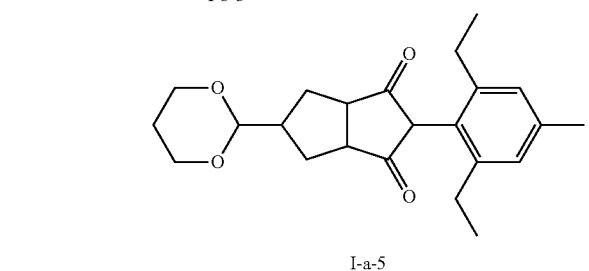

I-a-5

0.100 g (0.22 mmol) of 2-(2,6-diethyl-4-methylphenyl)-5-(1,3-dioxan-2-yl)-3-oxo-3,3a,4,5,6,6a-hexahydropentalen-1-yl 2,2-dimethylpropanoate in 10 ml of methanol and 4 ml of 1N aqueous sodium hydroxide solution is stirred at room temperature for 2 h. The mixture is then concentrated, the residue is taken up in water, the mixture is acidified to pH 4 using 2N HCl and extracted with ethyl acetate, the extract is dried (magnesium sulphate) and the solvent is distilled off. Chromatographic purification of the residue on silica gel (mobile phase ethyl acetate/hexane 1:6) gives 70 mg (86%) of the desired compound in the form of colourless needles of m.p. 100-101° C.

Example I-a-82

2-(2,6-diethyl-4-methylphenyl)-5-methoxymethyltetrahydropentalene-1,3-dione

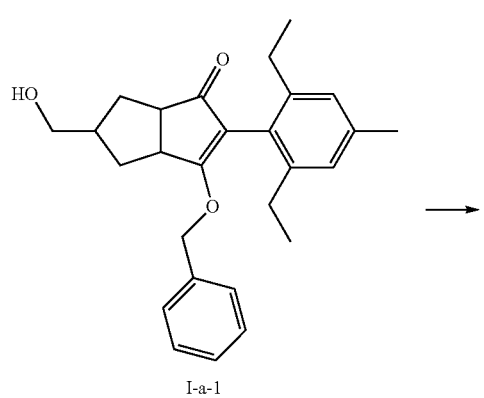

I-a-1

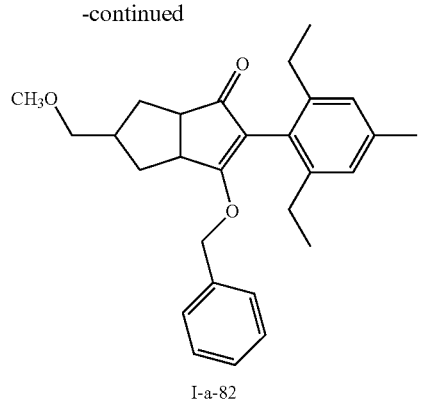

I-a-82

0.762 g (1.88 mmol) of the compound I-a-1 (3-(benzyloxy)-2-(2,6-diethyl-4-methylphenyl)-5-(hydroxymethyl)-4,5,6,6a-tetrahydropentalene-1(3aH)-one) in 5 ml of tetrahydrofuran is added dropwise to 93 mg (2.32 mmol) of sodium hydride in 20 ml of tetrahydrofuran, and the mixture is stirred at room temperature for another 30 minutes. 309 mg (2.45 mmol) of dimethyl sulphate, dissolved in 2 ml of tetrahydrofuran, are then slowly added dropwise, and the mixture is heated at reflux for 2 h. The mixture is taken up in ethyl acetate, extracted twice with water, dried (magnesium sulphate), and the solvent is distilled off. Chromatography on silica gel (mobile phase ethyl acetate/hexane 1:5) gives 0.50 g (64%) of the desired compound in the form of colourless crystals of m.p. 75-76° C.

Example I-a-29

2-(2,6-diethyl-4-methylphenyl)-5-methoxymethyltetrahydropentalene-1,3-dione

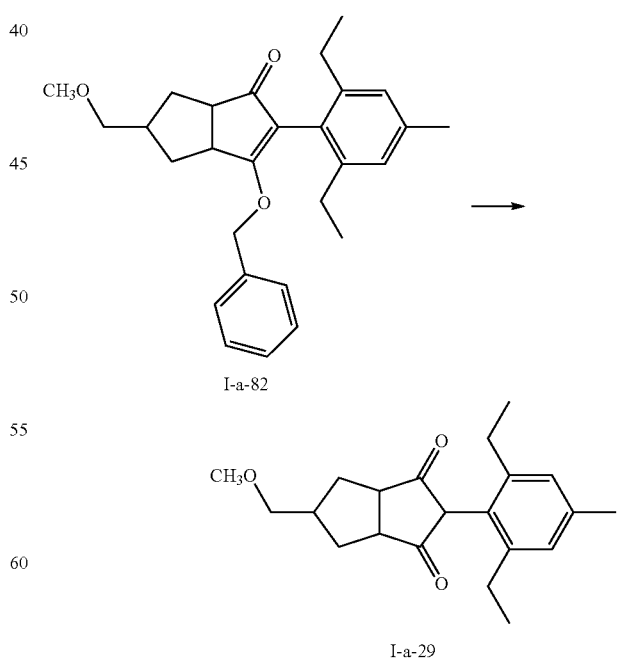

After addition of 5 mg of catalyst (Pd/C, 5%), 80 mg (0.19 mmol) of the compound I-a-82 in 10 ml of methanol are hydrogenated at room temperature and at a pressure of 5 bar. After filtration and removal of the solvent by distillation, 58 mg (92%) of the desired compound I-a-29 are obtained as a yellowish oil.

¹H-NMR (400 MHz, CDCl₃): δ=1.08 and 1.11 (in each case t, in each case 3H), 2.00 (mc, 2H), 2.48 (mc, 2H), 2.99 (mc, 1H), 6.95 (mc, 2H).

Example I-a-39

2-(2,6-diethyl-4-methylphenyl)-5-(3-oxobutyl)-tetrahydropentalene-1,3-dione

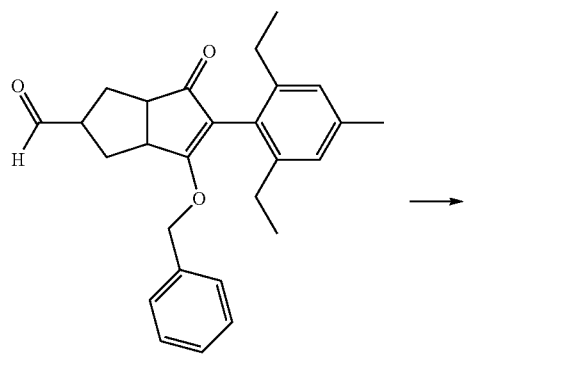

I-a-2

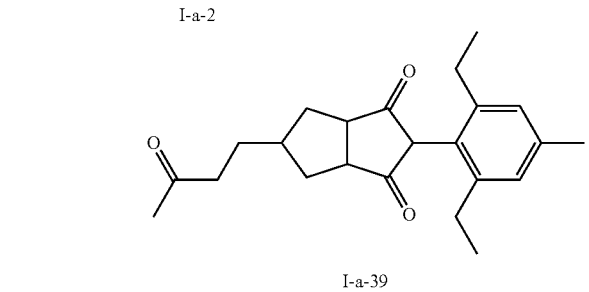

I-a-39

1.87 g (4.65 mmol) of 6-(benzyloxy)-5-(2,6-diethyl-4-methylphenyl)-4-oxo-1,2,3,3a,4,6a-hexahydropentalene-2-carbaldehyde (compound I-a-2) and 1.63 g (5.11 mmol) of acetonylidenetriphenylphosphorane in 40 ml of trichloromethane are stirred at room temperature for 12 h. The solvent is then removed, and the residue is purified chromatographically on silica gel (mobile phase ethyl acetate/hexane 1:5). This gives 1.37 g (66%) of 3-benzyloxy-2-(2,6-diethyl-4-methylphenyl)-5-(3-oxobut-1-enyl)-4,5,6,6a-tetrahydro-3aH-pentalen-1-one as a colourless oil.

¹H-NMR (400 MHz, CDCl₃): δ=1.10 (mc, 6H), 2.25 (s, 3H), 2.31 (s, 3H), 2.93, 3.19 and 3.44 (in each case mc, in each case 1H), 4.80 (s, H), 6.12 (d, 1H), 6.74 (dd, 1H), 6.90 (mc, 2H)

20 mg of 5% Pd/C catalyst are added to 1.30 g (2.94 mmol) of this intermediate in 40 ml of methanol, and the intermediate is hydrogenated catalytically at room temperature and a pressure of 5 bar for 10 h. Filtration and removal of the solvent by distillation give 1.040 g (99%) of the desired target compound I-a-39 in the form of yellowish crystals of m.p. 60° C.

Example I-a-42

2-(2,6-diethyl-4-methylphenyl)-5-[3-methoxyiminobutyl]-tetrahydropentalene-1,3-dione

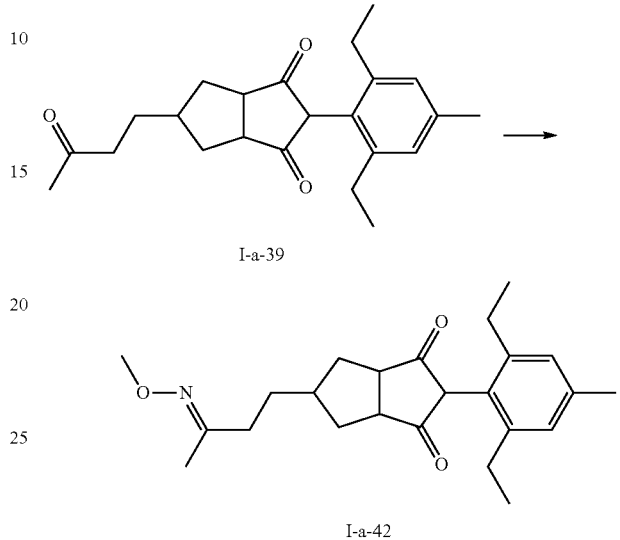

267 mg (0.82 mmol) of 2-(2,6-diethyl-4-methylphenyl)-5-(oxobutyl)-tetrahydropentalene-1,3-dione (example I-a-39), 102 mg (1.23 mmol) of O-methylhydroxylamine hydrochloride and 0.5 ml of triethylamine in 10 ml of acetonitrile are stirred at room temperature overnight. The mixture is then taken up in ethyl acetate, washed with water and dried (magnesium sulphate) and the solvent is distilled off Chromatography on silica gel (mobile phase ethyl acetate/hexane 1:4) gives 225 mg (77%) of the target compound in the form of colourless crystals of m.p. 79-80° C.

Example I-a-40

2-(2,6-diethyl-4-methylphenyl)-5-methoxymethoxymethyltetrahydropentalene-1,3-dione

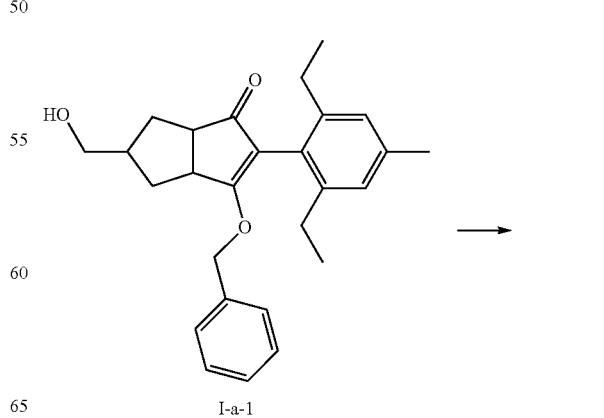

I-a-1

-continued

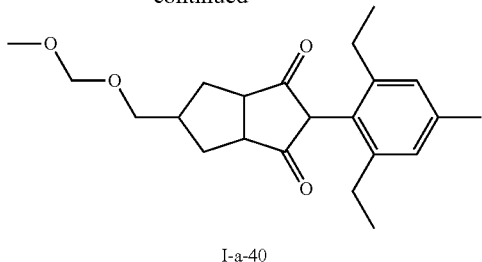

I-a-40

200 mg (0.49 mmol) of the compound from example I-a-1, and 1.12 g (14.8 mmol) of dimethoxyethane together with 10 mg of scandium trifluoromethanesulphonate are heated at reflux in 10 ml of trichloromethane for 8 h. The reaction mixture is diluted with water, the phases are separated and the organic phase is washed with water and 0.5 N aqueous sodium hydroxide solution, dried (magnesium sulphate) and concentrated on a rotary evaporator. Chromatography on silica gel (mobile phase ethyl acetate/hexane 1:5) gives 130 mg (59%) of 3-benzyloxy-2-(2,6-diethyl-4-methylphenyl)-5-methoxymethoxymethyl-4,5,6,6a-tetrahydro-3aH-pentalen-1-one as a colourless oil.

$^1$H-NMR (400 MHz, CDCl$_3$): δ=1.10 (mc, 6H), 2.30 (s, 3H), 3.15 (mc, 1H), 3.35 (s, 3H), 4.60 (s, 2H), 4.85 (s, 2 h), 6.89 (mc, 2H)

As described in example I-a-29, 123 mg (274 mmol) of this compound are subjected to catalytical hydrogenation. This gives 95 mg (96%) of the title compound in the form of colourless crystals of m.p. 155-156° C.

Example I-a-77

2-(2,6-diethyl-4-methylphenyl)-5-{[(4,5-dimethyl-1,3-thiazol-2-yl)oxy]methyl}tetrahydropentalene-1,3(2H,3aH)-dione

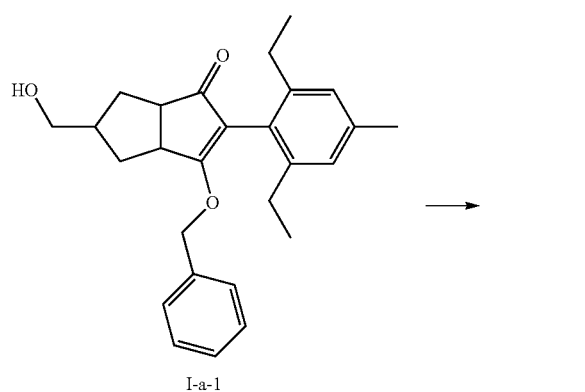

I-a-1

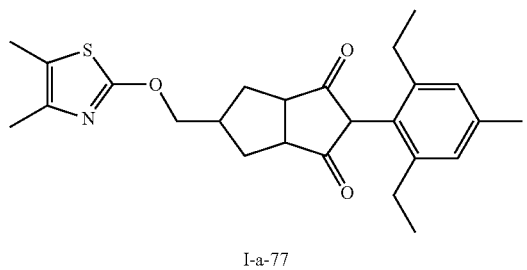

I-a-77

0.83 g (2.05 mmol) of the compound I-a-1 and 0.123 g (3.07 mmol) of sodium hydride in 30 ml of THF are heated at reflux for 30 minutes. 0.30 g (2 mmol) of 2-chloro-4,5-dimethyl-1,3-thiazole is then added dropwise at room temperature, and the mixture is heated at reflux for 2 h. After cooling, 5 ml of 2N hydrochloric acid are added carefully, and the mixture is taken up in ethyl acetate, washed with water, dried (magnesium sulphate) and concentrated using a rotary evaporator. Chromatography on silica gel (mobile phase ethyl acetate/hexane 1:6) gives 0.31 g (30%) of 3-benzyloxy-2-(2,6-diethyl-4-methylphenyl)-5-(4,5-dimethylthiazol-2-yloxymethyl)-4,5,6,6a-tetrahydro-3aH-pentalen-1-one as a colourless oil.

$^1$H-NMR (400 MHz, CDCl$_3$): δ=1.10 (mc, 6H), 2.13, 2.20 and 2.32 (in each case s, in each case 3H), 3.15 and 3.40 (in each case mc, in each case 1H), 4.25-4.35 (m, 2H), 4.82 (s, 2H), 4.60 (s, 2H), 6.90 and 7.12 (in each case mc, in each case 2H), 7.30 (mc, 3H)

As described in example I-a-29, 0.170 g (0.33 mmol) of this compound is subjected to catalytical hydrogenation (methanol, 5% Pd/C, 5 bar). This gives 0.140 g (99%) of the desired title compound I-a-77 in the form of colourless crystals of m.p. 73-74° C.

$^1$H-NMR (400 MHz, CDCl$_3$): δ=1.05 (mc, 6H), 2.11, 2.19 and 2.31 (in each case s, in each case 3H), 2.62 (mc, 1H), 3.15-3.32 (m, 2H), 4.27 (d, 2H), 6.91 (mc, 2H)

Example I-a-83

2-[5-(2,6-diethyl-4-methylphenyl)-4,6-dioxohexahydropentalen-2-ylidene]-malononitrile

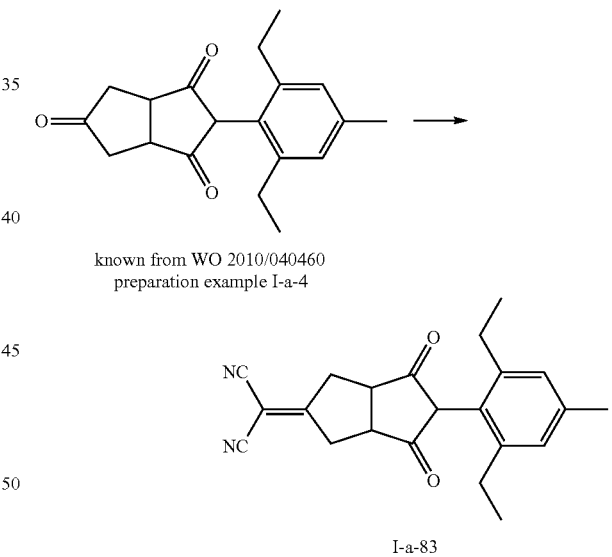

I-a-83

0.500 g (1.70 mmol) of 2-(2,6-diethyl-4-methylphenyl) tetrahydropentalene-1,3,5-trione (example I-a-4 from WO 2010/040460), 250 mg of malononitrile, 150 mg of ammonium acetate and 0.3 ml of glacial acetic acid in 30 ml of toluene are heated at reflux for 2 h. After cooling, the solvent is distilled off and the mixture is taken up in ethyl acetate, washed twice with water, then dried (magnesium sulphate) and concentrated on a rotary evaporator. What remains is a yellow oil which is chromatographed on silica gel using ethyl acetate/hexane 1:6. This gives 0.32 g (56%) of a colourless oil.

$^1$H-NMR (400 MHz, CDCl$_3$): δ=1.02 and 1.08 (in each case t, in each case 3H), 2.21 and 2.38 (in each case mc, in each case 2H), 2.31 (s, 3H), 3.12 and 3.30 (in each case mc, in each case 2H), 3.40 and 3.58 (in each case mc, in each case 1H), 6.95 (mc, 2H).

Example I-a-35

2-[3aR,6aS)-5-(2,6-diethyl-4-methylphenyl)-4,6-dioxooctahydropentalen-2-yl]malononitrile

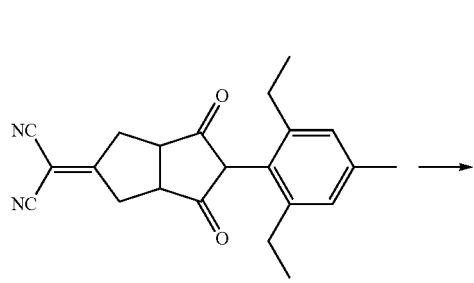

I-a-83

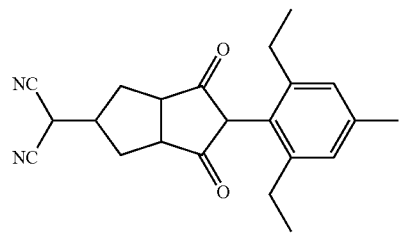

I-a-35

0.75 g (1.98 mmol) of sodium borohydride are added to 230 mg (0.66 mmol) of 2-[5-(2,6-diethyl-4-methylphenyl)-4, 6-dioxohexahydropentalen-2-ylidene]malononitrile in a mixture of 10 ml of methanol and 10 ml of tetrahydrofuran, and the mixture is stirred at room temperature for 2 h. The solvent is distilled off and the mixture is taken up in ethyl acetate, washed with water, dried (magnesium sulphate) and concentrated on a rotary evaporator. Chromatographic purification of the residue gives 140 mg (60%) of the desired compound in the form of colourless crystals of m.p. 116-117° C.

$^1$H-NMR (400 MHz, CDCl$_3$): δ=1.06 (mc, 6H), 1.61 (mc, 2H), 2.31 (s, 3H), 2.33 (mc, 4H), 2.50 (mc, 2H), 2.77 (mc, 1H), 3.82 (d, 1H), 6.95 (mc, 2H).

Example I-a-84

Ethyl cyano-[5-(2,6-diethyl-4-methylphenyl)-4,6-dioxohexahydropentalen-(2Z)-ylidene]acetate

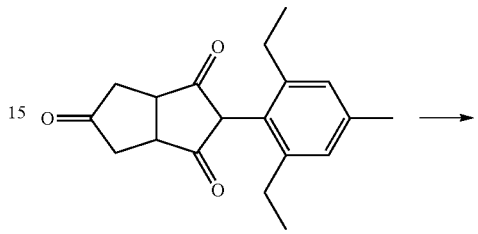

known from WO 2010/040460
preparation example I-a-4

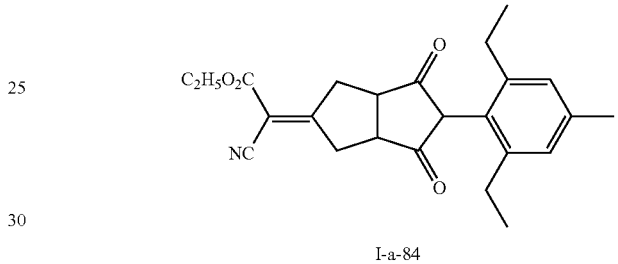

I-a-84

3.37 g (11.29 mmol) of 2-(2,6-diethyl-4-methylphenyl) tetrahydropentalene-1,3,5-trione, 2.55 g (22.59 mmol) of ethyl cyanoacetate, 870 mg (11.3 mmol) of ammonium acetate and 2.5 ml of glacial acetic acid in 70 ml of toluene are reacted analogously to example I-a-82. This gives, after chromatography on silica gel (ethyl acetate/hexane 1:6), 0.99 g (22%) of the desired compound as a colourless oil.

$^1$H-NMR (400 MHz, CDCl$_3$): δ=0.94 and 1.08 (in each case t, in each case 3H), 1.32 (t, 3H), 2.20 (mc, 2H), 2.30 (s, 3H), 2.36 (mc, 2H), 3.10-3.20 (mc, 2H), 4.28 (q, 2H), 6.90 (mc, 2H).

The following compounds of the formula (I-a) are obtained analogously to Examples (I-a-1) to (I-a-5) and in accordance with the general statements on the preparation:

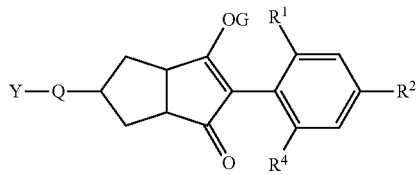

(I-a)

| Ex. No. | R1 | R2 | R4 | G | Y—Q | m.p. [° C.] or $^1$H-NMR (400 MHz, CDCl$_3$, δ in ppm) | Notes |
|---|---|---|---|---|---|---|---|
| I-a-6 | C$_2$H$_5$ | CH$_3$ | C$_2$H$_5$ | H | C$_2$H$_5$O\\ /CH \\ /C$_2$H$_5$O | δ = 1.07 and 1.20 (in each case mc, in each case 6H), 3.18 (mc, 2H), 3.50 and 3.65 (in each case mc, in each case 2H), 4.27 and 4.31 (in each case d, Σ 1H), 6.92 (mc, 2H) | syn/anti mixture |
| I-a-7 | C$_2$H$_5$ | CH$_3$ | C$_2$H$_5$ | H | HOCH$_2$— | δ = 1.05-1.10 (m, 6H), 3.10-3.22 (m, 1H), 3.39 (mc, 1H), 3.55-3.68 (m, 2H, C$\underline{H}_2$OH), 6.94 (mc, 2H) | syn-isomer |
| I-a-8 | C$_2$H$_5$ | CH$_3$ | C$_2$H$_5$ | H | HO$_2$C— | 124-125° C. | anti-isomer |

-continued

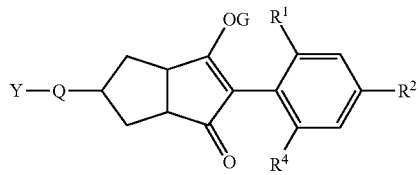

(I-a)

| Ex. No. | R1 | R2 | R4 | G | Y—Q | m.p. [° C.] or $^1$H-NMR (400 MHz, CDCl$_3$, δ in ppm) | Notes |
|---|---|---|---|---|---|---|---|
| I-a-9 | C$_2$H$_5$ | CH$_3$ | C$_2$H$_5$ | H | CH$_3$O$_2$C— | 72-73° C. | anti-isomer |
| I-a-10 | C$_2$H$_5$ | CH$_3$ | C$_2$H$_5$ | H | (2-methyl-1,3-dioxolan-2-yl) | 86-87° C. | anti-isomer |
| I-a-11 | CH$_3$ | CH$_3$ | CH$_3$ | H | OHC— | 131-132° C. | syn/anti mixture |
| I-a-12 | C$_2$H$_5$ | CH$_3$ | C$_2$H$_5$ | H | (CH$_3$O)$_2$CH— | 71-72° C. | anti-isomer |
| I-a-13 | C$_2$H$_5$ | CH$_3$ | C$_2$H$_5$ | H | CH$_3$O—N=CH— | δ = 1.08 (t, 6H), 2.93 (mc, 1H), 3.35 (mc, 2H), 3.71 (s, 3H), 6.51 and 7.30 (in each case d, Σ 1H) | E/Z mixture syn/anti mixture |
| I-a-14 | C$_2$H$_5$ | CH$_3$ | C$_2$H$_5$ | H | C$_3$H$_5$CH$_2$O—N=CH— | δ = 0.25 and 0.52 (in each case mc, in each case 2H), 2.95 (mc, 1H), 3.10-3.42 (s, br, 2H), 3.50 (mc, 1H), 3.82 and 3.88 (in each case d, Σ 2H), 6.53 and 7.38 (in each case d, Σ 1H) | E/Z mixture syn/anti mixture |
| I-a-15 | C$_2$H$_5$ | CH$_3$ | C$_2$H$_5$ | H | $^i$PrO—N=CH— | 68-69° C. | E/Z mixture syn/anti mixture |
| I-a-16 | C$_2$H$_5$ | CH$_3$ | C$_2$H$_5$ | H | (2-methyl-4,7-dihydro-1,3-dioxepin-2-yl) | δ = 1.03 (mc, 6H), 3.05 and 3.33 (in each case mc, in each case 1H), 4.10-4.18 and 4.33-4.39 (in each case m, in each case 2H), 4.52 and 4.59 (in each case d, in each case 1H), 5.70 (s, 2H) | syn/anti mixture |
| I-a-17 | C$_2$H$_5$ | CH$_3$ | C$_2$H$_5$ | H | Cl$_2$C=CHCH$_2$O—N=CH— | δ = 1.08 (t, 6H), 2.32 (s, 3H), 2.95 (mc, 1H), 4.58 and 4.66 (in each case d, Σ 2H), 6.10 (mc, 1H), 6.60 and 7.37 (in each case d, Σ 1H) | E/Z mixture syn/anti mixture |
| I-a-18 | C$_2$H$_5$ | CH$_3$ | C$_2$H$_5$ | H | HC≡CCH$_2$O—N=CH— | 2.43 and 2.46 (in each case t, Σ 1H), 4.60 and 4.65 (in each case mc, Σ 2H), 6.62 and 7.38 (in each case d, Σ 1H) | E/Z mixture syn/anti mixture |
| I-a-19 | C$_2$H$_5$ | CH$_3$ | C$_2$H$_5$ | H | (2,5,5-trimethyl-1,3-dioxan-2-yl) | δ = 0.70 and 1.15 (in each case s, in each case 3H), 1.08 (mc, 6H), 1.50 and 2.20 (in each case mc, in each case 2H), 3.38 and 3.55 (in each case d, in each case 2H), 4.24 (d, 1H), | anti-isomer |
| I-a-20 | C$_2$H$_5$ | CH$_3$ | C$_2$H$_5$ | H | (2-methyl-1,3-dioxepan-2-yl, t-Bu-substituted) | δ = 1.05 (mc, 6H), 1.15 (s, 9H), 2.02 and 3.30 (in each case mc, in each case 1H), 3.60 (mc, 3H), 4.08 (mc, 1H), 4.45 and 4.50 (in each case d, Σ 1H), 6.92 (mc, 2H) | syn/anti mixture |
| I-a-21 | C$_2$H$_5$ | CH$_3$ | C$_2$H$_5$ | H | HO—N=CH— | δ = 1.08 (mc, 6H), 2.32 (s, 3H), 3.20 and 3.41 (in each case mc, in each case 1H), 6.64 and 7.40 (in each case d, Σ 1H), 6.95 (mc, 2H) | E/Z mixture syn/anti mixture |
| I-a-22 | C$_2$H$_5$ | CH$_3$ | C$_2$H$_5$ | H | CH$_3$O | δ = 1.05-1.10 (m, 6H), 2.30 (s, 3H), 3.05-3.30 (s, broad, 2H), 3.18 (s, 3H), 3.87 (mc, 1H). | syn-isomer |
| I-a-23 | C$_2$H$_5$ | CH$_3$ | C$_2$H$_5$ | H | OH | 114-115° C. | syn-isomer |
| I-a-24 | C$_2$H$_5$ | CH$_3$ | C$_2$H$_5$ | H | (2-methyl-1,3-dithian-2-yl) | 127-128° C. | syn/anti mixture |

-continued

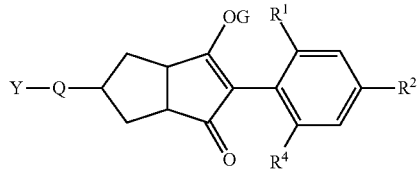

(I-a)

| Ex. No. | R1 | R2 | R4 | G | Y—Q | m.p. [° C.] or $^1$H-NMR (400 MHz, CDCl$_3$, δ in ppm) | Notes |
|---|---|---|---|---|---|---|---|
| I-a-25 | C$_2$H$_5$ | CH$_3$ | C$_2$H$_5$ | H | (2-methyl-1,3-oxathian-2-yl) | δ = 1.05 (t, 6H), 2.32 (s, 3H), 3.59 (mc, 1H), 4.14 (mc, 1H), 4.66 and 4.70 (in each case d, Σ 1H), 6.91 (s, 2H) | syn/anti mixture |
| I-a-26 | C$_2$H$_5$ | CH$_3$ | C$_2$H$_5$ | H | (2-methyl-1,3-dithiolan-2-yl) | 103-104° C. | syn/anti mixture |
| I-a-27 | CH$_3$ | CH$_3$ | CH$_3$ | H | CH$_3$O—N═CH— | 204-205° C. | E/Z mixture syn/anti mixture |
| I-a-28 | C$_2$H$_5$ | CH$_3$ | C$_2$H$_5$ | H | CH$_3$(C═O)OCH$_2$— | 101-103° C. | syn-isomer |
| I-a-29 | C$_2$H$_5$ | CH$_3$ | C$_2$H$_5$ | H | CH$_3$OCH$_2$— | 159-160° C. | syn-isomer |
| I-a-30 | CH$_3$ | CH$_3$ | CH$_3$ | H | (2-methyl-1,3-dioxolan-2-yl) | 97-98° C. | syn/anti mixture |
| I-a-31 | CH$_3$ | CH$_3$ | CH$_3$ | H | iPrO—N═CH— | δ = 1.18 and 1.20 (in each case d, in each case 3H), 2.05 (s, 6H), 2.28 (s, 3H), 4.25 (mc, 1H), 6.51 and 7.30 (in each case d, Σ 1H), 6.88 (mc, 2H) | E/Z mixture syn/anti mixture |
| I-a-32 | CH$_3$ | CH$_3$ | CH$_3$ | H | (2-methyl-1,3-dioxan-2-yl) | 135-136° C. | syn/anti mixture |
| I-a-33 | C$_2$H$_5$ | CH$_3$ | C$_2$H$_5$ | H | CH$_3$C═O— | 90-91° C. | syn/anti mixture |
| I-a-34 | C$_2$H$_5$ | CH$_3$ | C$_2$H$_5$ | H | CH$_3$C(═NOCH$_3$)— | 195-196° C. | E/Z mixture syn/anti mixture |
| I-a-35 | C$_2$H$_5$ | CH$_3$ | C$_2$H$_5$ | H | (NC)$_2$CH— | 116-117° C. | syn/anti mixture |
| I-a-36 | C$_2$H$_5$ | CH$_3$ | C$_2$H$_5$ | H | —CH$_2$CH$_2$CO$_2$CH$_3$ | 59-60° C. | syn/anti mixture |
| I-a-37 | C$_2$H$_5$ | CH$_3$ | C$_2$H$_5$ | H | —CH$_2$CH$_2$CN | 142-145° C. | syn/anti mixture |
| I-a-38 | C$_2$H$_5$ | CH$_3$ | C$_2$H$_5$ | H | (N-succinimidyl-CH$_2$—) | 142-145° C. | syn/anti mixture |
| I-a-39 | C$_2$H$_5$ | CH$_3$ | C$_2$H$_5$ | H | CH$_3$(C═O)CH$_2$CH$_2$— | δ = 1.08 (mc, 6H), 2.12 (s, 3H), 2.30 (s, 3H), 3.28 (mc, 2H), 6.92 (mc, 2H) | syn/anti mixture |
| I-a-40 | C$_2$H$_5$ | CH$_3$ | C$_2$H$_5$ | H | CH$_2$OCH$_2$OCH$_2$— | δ = 1.08 (mc, 6H), 2.31 (s, 3H), 3.23 (mc, 2H), 3.34 (s, 3H), 3.50 (d, 2H), 4.60 (s, 2H), 6.92 (mc, 2H) | syn/anti mixture |
| I-a-41 | C$_2$H$_5$ | CH$_3$ | C$_2$H$_5$ | H | CH$_3$CH(OH)— | 71-72° C. | syn/anti mixture racemate |
| I-a-42 | C$_2$H$_5$ | CH$_3$ | C$_2$H$_5$ | H | CH$_3$C(═NOCH$_3$)CH$_2$—CH$_2$— | 79-80° C. | E/Z mixture syn/anti mixture |
| I-a-43 | C$_2$H$_5$ | CH$_3$ | C$_2$H$_5$ | H | C$_2$H$_5$OCH$_2$— | δ = 1.08 (t, 6H), 1.19 (t, 3H), 3.15 (mc, 1H), 3.47 (mc, 3H), 3.48 (q, 2H), 6.92 (mc, 2H) | syn/anti mixture |
| I-a-44 | C$_2$H$_5$ | CH$_3$ | C$_2$H$_5$ | H | C$_6$H$_5$NH(C═O)OCH$_2$— | 101-102° C. | syn/anti mixture |

-continued

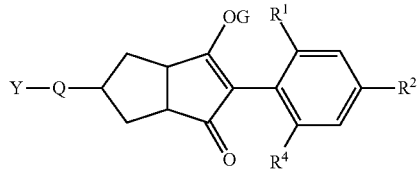
(I-a)

| Ex. No. | R1 | R2 | R4 | G | Y—Q | m.p. [° C.] or $^1$H-NMR (400 MHz, CDCl$_3$, δ in ppm) | Notes |
|---|---|---|---|---|---|---|---|
| I-a-45 | C$_2$H$_5$ | CH$_3$ | C$_2$H$_5$ | H | C$_2$H$_5$O$_2$C— | δ = 1.08 (mc, 6H), 1.25 (mc, 3H), 1.88 and 2.00 (in each case mc, Σ 2H), 2.99 (mc, 1H), 4.12 (q, 2H), 6.90 (mc, 2H) | syn/anti mixture |
| I-a-46 | C$_2$H$_5$ | CH$_3$ | C$_2$H$_5$ | H | CH$_3$(C=O)SCH$_2$— | δ = 1.08 (t, 6H), 2.30 (s, 3H), 2.34 (s, 3H), 2.95, (d, 2H), 3.22 (mc, 2H), 6.91 (mc, 2H) | syn/anti mixture |
| I-a-47 | C$_2$H$_5$ | CH$_3$ | C$_2$H$_5$ | H | C$_6$H$_5$CH$_2$NH(C=O)—OCH$_2$— | 101-102° C. | syn/anti mixture |
| I-a-48 | C$_2$H$_5$ | CH$_3$ | C$_2$H$_5$ | H | CH$_3$SO$_2$CH$_2$— | 180-181° C. | syn/anti mixture |
| I-a-49 | C$_2$H$_5$ | CH$_3$ | C$_2$H$_5$ | H | NCCH$_2$— | 66-67° C. | syn/anti mixture |
| I-a-50 | C$_2$H$_5$ | CH$_3$ | C$_2$H$_5$ | H | H$_2$N(C=O)— | 161-162° C. | syn/anti mixture |
| I-a-51 | C$_2$H$_5$ | CH$_3$ | C$_2$H$_5$ | H | H$_2$N(C=O)OCH$_2$— | 90-91° C. | syn/anti mixture |
| I-a-52 | C$_2$H$_5$ | CH$_3$ | C$_2$H$_5$ | H | (CH$_3$)$_2$N(C=O)OCH$_2$— | 151-152° C. | syn/anti mixture |
| I-a-53 | C$_2$H$_5$ | CH$_3$ | C$_2$H$_5$ | H | CH$_3$NH(C=O)— | δ = 1.10 (mc, 6H), 2.32 (s, 3H), 2.82 (mc, 1H), 3.49 (d, 3H), 6.95 (mc, 2H) | syn/anti mixture |
| I-a-54 | C$_2$H$_5$ | CH$_3$ | C$_2$H$_5$ | H | (acetyl morpholine structure) | 131-132° C. | syn/anti mixture |
| I-a-55 | C$_2$H$_5$ | CH$_3$ | C$_2$H$_5$ | H | (CH$_3$)$_2$N(C=O)— | 131-132° C. | syn/anti mixture |
| I-a-56 | C$_2$H$_5$ | CH$_3$ | C$_2$H$_5$ | benzyl | —CHO | δ = 1.08 and 1.12 (in each case t, in each case 3H), 2.72 and 2.90 (in each case mc, Σ 1H), 3.11 and 3.91 (in each case mc, in each case 1H), 4.71 and 4.77 (s and mc, Σ 1H), 6.90 (mc, 2H), 7.10-7.35 (m, 5H) | syn/anti mixture |
| I-a-57 | C$_2$H$_5$ | CH$_3$ | C$_2$H$_5$ | benzyl | CH$_3$C=O— | δ = 1.09 and 1.12 (in each case t, in each case 3H), 1.90 and 2.03 (in each case mc, in each case 1H), 2.80, 3.08 and 3.41 (in each case mc, in each case 1H), 4.78 and 4.80 (AB system, J = 12 Hz, 2H), | syn/anti mixture |
| I-a-58 | C$_2$H$_5$ | CH$_3$ | C$_2$H$_5$ | benzyl | CH$_3$O$_2$CCH=CH— | 90-91° C. | syn/anti mixture E/Z mixture |
| I-a-59 | C$_2$H$_5$ | CH$_3$ | C$_2$H$_5$ | benzyl | —CH=CHCN | δ = 1.10 (mc, 6H), 3.10-3.50 (m, 3H), 4.75-4.85 (m, 2H), 5.30 and 5.33, (in each case d, Σ 1H), 6.88 and 6.70 (in each case d, Σ 1H), 6.90 (mc, 2H) | syn/anti mixture E/Z mixture |
| I-a-60 | C$_2$H$_5$ | CH$_3$ | C$_2$H$_5$ | H | CH$_3$SCH$_2$— | δ = 1.08 (t, 6H), 2.10 (s, 3H), 2.29 (s, 3H), 2.20-2.42 (m, 4H), 3.25 (mc, 2H), 6.90 (mc, 2H) | syn/anti mixture |
| I-a-61 | C$_2$H$_5$ | CH$_3$ | C$_2$H$_5$ | benzyl | BrCH$_2$— | δ = 1.09 (mc, 6H), 1.51-1.70 (mc, 2H), 3.02 (mc, 1H), 3.40 (mc, 2H), 3.48 (mc, 1H), 4.79 (mc, 2H), 6.90 (mc, 2H) | syn/anti mixture |
| I-a-62 | C$_2$H$_5$ | CH$_3$ | C$_2$H$_5$ | benzyl | H$_2$N(C=O)OCH$_2$— | δ = 1.09 (mc, 6H), 1.38-1.65 (mc, 2H), 3.12 and 3.40 (in each case mc, in each case 1H), 4.05 (mc, 2H), 4.60 (s, br), 4.80 and 4.82 (in each case mc, Σ 2H), 6.90 (mc, 2H), 7.10-7.35 (m, 5H) | syn/anti mixture |
| I-a-63 | C$_2$H$_5$ | CH$_3$ | C$_2$H$_5$ | benzyl | C$_6$H$_5$NH(C=O)OCH$_2$— | 60-61° C. | syn/anti mixture |
| I-a-64 | C$_2$H$_5$ | CH$_3$ | C$_2$H$_5$ | benzyl | CF$_3$(C=O)OCH$_2$— | δ = 1.09 (mc, 6H), 1.38-1.62 (m, 2H), 2.33 (s, 3H), 3.10-3.70 (m, 3H), 4.80-4.91 (m, 2H), 6.90 (mc, 2H), 7.12-7.35 (m, 5H) | syn/anti mixture |
| I-a-65 | C$_2$H$_5$ | CH$_3$ | C$_2$H$_5$ | benzyl | (CH$_3$)$_2$N(C=O)— | 111-112° C. | syn/anti mixture |
| I-a-66 | C$_2$H$_5$ | CH$_3$ | C$_2$H$_5$ | H | (CH$_3$)$_3$C(C=O)SCH$_2$— | δ = 1.08 (mc, 6H), 1.21 (s, 9H), 2.30 (s, 3H), 2.92 (d, 2H), 3.12 and 3.35 (in each case mc, in each case 1H), 6.93 (mc, 2H), | syn/anti mixture |
| I-a-67 | C$_2$H$_5$ | CH$_3$ | C$_2$H$_5$ | H | CF$_3$(C=O)OCH$_2$— | 214-215° C. | syn/anti mixture |
| I-a-68 | C$_2$H$_5$ | CH$_3$ | C$_2$H$_5$ | H | CF$_3$CH(OH)— | 185-186° C. | syn/anti mixture |

-continued

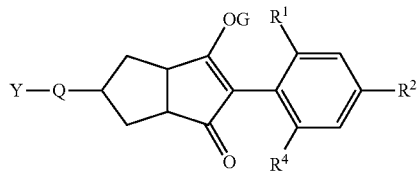

(I-a)

| Ex. No. | R1 | R2 | R4 | G | Y—Q | m.p. [° C.] or $^1$H-NMR (400 MHz, CDCl$_3$, δ in ppm) | Notes |
|---|---|---|---|---|---|---|---|
| I-a-69 | C$_2$H$_5$ | CH$_3$ | C$_2$H$_5$ | benzyl | CH$_2$=CH— | δ = 1.11 (mc, 6H), 1.40-1.69 (m, 2H), 3.00-3.15 (m, 1H), 3.38 (mc, 1H), 4.75-4.85 (m, 2H), 4.95-5.10 (m, 2H), 5.80 (mc, 1H), 6.90 (mc, 2H), 7.12-7.33 (m, 5H) | syn/anti mixture |
| I-a-70 | C$_2$H$_5$ | CH$_3$ | C$_2$H$_5$ | H | BrCH$_2$— | δ = 1.09 (mc, 6H), 1.40-1.55 (m, 2H), 2.30 (s, 3H), 2.60 (mc, 1H), 3.25 (mc, 1H), 3.48 (mc, 2H), 3.71 (mc, 1H), 6.90 (mc, 2H) | syn/anti mixture |
| I-a-71 | C$_2$H$_5$ | CH$_3$ | C$_2$H$_5$ | H | CH$_2$=CHCH$_2$—SCH$_2$— | δ = 1.07 (mc, 6H), 2.31 (s, 3H), 3.12 (d, 2H), 3.15-3.35 (m, 2H), 5.05-5.15 (mc, 2H), 5.55-5.62 (m, 1H), 6.90 (mc, 2H) | syn/anti mixture |
| I-a-72 | C$_2$H$_5$ | CH$_3$ | C$_2$H$_5$ | H | (CH$_3$)$_2$CHCH$_2$—SCH$_2$— | δ = 0.99 (mc, 6H), 1.07 (mc, 6H), 1.79 (hept, 1H), 2.40 (d, 2H), 2.55 (mc, 2H), 3.15-3.35 (m, 2H), 6.90 (mc, 2H) | syn/anti mixture |
| I-a-73 | C$_2$H$_5$ | CH$_3$ | C$_2$H$_5$ | H | oxazol-2-yl-SCH$_2$— | δ = 1.06 (mc, 6H), 1.31-1.55 (m, 2H), 2.30 (s, 3H), 2.55 (mc, 1H), 3.15-3.55 (m, 3H), 6.90 (d, 1H), 6.92 (mc, 2H), 7.10 (d, 1H) | syn/anti mixture |
| I-a-74 | C$_2$H$_5$ | CH$_3$ | C$_2$H$_5$ | H | (CH$_3$)$_2$CHCH$_2$—SO$_2$CH$_2$— | δ = 1.07 (mc, 6H), 1.12 (d, 6H), 2.75 (mc, 1H), 2.88 (d, 2H), 3.00 (mc, 1H), 3.15 (mc, 1H), 3.38 (mc, 1H), 6.92 (mc, 2H) | syn/anti mixture |
| I-a-75 | C$_2$H$_5$ | CH$_3$ | C$_2$H$_5$ | benzyl | CF$_3$CH(OH)— | 87-88° C. | syn/anti mixture |
| I-a-76 | C$_2$H$_5$ | CH$_3$ | C$_2$H$_5$ | H | benzoxazol-2-yl-OCH$_2$— | δ = 1.05 (mc, 6H), 2.50-2.85 (m, Σ 1H), 3.15-3.41 (m, 2H), 4.51, d, 2H), 6.93 (mc, 2H), 7.15-7.45 (m, 4H) | syn/anti mixture |
| I-a-77 | C$_2$H$_5$ | CH$_3$ | C$_2$H$_5$ | H | 4,5-dimethylthiazol-2-yl-OCH$_2$— | 73-74° C. | syn/anti mixture |
| I-a-78 | C$_2$H$_5$ | CH$_3$ | C$_2$H$_5$ | H | NCSCH$_2$— | 87-88° C. | syn/anti mixture |
| I-a-79 | C$_2$H$_5$ | CH$_3$ | C$_2$H$_5$ | H | tetrahydropyran-2-yl-OCH$_2$— | 74-75° C. | syn/anti mixture |
| I-a-80 | C$_2$H$_5$ | CH$_3$ | C$_2$H$_5$ | H | tetrahydrofuran-2-yl-SCH$_2$— | δ = 1.05 (mc, 6H), 1.88 (mc, 2H), 2.05 (mc, 1H), 2.60-2.71 (m, 4H), 3.05-3.36 (m, 2H), 3.60-4.00 (m, 4H), 6.93 (mc, 2H) | syn/anti mixture |
| I-a-81 | C$_2$H$_5$ | CH$_3$ | C$_2$H$_5$ | C$_2$H$_5$ | —CH$_2$CO$_2$C$_2$H$_5$ | δ = 1.05 (mc, 6H), 1.22 (t, 3H), 2.51 (mc, 1H), 3.20 (mc, 2H), 4.12 (q, 2H), 6.91 (mc, 2H) | syn/anti mixture |
| I-a-82 | C$_2$H$_5$ | CH$_3$ | C$_2$H$_5$ | benzyl | CH$_2$OCH$_2$— | | |

Example I-b-1

2-(2,6-Diethyl-4-methylphenyl)-5-(methoxyimino)methyl-3-oxo-3,3a,4,5,6,6a-hexahydropentalen-1-yl 2,2-dimethylpropanoate

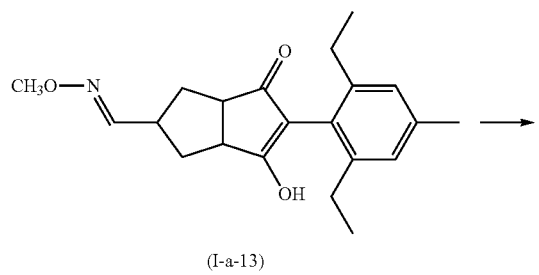

(I-a-13)

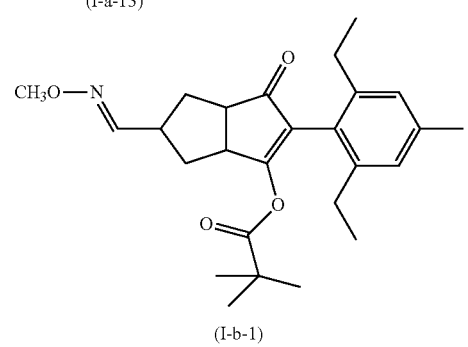

(I-b-1)

0.104 g (0.31 mmol) of 5-(2,6-diethyl-4-methylphenyl)-6-hydroxy-4-oxo-1,2,3,3a,4,6a-hexahydropentalene-2-carbaldehyde O-methyloxime (compound I-a-13 according to the invention), 0.040 g (0.34 mmol) of pivaloyl chloride and 92 mg (0.91 mmol) of triethylamine in 8 ml of dichloromethane are stirred at room temperature for 2 h. The mixture is poured onto ice, taken up in dichloromethane, washed with water, dried (magnesium sulphate) and concentrated using a rotary evaporator. Chromatography on silica gel (mobile phase ethyl acetate/hexane v:v=25:75) gives 107 mg of the title compound as a colourless oil.

$^1$H-NMR (400 MHz, CDCl$_3$): δ=1.04 and 1.09 (in each case t, in each case 3H), 1.08 (s, 9H), 2.98 (mc, 3H), 3.30 (mc, 1H), 3.80 (s, 3H), 4.00 (mc, 1H), 6.88 (s, 1H), 7.31 (d, J=7 Hz, —C$\underline{H}$=NOCH$_3$).

The following compounds of the formula (I-b) are obtained analogously to Example (I-b-1) and in accordance with the general statements on the preparation:

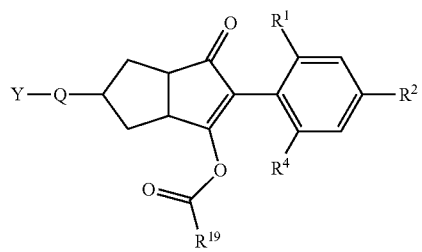

(I-b)

| Ex. No. | R$^1$ | R$^2$ | R$^4$ | R$^{19}$ | Y—Q | m.p. [° C.] or $^1$H-NMR (400 MHz, CDCl$_3$, δ in ppm) | Notes |
|---|---|---|---|---|---|---|---|
| I-b-2 | C$_2$H$_5$ | CH$_3$ | C$_2$H$_5$ | tBu | —CHO | δ = 1.10 (s, 9H), 2.98, 3.37 and 4.04 (in each case mc, in each case 1H), 9.66 (d, 1H, C$\underline{H}$O) | syn/anti mixture |
| I-b-3 | C$_2$H$_5$ | CH$_3$ | C$_2$H$_5$ | tBu | (1,3-dioxan-2-yl) | 127° C. | syn/anti mixture |
| I-b-4 | C$_2$H$_5$ | CH$_3$ | C$_2$H$_5$ | tBu | (1,3-dioxolan-2-yl) | δ = 1.05 (s, 9H), 1.42-1.58 (m, 3H), 3.22 (mc, 1H), 3.81-3.98 (m, 5H), 4.75 (d, 1H) | syn/anti mixture |
| I-b-5 | C$_2$H$_5$ | CH$_3$ | C$_2$H$_5$ | tBu | CH$_3$O—CH—OCH$_3$ | δ = 1.05 (s, 9H), 1.33-1.50 (m, 2H), 3.34 and 3.35 (in each case s, Σ 3H), 3.95 (mc, 1H), 4.18 (d, 1H), 6.86 (s, 2H) | syn/anti mixture |
| I-b-6 | C$_2$H$_5$ | CH$_3$ | C$_2$H$_5$ | tBu | C$_3$H$_5$CH$_2$O—N=CH— | δ = 0.25 and 0.52 (in each case mc, in each case 2H), 1.08 (s, 9H), 3.28 (mc, 1H), 3.82 and 3.89 (in each case d, Σ2H, C$\underline{H}_2$C$_3$H$_5$), 4.00 (mc, 1H), 6.59 and 7.38 (in each case d, Σ2H, C$\underline{H}$=NO) | E/Z mixture syn/anti mixture |
| I-b-7 | C$_2$H$_5$ | CH$_3$ | C$_2$H$_5$ | tBu | Cl$_2$C=CHCH$_2$O—N=CH— | δ = 1.04 (s, 9H), 2.30 (s, 3H), 3.28 and 4.02 (in each case mc, in each case 1H), 4.60 and 4.67 (in each case d, Σ 2H), 6.10 (mc, 1H), 6.88 (s, 2H) | E/Z mixture syn/anti mixture |

-continued

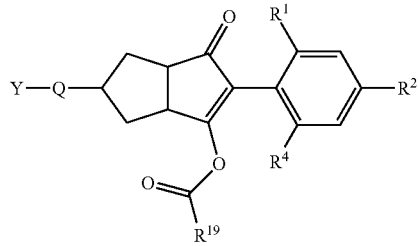
(I-b)

| Ex. No. | R¹ | R² | R⁴ | R¹⁹ | Y—Q | m.p. [° C.] or ¹H-NMR (400 MHz, CDCl₃, δ in ppm) | Notes |
|---|---|---|---|---|---|---|---|
| I-b-8 | $C_2H_5$ | $CH_3$ | $C_2H_5$ | tBu | $CH_2$=$CHCH_2O$—N=CH— | δ = 1.05 (s, 9H), 3.28 and 4.00 (in each case mc, in each case 1H), 4.50-4.61 (m, 2H), 5.18-5.32 (m, 2H), 5.96 (mc, 1H), 6.51 and 7.39 (in each case d, Σ 1H) | E/Z mixture syn/anti mixture |
| I-b-9 | $C_2H_5$ | $CH_3$ | $C_2H_5$ | tBu | HC≡$CCH_2O$—N=CH— | δ = 1.00-1.11 (m, 15H), 2.45 (mc, 1H), 3.00 and 3.52 (in each case mc, Σ 1H), 3.28 and 4.00 (in each case mc, in each case 1H), 4.60 and 4.67 (in each case d, Σ 2H), 6.70 and 7.40 (in each case d, Σ 1H) | E/Z mixture syn/anti mixture |
| I-b-10 | $C_2H_5$ | $CH_3$ | $C_2H_5$ | iPr | (7-membered dioxepine with CH=CH) | δ = 1.00-1.11 (m, 12H), 2.56 (hept, 1H), 3.15 and 3.92 (in each case mc, in each case 1H), 4.18 and 4.40 (in each case mc, in each case 2H), 4.55 and 4.58 (in each case d, Σ 1H) | syn/anti mixture |
| I-b-11 | $C_2H_5$ | $CH_3$ | $C_2H_5$ | tBu | (7-membered dioxepane) | δ = 1.00 (t, 6H), 1.15 (s, 9H), 2.28 (s, 3H), 3.61 and 4.09 (in each case s, in each case 2H), 4.48 and 4.51 (in each case d, Σ 1H) | syn/anti mixture |
| I-b-12 | $C_2H_5$ | $CH_3$ | $C_2H_5$ | tBu | (dimethyl dioxane) | 99-100° C. | syn/anti mixture |
| I-b-13 | $C_2H_5$ | $CH_3$ | $C_2H_5$ | iPr | $CH_3O$—N=CH— | δ = 1.00-1.12 (m, 12H), 2.31 (s, 3H), 3.81 and 3.87 (in each case s, Σ 1H), 4.00 (mc, 1H), 6.59 and 7.32 (in each case s, Σ 1H), | E/Z mixture syn/anti mixture |
| I-b-14 | $C_2H_5$ | $CH_3$ | $C_2H_5$ | $C_2H_5$ | $CH_3O$—N=CH— | δ = 1.02-1.11 (m, 9H), 2.33 (s, 3H), 3.18-3.30 (m, 1H), 3.80 and 3.86 (in each case s, Σ 1H), 3.98-4.08 (m, 1H), 6.59 and 7.31 (in each case s, Σ 1H), 6.90 (s, 2H) | E/Z mixture syn/anti mixture |
| I-b-15 | $C_2H_5$ | $CH_3$ | $C_2H_5$ | iPr | (dimethyl dioxane) | δ = 0.70 and 1.12 (in each case s, in each case 3H), 1.02 and 1.08 in each case mc, in each case 6H), 2.57 (hept, 1H), 3.40 and 3.58 (in each case mc, in each case 2H), 4.30 and 4.35 (in each case d, Σ 1H), 6.89 (mc, 2H) | syn/anti mixture |
| I-b-16 | $C_2H_5$ | $CH_3$ | $C_2H_5$ | iPr | $CH_3O$–CH($CH_3O$)– | δ = 1.02 and 1.08 (in each case mc, in each case 6H), 2.58 (hept, 1H), 3.33 (mc, 6H), 4.18 and 4.20 (in each case d, Σ 1H), 6.99 (s, 2H) | syn/anti mixture |
| I-b-17 | $C_2H_5$ | $CH_3$ | $C_2H_5$ | $C_2H_5$ | $CH_3O$–CH($CH_3O$)– | δ = 1.03-1.12 (m, 9H), 2.31 (s, 3H), 2.52 (mc, 1H), 3.30-3.35 (m, 6H), 3.92-4.04 (m, 1H), 4.19 (mc, 1H), 6.90 (m, 2H) | syn/anti mixture |
| I-b-18 | $C_2H_5$ | $CH_3$ | $C_2H_5$ | tBu | (1,3-dithiane) | δ = 1.00 (t, 6H), 1.21 (s, 9H), 2.28 (s, 3H), 3.21 and 3.92 (in each case mc, in each case 1H), 4.03 and 4.09 (in each case d, Σ 1H), 6.85 (mc, 2H) | syn/anti mixture |
| I-b-19 | $C_2H_5$ | $CH_3$ | $C_2H_5$ | tBu | (1,3-oxathiane) | δ = 1.00 and 1.08 (in each case t, Σ 6H), 1.09 (s, 9H), 1.91 (mc, 2H), 3.05-3.19 (m, 1H), 3.35-4.47 (m, 1H), 4.12 (mc, 2H) | syn/anti mixture |

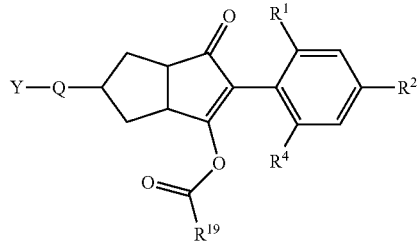

(I-b)

| Ex. No. | R¹ | R² | R⁴ | R¹⁹ | Y—Q | m.p. [° C.] or ¹H-NMR (400 MHz, CDCl₃, δ in ppm) | Notes |
|---|---|---|---|---|---|---|---|
| I-b-20 | C₂H₅ | CH₃ | C₂H₅ | iPr | (1,3-dithian-2-yl) | 133-134° C. | syn/anti mixture |
| I-b-21 | C₂H₅ | CH₃ | C₂H₅ | iPr | (1,3-dithiolan-2-yl) | δ = 1.00-1.11 (m, 9H), 2.52 (hept, 1H), 3.15-3-25 (m, 5H), 3.90-4.01 (m, 1H), 4.48 and 4.50 (in each case d, Σ1H), 6.87 (s, 2H) | syn/anti mixture |
| I-b-22 | C₂H₅ | CH₃ | C₂H₅ | tBu | (1,3-dithiolan-2-yl) | δ = 1.03 (t, 6H), 1.06 (s, 9H), 3.15-3.26 (m, 5H), 3.90-4.00 (m, 1H), 4.48-4.51 (m, 1H), 6.86 (s, 2H) | syn/anti mixture |
| I-b-23 | C₂H₅ | CH₃ | C₂H₅ | iPr | CH₃(C=O)OCH₂— | δ = 1.03 (mc, 6H), 1.10 (mc, 6H), 2.05 (s, 3H), 2.30 (s, 3H), 3.15-3.29 (m, 1H), 3.93-4.10 (m, 3H), 6.89 (s, 2H) | syn/anti mixture |
| I-b-24 | C₂H₅ | CH₃ | C₂H₅ | tBu | BrCH₂— | 106-107° C. | syn/anti mixture |
| I-b-25 | C₂H₅ | CH₃ | C₂H₅ | tBu | EtO₂C-(3-methyl-4,5-dihydroisoxazol-5-yl) | δ = 1.04 (mc, 6H), 1.07 (s, 9H), 1.30 (t, 3H), 3.12 (mc, 1H), 3.21 (d, 2H), 3.30 (mc, 1H), 4.03 (mc, 1H), 4.23 (q, 2H), 6.88 (mc, 2H) | syn/anti mixture |
| I-a-26 | C₂H₅ | CH₃ | C₂H₅ | iPr | C₆H₅NH(C=O)OCH₂— | δ = 1.00-1.11 (mc, 12H), 1.30-1.62 (m, 2H), 2.59 (mc, 2H), 3.26 (mc, 1H), 3.95-4.04 (m, 1H), 4.16 (d, 2H), 6.89 (mc, 2H), 7.08 (mc, 1H), 7.25-7.40 (m, 4H) | syn/anti mixture |
| I-b-27 | C₂H₅ | CH₃ | C₂H₅ | iPr | C₆H₅CH₂NH(C=O)OCH₂— | δ = 1.01-1.11 (mc, 12H), 1.22-1.60 (m, 2H), 2.48-2.60 (m, 2H), 3.15-3.29 (m, 1H), 3.90-4.04 (m, 1H), 4.11 (d, 2H), 4.38 (mc, 2H), 6.89 (mc, 2H), 7.08 (mc, 1H), 7.25-7.40 (m, 4H) | syn/anti mixture |
| I-b-28 | C₂H₅ | CH₃ | C₂H₅ | tBu | (oxazol-2-yl)-SCH₂— | δ = 1.05 (mc, 6H), 1.07 (s, 9H), 2.28 (s, 3H), 2.61 (mc, 1H), 3.20-3.33 (m, 3H), 6.89 (mc, 2H), 7.25-7.38 (m, 5H) | syn/anti mixture |

Example I-c-1

2-(2,6-Diethyl-4-methylphenyl)-5-(dimethoxymethyl)-3-oxo-3,3a,4,5,6,6a-hexahydropentalen-1-yl ethyl carbonate

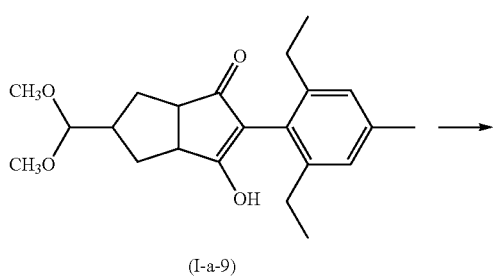

(I-a-9)

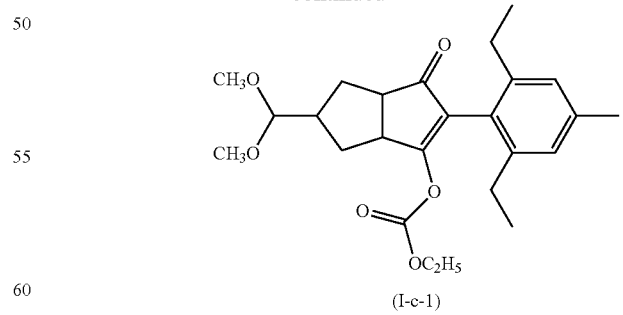

(I-c-1)

At room temperature, 80 mg (0.80 mmol) of trimethylamine are added dropwise to 0.090 g (0.25 mmol) of 2-(2,6-diethyl-4-methylphenyl)-5-(dimethoxymethyl)-3-hydroxy-4,5,6,6a-tetrahydropentalen-1(3aH)-one (compound I-a-9 according to the invention) and 30 mg (0.28 mmol) of ethyl chloroformate in 15 ml of dichloromethane, and the mixture is stirred for another 1 h. The mixture is poured onto ice-water, taken up in dichloromethane, washed with water, dried (magnesium sulphate), and the solvent is distilled off.

Chromatographic purification on silica gel (ethyl acetate/hexane=1:4) gives 88 mg (81%) of the desired compound in the form of colourless crystals of melting point 95-96° C.

$^1$H-NMR (400 MHz, CDCl$_3$): δ=1.06, 1.10 and 1.25 (in each case t, in each case 3H), 1.40-1.50 (m, 2H), 2.18 (mc, 1H), 2.53 (mc, 1H), 3.21 (mc, 1H), 3.32 (s, 6H), 4.02 (mc, 1H), 4.18 (q, 2H), 6.90 (mc, 1H) ppm The following compounds of the formula (I-c) are obtained analogously to Examples (I-c-1) according to the general statements on the preparation:

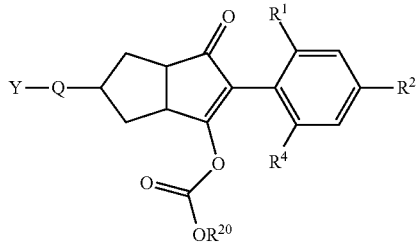

(I-c)

| Ex. No. | R$^1$ | R$^2$ | R$^4$ | R$^{20}$ | Y—Q | m.p. [° C.] or $^1$H-NMR (400 MHz, CDCl$_3$, δ in ppm) | Notes |
|---|---|---|---|---|---|---|---|
| I-c-2 | C$_2$H$_5$ | CH$_3$ | C$_2$H$_5$ | C$_2$H$_5$ | (4,7-dihydro-1,3-dioxepin-2-yl) | δ = 1.05 (mc, 6H), 1.24 (t, 3H), 3.15 and 3.24 (mc, 1H), 4.00 (mc, 1H), 4.18 (mc, 4H), 4.33-4.43 (m, 2H), 4.55 and 4.58 (in each case d, Σ 1H), 5.70 (s, 2H), 6.90 (s, 2H) | syn/anti mixture |
| I-c-3 | C$_2$H$_5$ | CH$_3$ | C$_2$H$_5$ | C$_2$H$_5$ | (1,3-dioxepan-2-yl) | δ = 1.07 (mc, 6H), 1.25 (t, 3H), 3.61 and 3.88 (in each case mc, in each case 2H), 4.00 (mc, 1H), 4.19 (mc, 2H) 4.48 and 4.51 (in each case d, Σ 1H), 6.90 (s, 2H) | syn/anti mixture |
| I-c-4 | C$_2$H$_5$ | CH$_3$ | C$_2$H$_5$ | C$_2$H$_5$ | (5,5-dimethyl-1,3-dioxan-2-yl) | δ = 0.70 (s, 3H), 1.08 (mc, 6H), 1.12 (s, 3H), 1.24 (t, 3H), 3.22 (mc, 1H), 3.40 and 3.58 (in each case d, in each case 2H), 4.18 (mc, 2H), 4-30 (d, 1H), 6.90 (mc, 2H) | syn/anti mixture |
| I-c-5 | C$_2$H$_5$ | CH$_3$ | C$_2$H$_5$ | C$_2$H$_5$ | $^i$PrO—N=CH— | δ = 1.05-1.12 (m, 3H), 1.18-1.28 (m, 6H), 3.00 (mc, 1H), 4.00-4.32 (m. 4H), 6.58 and 7.31 (in each case d, Σ 1H), | E/Z mixture syn/anti mixture |
| I-c-6 | C$_2$H$_5$ | CH$_3$ | C$_2$H$_5$ | C$_2$H$_5$ | Cl$_2$C=CHCH$_2$O—N=CH— | δ = 1.10 (mc, 6H), 1.25 (mc, 3H), 3.00 (mc, 1H), 4.05 (mc, 1H), 4.20 (mc, 2H), 4.60 and 4.66 (in each case d, Σ 2H), 6.10 (mc, 1H), 6.63 and 7.45 (in each case d, Σ 1H) | E/Z mixture syn/anti mixture |
| I-c-7 | C$_2$H$_5$ | CH$_3$ | C$_2$H$_5$ | C$_2$H$_5$ | C$_3$H$_5$CH$_2$O—N=CH— | δ = 0.25 and 0.53 (in each case mc, in each case 2H), 1.10 (mc, 6H), 1.24 (mc, 3H), 3.28 (mc, 1H), 3.33 and 3.39 (in each case d, Σ 2H), 4.19 (mc, 2H), 6.60 and 7.38 (in each case d, Σ 1H), 6.90 (mc, 2H) | E/Z mixture syn/anti mixture |
| I-c-8 | C$_2$H$_5$ | CH$_3$ | C$_2$H$_5$ | C$_2$H$_5$ | CH$_2$=CHCH$_2$O—N=CH— | δ = 1.10 (mc, 6H), 1.21 (mc, 3H), 4.05 (mc, 1H), 4.20 (mc, 2H), 4.50 and 4.50 (in each case d, Σ 1H), 5.90-6.02 (m, 1H), 6.61 and 7.48 (in each case d, Σ 1H) | E/Z mixture syn/anti mixture |
| I-c-9 | C$_2$H$_5$ | CH$_3$ | C$_2$H$_5$ | CH$_3$ | (CH$_3$O)$_2$CH— | δ = 1.05-1.10 (m, 6H), 2.31 (s, 3H), 3.15-3.28 (m, 1H), 3.35 (mc, 6H), 3.79 (s, 3H), 4.03 (mc, 1H), 4.18 and 4.20 (in each case d, Σ 1H) | syn/anti mixture |
| I-c-10 | C$_2$H$_5$ | CH$_3$ | C$_2$H$_5$ | iPr | (CH$_3$O)$_2$CH— | δ = 1.05-1.12 (m, 6H), 1.21-1.27 (m, 6H), 3.30-3.35 (m, 6H), 4.02 (mc, 1H), 4.18 and 4.21 (in each case d, Σ 1H), 4.82 (hept, 1H), 6.90 (mc, 2H) | syn/anti mixture |
| I-c-11 | C$_2$H$_5$ | CH$_3$ | C$_2$H$_5$ | C$_2$H$_5$ | (1,3-dithian-2-yl) | δ = 1.25 (mc, 3H), 2.80-2.92 (m, 4H), 3.12-3.26 (m, 1H), 3.97-4.21 (m, 4H), 6.90 (s, 2H) | syn/anti mixture |
| I-c-12 | C$_2$H$_5$ | CH$_3$ | C$_2$H$_5$ | C$_2$H$_5$ | (1,3-oxathian-2-yl) | δ = 1.08 (mc, 6H), 1.24 (mc, 3H), 2.75, 3.01, 3.58 (in each case mc, in each case 1H), 4.10-4.22 (m, 3H), 4.69 (mc, 1H), 6.89 (s, 2H) | syn/anti mixture |

-continued

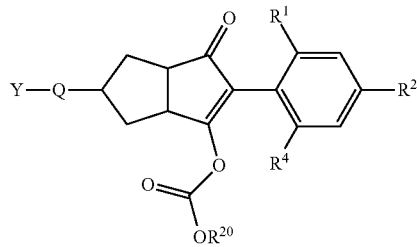

(I-c)

| Ex. No. | $R^1$ | $R^2$ | $R^4$ | $R^{20}$ | Y—Q | m.p. [° C.] or $^1$H-NMR (400 MHz, CDCl$_3$, δ in ppm) | Notes |
|---|---|---|---|---|---|---|---|
| I-c-13 | $C_2H_5$ | $CH_3$ | $C_2H_5$ | $C_2H_5$ | (2-methyl-1,3-dithiolane) | δ = 1.24 (mc, 3H), 3.25 (mc, 5H), 4.00 (mc, 1H), 4.18 (mc, 2H), 4.48 and 4.50 (in each case d, Σ 1H), 6.90 (mc, 2H) | syn/anti mixture |
| I-c-14 | $C_2H_5$ | $CH_3$ | $C_2H_5$ | iPr | $CH_3O$—N=CH— | δ = 1.09 (mc, 6H), 1.23 (mc, 6H), 1.48-1.64 (m, 2H), 3.28 (mc, 1H), 3.81 and 3.82 (in each case s, Σ 3H), 4.05 (mc, 1H), 4.81 (mc, 1H), 6.60 and 7.31 (in each case d, Σ 1H), 6.90 (mc, 2H) | E/Z mixture syn/anti mixture |
| I-c-15 | $C_2H_5$ | $CH_3$ | $C_2H_5$ | $C_2H_5$ | $CH_3(C=O)OCH_2$— | δ = 1.08 (mc, 6H), 1.25 (mc, 3H), 1.31-1.45 (m, 2H), 2.05 and 2.06 (in each case s, Σ 3H), 2.30 (s, 3H), 3.18-3.30 (m, 1H), 4.03 (mc, 3H), 4.20 (mc, 1H), 6.9 (mc, 2H) | syn/anti mixture |
| I-c-16 | $C_2H_5$ | $CH_3$ | $C_2H_5$ | $C_2H_5$ | —$CH_2CO_2C_2H_5$ | δ = 1.08 (mc, 6H), 1.22-1.35 (m, 6H), 2.28-2.45 (m, 8H), 2.30 (s, 3H), 2.85 (mc, 1H), 3.26 (mc, 1H), 4.03 (q, 1H), 4.14 (q, 2H), 4.18 (mc, 1H), 6.90 (mc, 2H) | syn/anti mixture |
| I-c-17 | $C_2H_5$ | $CH_3$ | $C_2H_5$ | $C_2H_5$ | $CH_3C=O$— | δ = 1.06 (mc, 6H), 1.23 (mc, 3H), 2.00 (mc, 2H), 2.20 (s, 3H), 2.31 (s, 3H), 2.82 (mc, 1H), 3.22 (mc, 1H), 4.03 (mc, 1H), 4.18 (mc, 1H), 6.92 (mc, 2H) | syn/anti mixture |
| I-c-18 | $C_2H_5$ | $CH_3$ | $C_2H_5$ | $C_2H_5$ | $CH_3C(=NOCH_3)$— | δ = 1.09 (mc, 6H), 1.25 (t, 3H), 1.81 (s, 3H) 1.93 (mc, 2H), 2.09 (mc, 1H), 2.59 (mc, 2H), 3.20 (mc, 1H), 3.81 (s, 3H), 1.71 (mc, 2H), 2.31 (s, 3H), 3.20 (mc, 1H), 3.81 (s, 3H), 4.03 (mc, 1H), 4.18 (mc, 2H) | E/Z mixture syn/anti mixture |
| I-c-19 | $C_2H_5$ | $CH_3$ | $C_2H_5$ | $C_2H_5$ | —$CH_2CH_2CO_2CH_3$ | δ = 1.08 (mc, 6H), 1.23 (mc, 3H), 1.71 (mc, 2H), 2.31 (s, 3H), 3.12-3.25 (m, 1H), 3.66 and 3.67 (in each case s, Σ 3H), 3.97 (mc, 1H), 4.19 (mc, 2H), 6.90 (mc, 2H) | syn/anti mixture |
| I-c-20 | $C_2H_5$ | $CH_3$ | $C_2H_5$ | iPr | —$CH_2CH_2CO_2CH_3$ | δ = 1.07 (mc, 6H), 1.09 (mc, 3H), 1.70 (mc, 2H), 2.31 (s, 3H), 2.57 (hept, 1H), 3.10-3.25 (m, 1H), 3.67 and 3.68 (in each case s, Σ 3H), 3.88-3.95 (m, 1H), 6.90 (mc, 2H) | syn/anti mixture |
| I-c-21 | $C_2H_5$ | $CH_3$ | $C_2H_5$ | $C_2H_5$ | —$CH_2CH_2CN$ | δ = 1.08 (mc, 6H), 1.22 (mc, 3H), 2.33, 1.78 (mc, 2H), (s, 3H), 3.12-3.30 (m, 1H), 4.00 (mc, 1H), 4.18 (mc, 2H), 6.88 (mc, 2H) | syn/anti mixture |
| I-c-22 | $C_2H_5$ | $CH_3$ | $C_2H_5$ | $C_2H_5$ | —CH=CHCN | δ = 1.08 (mc, 6H), 1.24 (mc, 3H), 1.65-1.80 (m, 2H), 2.31 (s, 3H), 3.20-3.29 (m, 1H), 4.05 (mc, 1H), 4.18 (mc, 2H), 5.45 (J = 13 Hz, 1H), 6.77 (dd, J = 13 and 5 Hz, 1H), 6.90 (mc, 2H) | syn/anti mixture E-isomer |
| I-c-23 | $C_2H_5$ | $CH_3$ | $C_2H_5$ | $C_2H_5$ | $CH_3(C=O)CH_2CH_2$— | δ = 1.08 (mc, 6H), 1.25 (mc, 3H), 2.23 and 2.24 (in each case s, Σ 3H), 2.31 (s, 3H), 3.10-3.23 (m, 1H), 3.95 (mc, 1H), 4.19 (mc, 2H), 6.90 (mc, 2H) | syn/anti mixture |
| I-c-24 | $C_2H_5$ | $CH_3$ | $C_2H_5$ | $C_2H_5$ | $CH_3(C=NOCH_3)CH_2CH_2$— | δ = 1.07 (mc, 6H), 1.26 (mc, 3H), 1.80 and 1.83 (in each case s, Σ 3H), 3.22-3.25 (m, 1H), 3.30 and 3.32 (in each case s, Σ 3H), 3.98 (mc, 1H), 4.20 (mc, 2H), 6.90 (mc, 2H) | E/Z mixture syn/anti mixture |
| I-c-25 | $C_2H_5$ | $CH_3$ | $C_2H_5$ | $C_2H_5$ | $C_6H_5CH_2NH(C=O)OCH_2$— | δ = 1.07 (mc, 6H), 1.25 (mc, 3H), 2.52 (mc, 1H), 3.15-3.29 (m, 1H), 4.03 (mc, 1H), 4.11 (mc, 2H), 4.19 (mc, 2H), 4.38 (mc, 2H), 6.90 (mc, 2H), 7.08 (mc, 1H), 7.24-7.38 (m, 5H) | syn/anti mixture |
| I-c-26 | $C_2H_5$ | $CH_3$ | $C_2H_5$ | $C_2H_5$ | $C_6H_5NH(C=O)OCH_2$— | δ = 1.08 (mc, 6H), 1.25 (t, 3H), 2.60 (mc, 1H), 3.18-3.31 (m, 1H), 4.05 (mc, 1H), 4.11-4.22 (m, 4H), 6.89 (mc, 2H), 7.08 (mc, 1H), 7.25-7.40 (m, 4H) | syn/anti mixture |
| I-c-27 | $C_2H_5$ | $CH_3$ | $C_2H_5$ | $C_2H_5$ | $H_2N(C=O)$— | 72-73° C. | syn/anti mixture |
| I-c-28 | $C_2H_5$ | $CH_3$ | $C_2H_5$ | $C_2H_5$ | $H_2N(C=O)OCH_2$— | δ = 1.09 (mc, 6H), 1.26 (t, 3H), 2.55 (mc, 1H), 3.15-3.30 (m, 1H), 4.05 (mc, 1H), 4.07 (d, 2H), 4.20 (mc, 2H), 4.60 (s, br, 2H), 6.90 (mc, 2H) | syn/anti mixture |
| I-c-29 | $C_2H_5$ | $CH_3$ | $C_2H_5$ | $C_2H_5$ | $(CH_3)_2N(C=O)$— | δ = 1.10 (mc, 6H), 1.24 (t, 3H), 2.32 (s, 3H), 2.95 (s, 3H), 3.06 (s, 3H), 3.25 (mc, 2H), 4.00-4.25 (m, 3H), 6.90 (mc, 2H) | syn/anti mixture |
| I-c-30 | $C_2H_5$ | $CH_3$ | $C_2H_5$ | $C_2H_5$ | $CH_2=CHCH_2$—$SCH_2$— | δ = 1.09 (mc, 6H), 1.25 (t, 3H), 2.32 (s, 3H), 3.12 (d, 2H), 3.22 (mc, 1H), 4.00 (mc, 1H), 4.20 (mc, 2H), 4.90 (mc, 2H), 3.72-3.83 (m, 1H), 6.90 (mc, 2H) | syn/anti mixture |

Example 1

1. Herbicidal Pre-Emergence Action

Seeds of monocotylidonous and dicotylidonous weed and crop plants are placed in sandy loam in wood fibre pots and covered with soil. The test compounds, formulated in the form of wettable powders (WP), are then, as an aqueous suspension with a water application rate of 600 l/ha (converted), with 0.2% of wetting agent added, applied to the surface of the covering soil in different amounts.

After the treatment, the pots are placed in a greenhouse and kept under good growth conditions for the test plants. The visual assessment of the emergence damage on the test plants is carried out after a trial period of three weeks by comparison with the untreated controls (herbicidal effect in percent: 100% effect=the plants have died, 0% effect=like control plants).

2. Herbicidal Post-Emergence Action

Seeds of monocotylidonous and dicotylidonous weed and crop plants are placed in sandy loam in wood fibre pots, covered with soil and cultivated in a greenhouse under good growth conditions. Two to three weeks after sowing, the test plants are treated at the one-leaf stage. The test compounds, formulated as wettable powders (WP), are then with a water application rate of 600 l/ha (converted), with 0.2% of wetting agent added, sprayed onto the green parts of the plants in different amounts. After the test plants have been kept in the greenhouse under optimum growth conditions for about three weeks, the effect of the preparations is assessed visually in comparison to untreated controls (herbicidal effect in percent: 100% effect=the plants have died, 0% effect=like control plants).

Post-Emergence, 80 g/ha

| Example | ALOMY | AVEFA | ECHCG | LOLMU | SETVI | POLCO | VERPE |
|---|---|---|---|---|---|---|---|
| I-a-4 | 50 | 90 | 100 | 60 | 100 | | |
| I-a-5 | 100 | 100 | 100 | 100 | 100 | | |
| I-a-7 | 100 | 70 | 100 | 100 | 80 | | |
| I-a-9 | 100 | 90 | 100 | 100 | 100 | | |
| I-a-10 | 100 | 100 | 100 | 100 | 100 | | |
| I-a-12 | 100 | 100 | 100 | 100 | 100 | | |
| I-a-13 | 100 | 100 | 100 | 100 | 100 | | |
| I-a-22 | 100 | 100 | 100 | 100 | 100 | | |
| I-a-23 | 70 | 60 | 100 | 90 | 100 | | |
| I-a-30 | | | 90 | 90 | 90 | | |
| I-a-31 | 90 | 80 | 90 | 90 | 100 | | |
| I-a-32 | | | 80 | 90 | 90 | | |
| I-a-33 | 100 | 100 | 100 | 100 | 90 | | |
| I-a-34 | 100 | | 100 | 100 | 90 | | |
| I-a-37 | 100 | 100 | 100 | 100 | 100 | | 80 |
| I-a-38 | | 90 | 90 | 90 | 90 | | |
| I-a-39 | 100 | | 100 | 100 | 100 | | |
| I-a-40 | 100 | 90 | | 100 | 90 | 100 | |
| I-a-41 | 100 | 100 | 100 | 100 | 100 | | |
| I-a-42 | 90 | 100 | 100 | 100 | 100 | | |
| I-a-60 | 90 | 90 | 100 | 90 | 90 | | |
| I-a-61 | | | 90 | 90 | 90 | | |
| I-a-79 | 90 | 100 | 100 | 100 | 90 | | 100 |
| I-a-81 | 80 | | 80 | 80 | 90 | | |
| I-b-1 | 100 | 100 | 100 | 100 | 100 | | |
| I-b-2 | | | 100 | | 100 | | |
| I-b-3 | 100 | | 100 | 100 | | | |
| I-b-23 | 80 | 90 | 100 | 90 | 90 | | |
| I-b-4 | 100 | 90 | 100 | 100 | 100 | | |
| I-b-5 | 100 | 100 | 100 | 100 | 100 | | |
| I-c-14 | 100 | 100 | 100 | 100 | 100 | | |
| I-c-15 | | | 90 | 90 | 80 | | |
| I-c-16 | | | 80 | | 80 | | |
| I-c-17 | 90 | 90 | 90 | 100 | 80 | | |
| I-c-18 | 100 | 80 | 90 | 100 | | | |
| I-c-21 | | 100 | 100 | 100 | 90 | | |
| I-c-22 | 80 | 100 | 100 | | 100 | | 90 |
| I-c-24 | 90 | 80 | 100 | 100 | 100 | | |

Post-Emergence, 100 g/ha

| Example | APESV | AVEFA | PHAMI | POAAN | SETVI |
|---|---|---|---|---|---|
| I-c-1 | 100 | 80 | 99 | 85 | 97 |

Pre-Emergence, 320 g/ha

| Example | ALOMY | AVEFA | ECHCG | LOLMU | SETVI | STEME | VERPE | VIOTR |
|---|---|---|---|---|---|---|---|---|
| I-a-4 | | | 100 | | 90 | | | |
| I-a-5 | 100 | 90 | | 100 | 90 | | | |
| I-a-7 | | 80 | 100 | 100 | | | | |
| I-a-9 | 100 | 80 | 100 | 100 | 90 | | | |

-continued

| Example | ALOMY | AVEFA | ECHCG | LOLMU | SETVI | STEME | VERPE | VIOTR |
|---|---|---|---|---|---|---|---|---|
| I-a-10 | 100 | 90 | 100 | 100 | 100 | | | 90 |
| I-a-12 | 100 | 80 | 100 | 100 | | | | |
| I-a-13 | | 80 | | 100 | | 100 | 90 | 100 |
| I-a-22 | 100 | 90 | 100 | 100 | 100 | | | |
| I-a-23 | | | 100 | | 90 | | | |
| I-b-1 | 100 | 90 | 100 | 100 | 100 | | | 90 |
| I-b-2 | 80 | 80 | 100 | 100 | 90 | | | |
| I-b-3 | 100 | 90 | 100 | 100 | 100 | | | 90 |
| I-b-4 | 100 | 90 | 100 | 100 | 100 | | | 90 |
| I-b-5 | 100 | 100 | 100 | 100 | 90 | | | |

LOLMU = *Lolium multiflorum*
ALOMY = *Alopecurus myosuroides*
AVEFA = *Avena fatua*
SETVI = *Setaria viridis*
ECHCG = *Echinochloa crus-galli*
STEME = *Stellaria media*
APESV = *Apera spica-venti*
PHAMI = *Phalaris minor*
POAAN = *Poa annua*
VERPE = *Veronica persica*
VIOTR = *Viola tricolor*
POLCO = *Polygonum convolvulus*

Example 2

*Tetranychus* Test OP-Resistant

TETRUR Spray Treatment

Solvents: 78.0 parts by weight of acetone
1.5 parts by weight of dimethylformamide
Emulsifier: 0.5 part by weight of alkylaryl polyglycol ether To produce a suitable preparation of active compound, one part by weight of active compound is mixed with the stated amounts of solvents and emulsifier, and the concentrate is diluted with emulsifier-containing water to the desired concentration.

Discs of common bean leaves (*Phaseolus vulgaris*) which are infested by all stages of the common two-spotted spider mite (*Tetranychus urticae*) are sprayed with an active compound preparation of the desired concentration.

After six days, the effect in percent is determined 100% means that all spider mites have been killed; 0% means that none of the spider mites have been killed.

In this test, for example, the following compounds of the Preparation Examples show an effect of 80% at an application rate of 100 g/ha:
I-c-19, I-c-21

In this test, for example, the following compounds of the Preparation Examples show an effect of 90% at an application rate of 100 g/ha:
I-a-4, I-a-5, I-a-6, I-a-13, I-a-14, I-a-15, I-a-20, I-a-30, I-a-57, I-a-40, I-a-47, I-a-71, I-a-72, I-a-74, I-b-7, I-b-23, I-b-24, I-b-27, I-c-2, I-c-15, I-c-16, I-c-25, I-c-29

In this test, for example, the following compounds of the Preparation Examples show effect of 100% at an application rate of 100 g/ha:
I-a-8, I-a-32, I-b-6, I-b-8, I-b-9, I-b-10, I-c-5, I-c-14, I-c-30

Example 3

Phaedon Test

PHAECO Spray Treatment

Solvents: 78.0 parts by weight of acetone
1.5 parts by weight of dimethylformamide
Emulsifier: 0.5 part by weight of alkylaryl polyglycol ether To produce a suitable preparation of active compound, one part by weight of active compound is mixed with the stated amounts of solvents and emulsifier, and the concentrate is diluted with emulsifier-containing water to the desired concentration.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the effect in % is determined 100% means that all beetle larvae have been killed; 0% means that none of the beetle larvae have been killed.

In this test, for example, the following compounds of the Preparation Examples show an effect of 100% at an application rate of 500 g/ha: I-a-44, I-a-47

Example 4

Myzus Test

MYZUPE Spray Treatment

Solvents: 78 parts by weight of acetone
1.5 parts by weight of dimethylformamide
Emulsifier: 0.5 part by weight of alkylaryl polyglycol ether To produce a suitable preparation of active compound, one part by weight of active compound is mixed with the stated amounts of solvents and emulsifier, and the concentrate is diluted with emulsifier-containing water to the desired concentration.

Discs of Chinese cabbage leaves (*Brassica pekinensis*) which are infested by all stages of the green peach aphid (*Myzus persicae*) are sprayed with an active compound preparation of the desired concentration.

After 6 days, the effect in % is determined 100% means that all aphids have been killed; 0% means that none of the aphids have been killed.

In this test, for example, the following compounds of the Preparation Examples show an effect of 100% at an application rate of 500 g/ha: I-a-59, I-c-22

The invention claimed is:
1. A compound of formula (I)

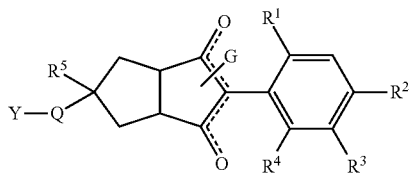

wherein the following isomeric forms can be included:

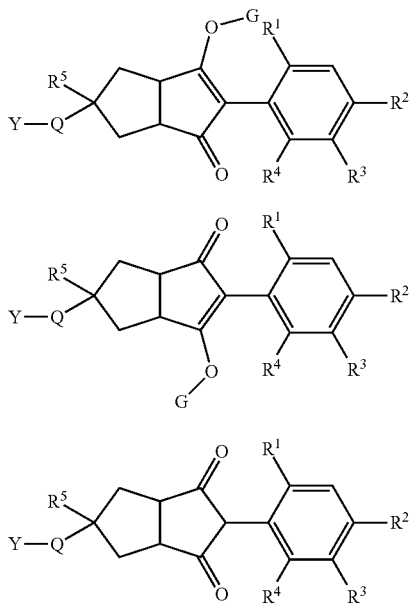

in which
Q represents a bond, a $C_1$-$C_3$-alkylene, a $C_2$-$C_3$-alkenylene or a $C_2$-$C_3$-alkynylene chain,
Y represents the groups —$OR^6$, —$S(O)_pR^6$, —$CO_2R^7$, —CH=$CH_2$, cyano, —SCN, —$CONR^8R^9$, —$SO_2NR^8R^9$, —$CR^{10}$=O, —$NR^{11}R^{12}$, —$CR^{10}$=N—$OR^{13}$, —$CR^{10}$=N—$R^{14}$, $CR^{10}$=N—$NR^{15}R^{16}$, —$CR^{10}(OR^{17}OR^{18})$, —$CR^{10}(SR^{17}OR^{18})$, —$CR^{10}(SR^{17}SR^{18})$, —$CR^{10}(NHR^{17}NHR^{18})$, —$CR^{10}(NHR^{17}OR^{18})$, —$CR^{10}(NHR^{17}SR^{18})$, —$CH(CN)_2$, —$CH(OH)R^6$, halogen, —$O(C=M)R^{10}$, —$S(C=M)R^{10}$, —$O(C=M)NR^{11}R^{12}$, —$S(C=M)NR^{11}R^{12}$, —NH$(C=M)NR^{11}R^{12}$, —$O(C=M)OR^7$, —$S(C=M)OR^7$, —$NH(C=M)OR^7$ or represents the group W,
or Q, Y and $R^5$ together form one of the groups CHCN=, $CH(CO_2C_1$-$C_6$-alkyl)=,

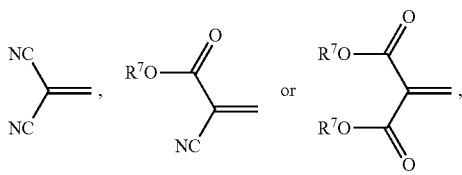

W represents a 3- to 7-membered saturated or partially saturated heterocycle which contains at least one heteroatom optionally oxygen, sulphur or nitrogen and may additionally be mono- or polysubstituted by identical or different substituents, G represents hydrogen, methyl, ethyl or benzyl (a) or represents one of the groups

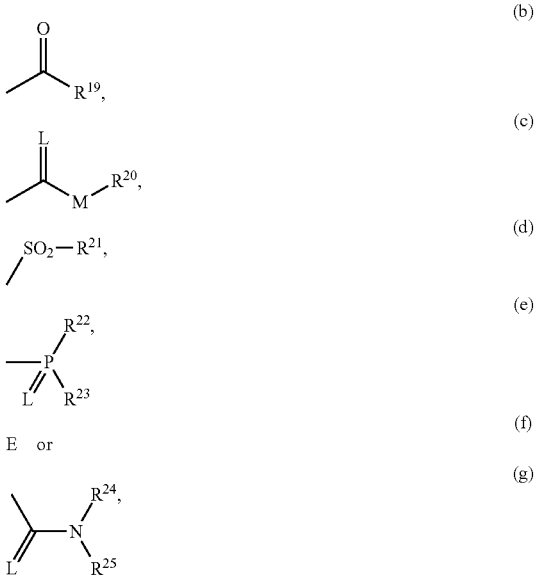

E represents a metal ion equivalent, a tertiary sulphonium ion or an ammonium ion,
L represents oxygen or sulphur,
M represents oxygen or sulphur,
$R^1$ represents hydrogen, halogen, cyano, nitro, $C_1$-$C_6$-alkyl, halo-$C_1$-$C_6$-alkyl, $C_3$-$C_6$-cycloalkyl, halo-$C_3$-$C_6$-cycloalkyl, $C_2$-$C_6$-alkenyl, halo-$C_2$-$C_6$-alkenyl, $C_2$-$C_6$-alkynyl, halo-$C_2$-$C_6$-alkynyl, $C_1$-$C_6$-alkoxy, halo-$C_1$-$C_6$-alkoxy, $C_3$-$C_6$-cycloalkoxy, halo-$C_3$-$C_6$-cycloalkoxy, $C_2$-$C_6$-alkynyloxy, halo-$C_2$-$C_6$-alkynyloxy, $C_2$-$C_6$-alkenyloxy, halo-$C_2$-$C_6$-alkenyloxy, $C_1$-$C_3$-alkylthio, $C_1$-$C_3$-alkylsulphinyl, $C_1$-$C_3$-alkylsulphonyl, halo-$C_1$-$C_3$-alkylthio, halo-$C_1$-$C_3$-alkylsulphinyl or halo-$C_1$-$C_3$-alkylsulphonyl,
$R^2$ and $R^3$ independently of one another are identical or different and represent hydrogen, halogen, cyano, nitro, $C_1$-$C_6$-alkyl, halo-$C_1$-$C_6$-alkyl, $C_2$-$C_6$-alkenyl, halo-$C_2$-$C_6$-alkenyl, $C_2$-$C_6$-alkynyl, halo-$C_2$-$C_6$-alkynyl, $C_1$-$C_6$-alkoxy, halo-$C_1$-$C_6$-alkoxy, $C_3$-$C_6$-cycloalkyl, $C_3$-$C_6$-cycloalkoxy, halo-$C_3$-$C_6$-cycloalkoxy, $C_2$-$C_6$-alkynyloxy, halo-$C_2$-$C_6$-alkynyloxy, $C_2$-$C_6$-alkenyloxy, halo-$C_2$-$C_6$-alkenyloxy, $C_1$-$C_3$-alkylthio, $C_1$-$C_3$-alkylsulphinyl, $C_1$-$C_3$-alkylsulphonyl, halo-$C_1$-$C_3$-alkylthio, halo-$C_1$-$C_3$-alkylsulphinyl, halo-$C_1$-$C_3$-alkylsulphonyl, phenyl or phenyl which is optionally mono- or polysubstituted by identical or different substituents from the group consisting of halogen, $C_1$-$C_4$-alkyl, halo-$C_1$-$C_4$-alkyl, $C_3$-$C_6$-cycloalkyl, halo-$C_3$-$C_6$-cycloalkyl, $C_1$-$C_6$-alkoxy, halo-$C_1$-$C_6$-alkoxy, nitro and cyano,
$R^4$ represents hydrogen, halogen, cyano, nitro, $C_1$-$C_6$-alkyl, halo-$C_1$-$C_6$-alkyl, $C_3$-$C_6$-cycloalkyl, halo-$C_3$-$C_6$-cycloalkyl, $C_1$-$C_6$-alkoxy, halo-$C_1$-$C_6$-alkoxy, $C_3$-$C_6$-cycloalkoxy, or halo-$C_3$-$C_6$-cycloalkoxy,
$R^5$ represents hydrogen or $C_1$-$C_4$-alkyl, $R^6$ represents hydrogen, $C_1$-$C_6$-alkyl, halo-$C_1$-$C_6$-alkyl, $C_3$-$C_6$-cycloalkyl, halo-$C_3$-$C_6$-cycloalkyl, $C_2$-$C_6$-alkenyl, halo-$C_2$-$C_6$-alkenyl, $C_2$-$C_6$-alkynyl, halo-$C_2$-$C_6$-alkynyl, $C_1$-$C_4$-alkoxy-$C_1$-$C_4$-alkyl, halo-$C_1$-$C_4$-alkoxy-$C_1$-$C_4$-alkyl, $C_3$-$C_6$-cycloalkoxy-$C_1$-$C_4$-alkyl, halo-$C_3$-$C_4$-cycloalkoxy-$C_1$-$C_4$-alkyl, represents benzyl, phenyl, heteroaryl, —$CH_2$-heteroaryl, —$CH_2CH_2$-heteroaryl, pyranyl, tetrahydrofuranyl, $C_1$-$C_4$-alkanoyl, halo-$C_1$-$C_4$-alkanoyl, benzoyl, each of which is optionally mono- or polysubstituted by identical or different substituents from the group consisting of halogen, cyano, nitro, $C_1$-$C_6$-alkyl, halo-$C_1$-$C_6$-alkyl, $C_3$-$C_6$-cycloalkyl, halo-$C_3$-$C_6$-cycloalkyl, halo-$C_2$-$C_6$-alkenyl, $C_2$-$C_6$-alkynyl, halo-$C_2$-$C_6$-alkynyl, $C_1$-$C_4$-alkoxyalkyl, halo-$C_1$-$C_4$-alkoxy-$C_1$-$C_6$-alkyl, $C_3$-$C_6$-cycloalkoxy-$C_1$-$C_6$-alkyl and halo-$C_3$-$C_6$-cycloalkoxy-$C_1$-$C_6$-alkyl, or represents benzoyl, which is optionally mono- or polysubstituted by identical or different substituents from the group consisting of halogen, cyano, nitro, $C_1$-$C_6$-alkyl, halo-$C_1$-$C_6$-alkyl, $C_3$-$C_6$-cycloalkyl and halo-$C_3$-$C_6$-cycloalkyl, $R^7$ represents hydrogen, represents in each case optionally substituted $C_1$-$C_6$-alkyl, $C_3$-$C_6$-cycloalkyl, $C_2$-$C_6$-alkenyl or represents a cation E, $R^8$ and $R^9$ independently of one another are identical or different and represent hydrogen, $C_1$-$C_6$-alkyl, $C_2$-$C_6$-alkenyl, $C_2$-$C_6$-alkynyl, $C_3$-$C_6$-cycloalkyl, phenyl, benzyl, represent phenyl or benzyl, each of which is mono- or polysubstituted by identical or different substituents from the group consisting of halogen, nitro, cyano and $C_1$-$C_3$-alkyl or $R^8$ and $R^9$ together with the adjacent nitrogen atom form a morpholino, piperidino or pyrrolidino group, $R^{10}$ represents hydrogen, $C_1$-$C_6$-alkyl, halo-$C_1$-$C_4$-alkyl, $C_2$-$C_6$-alkenyl, halo-$C_2$-$C_6$-alkenyl, $C_2$-$C_6$-alkynyl, $C_3$-$C_6$-cycloalkyl, represents phenyl or benzyl, each of which is optionally mono- or polysubstituted by identical or different substituents from the group consisting of halogen, $C_1$-$C_6$-alkyl and halo-$C_1$-$C_6$-alkyl, $R^{11}$ and $R^{12}$ independently of one another are identical or different and represent hydrogen, $C_1$-$C_6$-alkyl, $C_2$-$C_6$-alkenyl, $C_2$-$C_6$-alkynyl, $C_3$-$C_6$-cycloalkyl, phenyl, benzyl, represent phenyl or benzyl, each of which is mono- or polysubstituted by identical or different substituents from the group consisting of halogen, nitro, cyano and $C_1$-$C_3$-alkyl or $R^{11}$ and $R^{12}$ together with the adjacent nitrogen atom form a morpholino, piperidino or pyrrolidino group, $R^{13}$ represents hydrogen or represents $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_3$-alkyl, each of which is optionally interrupted at least once by oxygen or sulphur and is optionally mono- or polysubstituted by halogen, represents benzyl or —$CH_2$-heterocyclyl, each of which is optionally mono- or polysubstituted by identical or different substituents from the group consisting of halogen, nitro, cyano and $C_1$-$C_3$-alkyl, $R^{14}$ represents hydrogen, $C_1$-$C_6$-alkyl, halo-$C_1$-$C_6$-alkyl, $C_2$-$C_6$-alkenyl, halo-$C_2$-$C_6$-alkenyl, $C_2$-$C_6$-alkynyl, halo-$C_2$-$C_6$-alkynyl, phenyl, benzyl or represents phenyl or benzyl, each of which is mono- or polysubstituted by identical or different substituents from the group consisting of halogen, $C_1$-$C_3$-alkyl, halo-$C_1$-$C_3$-alkyl, $C_3$-$C_6$-cycloalkyl, halo-$C_3$-$C_6$-cycloalkyl, nitro and cyano, $R^{15}$ and $R^{16}$ independently of one another are identical or different and represent hydrogen, $C_1$-$C_5$-alkyl, $C_2$-$C_6$-alkenyl, $C_2$-$C_6$-alkynyl, $C_3$-$C_6$-cycloalkyl, phenyl, benzyl, represent phenyl or benzyl, each of which is mono- or polysubstituted by identical or different substituents from the group consisting of halogen, nitro, cyano and $C_1$-$C_3$-alkyl or $R^{15}$ and $R^{16}$ together with the adjacent nitrogen atom form a morpholino, piperidino or pyrrolidino group, $R^{17}$ represents hydrogen, represents $C_1$-$C_6$-alkyl, benzyl or halo-$C_1$-$C_6$-alkyl, each of which is optionally interrupted at least once by identical or different radicals from the group consisting of oxygen and sulphur, $R^{18}$ represents hydrogen, represents $C_1$-$C_6$-alkyl, benzyl or halo-$C_1$-$C_6$-alkyl, each of which is optionally interrupted at least once by identical or different radicals from the group consisting of oxygen and sulphur, $R^{19}$ represents optionally halogen-substituted $C_1$-$C_6$-alkyl, $C_2$-$C_6$-alkenyl, $C_1$-$C_4$-alkoxy-$C_1$-$C_4$alkyl, $C_1$-$C_3$-alkylthio-$C_1$-$C_4$-alkyl, poly-$C_1$-$C_4$-alkoxy-$C_1$-$C_4$-alkyl or represents $C_3$-$C_6$-cycloalkyl which is optionally mono- or polysubstituted by identical or different substituents from the group consisting of halogen, $C_1$-$C_4$-alkyl and $C_1$-$C_4$-alkoxy and may optionally be interrupted in the ring by oxygen or sulphur, represents phenyl, phenyl-$C_1$-$C_4$-alkyl, hetaryl, phenoxy-$C_1$-$C_4$-alkyl or hetaryloxy-$C_1$-$C_4$-alkyl, each of which is optionally substituted by halogen or $C_1$-$C_4$-alkyl, $R^{20}$ represents $C_1$-$C_6$-alkyl, $C_2$-$C_6$-alkenyl, $C_1$-$C_4$-alkoxy-$C_1$-$C_4$-alkyl, poly-$C_1$-$C_4$-alkoxy-$C_1$-$C_4$-alkyl, each of which is optionally mono- or polysubstituted by identical or different halogen, or represents $C_3$-$C_6$-cycloalkyl which may optionally be interrupted in the ring by oxygen or sulphur, or represents benzyl, $R^{21}$, $R^{22}$ and $R^{23}$ independently of one another are identical or different and represent $C_1$-$C_6$-alkyl, $C_1$-$C_6$-alkoxy, $C_1$-$C_6$-alkylamino, $C_1$-$C_6$-dialkylamino, $C_1$-$C_3$-alkylthio, $C_2$-$C_4$-alkenylthio, $C_3$-$C_6$-cycloalkylthio, each of which is optionally mono- or polysubstituted by identical or different halogen, or represent phenyl, benzyl, phenoxy or phenylthio, $R^{24}$ and $R^{25}$ independently of one another are identical or different and represent hydrogen, represent $C_1$-$C_6$-alkyl, $C_3$-$C_6$-cycloalkyl, $C_2$-$C_6$-alkenyl, $C_1$-$C_6$-alkoxy, $C_1$-$C_6$-alkoxy-$C_1$-$C_4$-alkyl, each of which is optionally mono- or polysubstituted by identical or different halogen, represent phenyl or benzyl, optionally mono- or polysubstituted by identical or different substituents from the group consisting of halogen and $C_1$-$C_4$-alkyl or $R^{24}$ and $R^{25}$ together with the adjacent nitrogen atom form a morpholino, piperidino or pyrrolidino group, P represents the number 0, 1 or 2, or if Q, Y and $R^5$ together represent the group $CH_2$=, then G represents methyl, ethyl or benzyl (a).

2. The compound of formula (I) according to claim 1, in which

Q represents a bond, a $C_1$-$C_3$-alkylene, a $C_2$-$C_3$-alkenylene or a $C_2$-$C_3$-alkynylene chain, Y represents the groups —$OR^6$, —$S(O)_pR^6$, —$CO_2R^7$, —$CH=CH_2$, cyano, —$SCN$, —$CONR^8R^9$, —$SO_2NR^8R^9$, —$CR^{10}$=O, —$NR^{11}R^{12}$, —$CR^{10}$=N—$OR^{13}$, —$CR^{10}$=N—$R^{14}$, $CR^{10}$=N—$NR^{15}R^{16}$, —$CR^{10}(OR^{17}OR^{18})$, —$CR^{10}(SR^{17}OR^{18})$, —$CR^{10}(SR^{17}SR^{18})$, —$CR^{10}(NHR^{17}NHR^{18})$, —$CR^{10}(NHR^{17}OR^{18})$, —$CR^{10}(NHR^{17}SR^{18})$, —$CH(CN)_2$, —$CH(OH)R^6$, halogen, —$O(C=M)R^{10}$, —$S(C=M)R^{10}$, —$O(C=M)NR^{11}R^{12}$, —$S(C=M)NR^{11}R^{12}$, —$NH(C=M)NR^{11}R^{12}$, —$O(C=M)OR^7$, —$S(C=M)OR^7$, —NH(C=m)OR$^7$ or represents the group W, or Q, Y and R$^5$ together form one of the groups CHCN=, CH(CO$_2$C$_1$-C$_6$-alkyl)=,

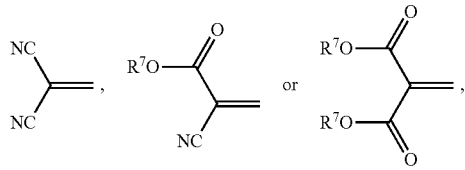

W represents one of the 3- to 7-membered saturated or partially saturated heterocycles listed below, which may be attached in various ways and may be mono- or polysubstituted by identical or different substituents from the group consisting of R$^{31}$ and R$^{32}$

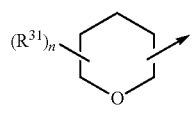 W$_1$

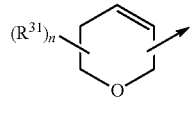 W$_2$

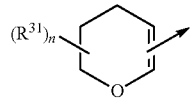 W$_3$

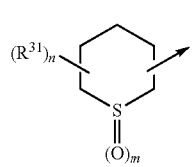 W$_4$

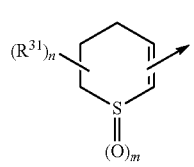 W$_5$

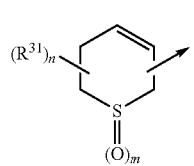 W$_6$

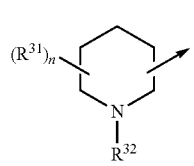 W$_7$

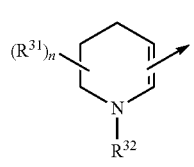 W$_8$

-continued

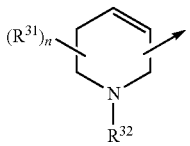 W$_9$

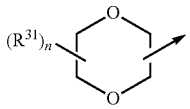 W$_{10}$

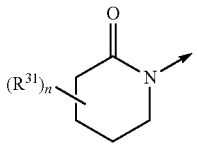 W$_{11}$

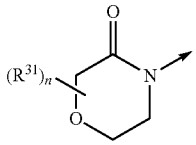 W$_{12}$

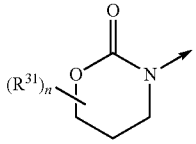 W$_{13}$

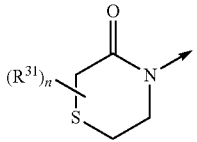 W$_{14}$

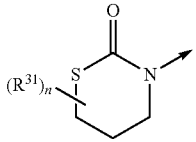 W$_{15}$

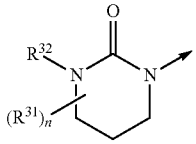 W$_{16}$

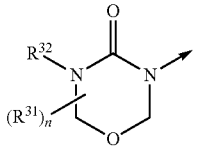 W$_{17}$

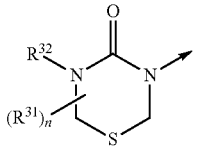 W$_{18}$

| | | |
|---|---|---|
| W19 | 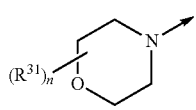 | W31 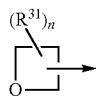 |
| W20 | 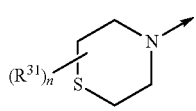 | W32 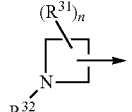 |
| W21 | 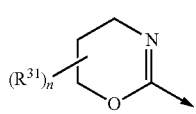 | W33 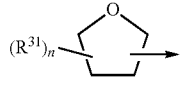 |
| W22 | 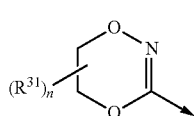 | W34 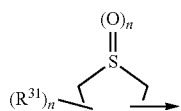 |
| W23 | 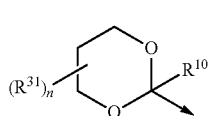 | W35 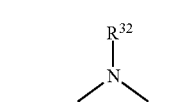 |
| W24 | 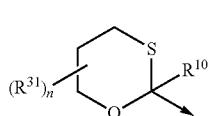 | W36 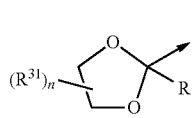 |
| W25 | 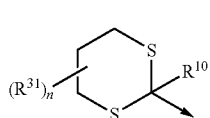 | W37 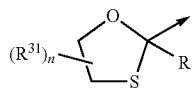 |
| W26 | 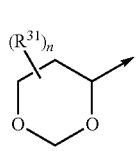 | W38 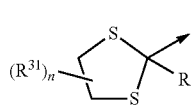 |
| W27 | 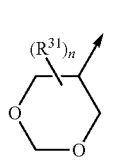 | W39 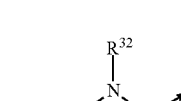 |
| W28 | 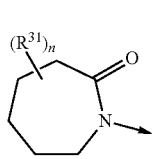 | W40 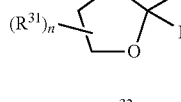 |
| W29 | 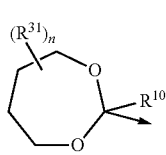 | W41 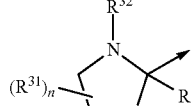 |
| W30 | 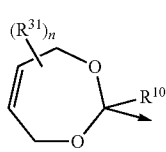 | W42 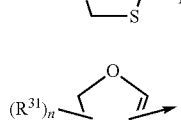 |
| | | W43 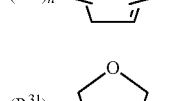 |

121
-continued
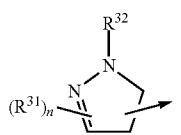  W44
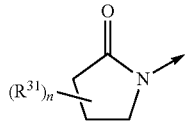  W45
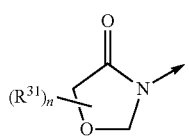  W46
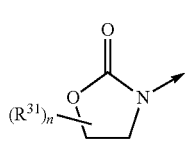  W47
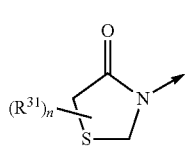  W48
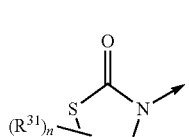  W49
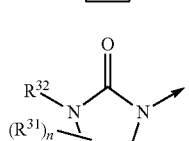  W50
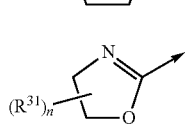  W51
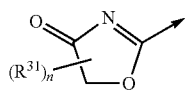  W52
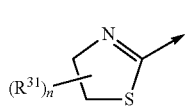  W53
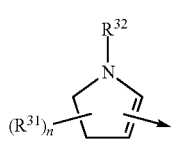  W54
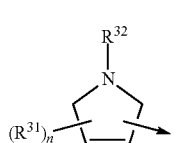  W55
122
-continued
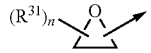  W56
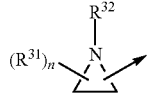  W57
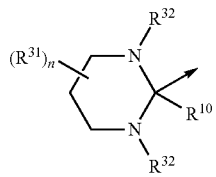  W58
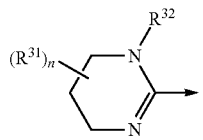  W59
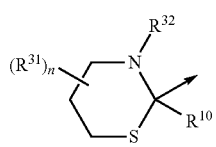  W60
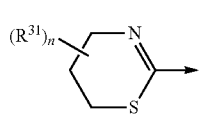  W61
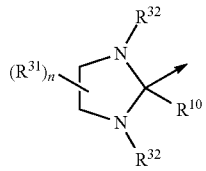  W62
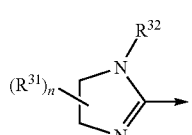  W63
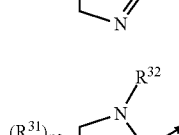  W64
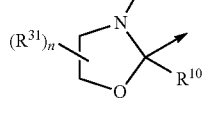  W65
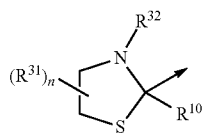  W66
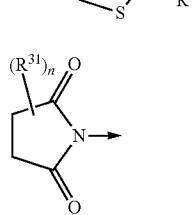

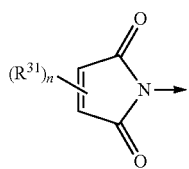

W<sub>67</sub>

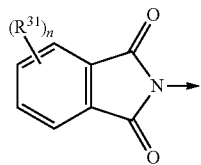

W<sub>68</sub>

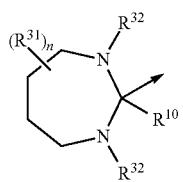

W<sub>69</sub>

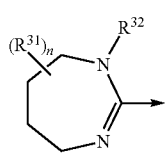

W<sub>70</sub>

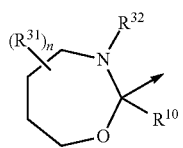

W<sub>71</sub>

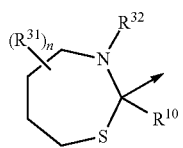

W<sub>72</sub>

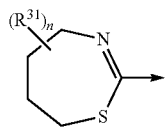

W<sub>73</sub>

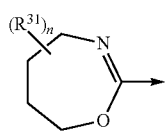

W<sub>74</sub>

G represents hydrogen, methyl, ethyl or benzyl (a) or represents one of the groups

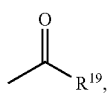
(b)

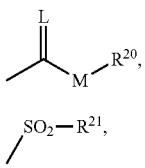
(c)

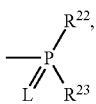
(d)

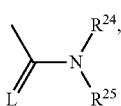
(e)

E or (f)

(g)

E represents a metal ion equivalent, a tertiary sulphonium ion or an ammonium ion, L represents oxygen or sulphur, M represents oxygen or sulphur, $R^1$ represents hydrogen, halogen, $C_1$-$C_4$-alkyl, halo-$C_1$-$C_4$-alkyl, $C_3$-$C_6$-cycloalkyl, halo-$C_3$-$C_6$-cycloalkyl, $C_2$-$C_4$-alkenyl, halo-$C_2$-$C_4$-alkenyl, $C_2$-$C_4$-alkynyl, halo-$C_2$-$C_4$-alkynyl, $C_1$-$C_4$-alkoxy, halo-$C_1$-$C_4$-alkoxy, $C_2$-$C_4$-alkynyloxy, halo-$C_2$-$C_4$-alkynyloxy, $C_2$-$C_4$-alkenyloxy, halo-$C_2$-$C_4$-alkenyloxy, $C_1$-$C_3$-alkylthio, $C_1$-$C_3$-alkylsulphinyl, $C_1$-$C_3$-alkylsulphonyl, halo-$C_1$-$C_3$-alkylthio, halo-$C_1$-$C_3$-alkylsulphinyl or halo-$C_1$-$C_3$-alkylsulphonyl, $R^2$ and $R^3$ independently of one another are identical or different and represent hydrogen, halogen, $C_1$-$C_4$-alkyl, halo-$C_1$-$C_4$-alkyl, $C_2$-$C_4$-alkenyl, halo-$C_2$-$C_4$-alkenyl, $C_2$-$C_4$-alkynyl, halo-$C_2$-$C_4$-alkynyl, $C_1$-$C_4$-alkoxy, halo-$C_1$-$C_4$-alkoxy, $C_3$-$C_6$-cycloalkyl, $C_3$-$C_6$-cycloalkoxy, halo-$C_3$-$C_6$-cycloalkoxy, $C_2$-$C_4$-alkynyloxy, halo-$C_2$-$C_4$-alkynyloxy, $C_2$-$C_4$-alkenyloxy, halo-$C_2$-$C_4$-alkenyloxy, $C_1$-$C_3$-alkylthio, $C_1$-$C_3$-alkylsulphinyl, $C_1$-$C_3$-alkylsulphonyl, halo-$C_1$-$C_3$-alkylthio, halo-$C_1$-$C_3$-alkylsulphinyl, halo-$C_1$-$C_3$-alkylsulphonyl, phenyl or phenyl which is optionally mono- or polysubstituted by identical or different substituents from the group consisting of halogen, $C_1$-$C_4$-alkyl, halo-$C_1$-$C_4$-alkyl, $R^4$ represents hydrogen, halogen, $C_1$-$C_4$-alkyl, halo-$C_1$-$C_4$-alkyl, $C_3$-$C_6$-cycloalkyl, halo-$C_3$-$C_6$-cycloalkyl, $C_1$-$C_4$-alkoxy, halo-$C_1$-$C_4$-alkoxy, $C_3$-$C_4$-cycloalkoxy, or halo-$C_3$-$C_6$-cycloalkoxy, $R^5$ represents hydrogen or $C_1$-$C_4$-alkyl, $R^6$ represents hydrogen, $C_1$-$C_4$-alkyl, halo-$C_1$-$C_4$-alkyl, $C_3$-$C_6$-cycloalkyl, halo-$C_3$-$C_6$-cycloalkyl, $C_2$-$C_4$-alkenyl, halo-$C_2$-$C_4$-alkenyl, $C_2$-$C_4$-alkynyl, halo-$C_2$-$C_4$-alkynyl, $C_1$-$C_4$-alkoxy-$C_1$-$C_4$-alkyl, halo-$C_1$-$C_4$-alkoxy-$C_1$-$C_4$-alkyl, $C_3$-$C_6$-cycloalkoxy-$C_1$-$C_4$-alkyl, halo-$C_3$-$C_4$-cycloalkoxy-$C_1$-$C_4$-alkyl, represents benzyl, phenyl, heteroaryl, —CH$_2$-heteroaryl, —CH$_2$CH$_2$-heteroaryl, $C_1$-$C_4$-alkanoyl, halo-$C_1$-$C_4$-alkanoyl, benzoyl, each of which is optionally mono- or polysubstituted by identical or different substituents from the group consisting of halogen, cyano, nitro, $C_1$-$C_4$-alkyl, halo-$C_1$-$C_4$-alkyl, $C_3$-$C_6$-cycloalkyl, halo-$C_3$-$C_6$-cycloalkyl, halo-$C_2$-$C_4$-alkenyl, $C_2$-$C_4$-alkynyl, halo-$C_2$-$C_4$-alkynyl, $C_1$-$C_4$-alkoxyalkyl, halo-$C_1$-$C_4$-alkoxy-$C_1$-$C_6$-alkyl, $C_3$-$C_6$-cycloalkoxy-$C_1$-$C_6$-alkyl and halo-$C_3$-$C_6$-cycloalkoxy-$C_1$-$C_6$-alkyl, or represents benzoyl which is optionally mono- or polysubstituted by identical or different substituents from the group consisting of halogen, cyano, nitro, $C_1$-$C_4$-alkyl, halo-$C_1$-$C_4$-alkyl, $C_3$-$C_6$-cycloalkyl and halo-$C_3$-$C_6$-cycloalkyl, $R^7$ represents hydrogen, represents $C_1$-$C_4$-alkyl, $C_3$-$C_6$-cycloalkyl, $C_2$-$C_4$-alkenyl, each of which is optionally mono- or polysubstituted by identical or different substituents from the group consisting of halogen and $C_1$-$C_4$-alkoxy, or represents a cation E, $R^8$ and $R^9$ independently of one another are identical or different and represent hydrogen, $C_1$-$C_4$-alkyl, $C_2$-$C_4$-alkenyl, $C_2$-$C_4$-alkynyl, $C_3$-$C_6$-cycloalkyl, phenyl, benzyl, represent phenyl or benzyl, each of which is mono- or polysubstituted by identical or different substituents from the group consisting of halogen, nitro, cyano and $C_1$-$C_3$-alkyl or $R^8$ and $R^9$ together with the adjacent nitrogen atom form a morpholino, piperidino or pyrrolidino group, $R^{10}$ represents hydrogen, $C_1$-$C_4$-alkyl, halo-$C_1$-$C_4$-alkyl, $C_2$-$C_4$-alkenyl, halo-$C_2$-$C_4$-alkenyl, $C_2$-$C_4$-alkynyl, $C_3$-$C_6$-cycloalkyl, represents phenyl or benzyl, each of which is optionally mono- or polysubstituted by identical or different substituents from the group consisting of halogen, $C_1$-$C_4$-alkyl and halo-$C_1$-$C_4$-alkyl, $R^{11}$ and $R^{12}$ independently of one another are identical or different and represent hydrogen, $C_1$-$C_4$-alkyl, $C_2$-$C_4$-alkenyl, $C_2$-$C_4$-alkynyl, $C_3$-$C_6$-cycloalkyl, phenyl, benzyl, represent phenyl or benzyl, each of which is mono- or polysubstituted by identical or different substituents from the group consisting of halogen and $C_1$-$C_3$-alkyl or $R^{11}$ and $R^{12}$ together with the adjacent nitrogen atom form a morpholino, piperidino or pyrrolidino group, $R^{13}$ represents hydrogen or represents $C_1$-$C_4$-alkyl, $C_2$-$C_4$-alkenyl, $C_2$-$C_4$-alkynyl, $C_3$-$C_4$-cycloalkyl, $C_3$-$C_6$-cycloalkyl-$C_1$-$C_3$-alkyl, each of which is optionally mono- or polysubstituted by halogen, represents benzyl or —$CH_2$-heterocyclyl, each of which is optionally mono- or polysubstituted by identical or different substituents from the group consisting of halogen and $C_1$-$C_3$-alkyl, $R^{14}$ represents hydrogen, $C_1$-$C_4$-alkyl, halo-$C_1$-$C_4$-alkyl, $C_2$-$C_4$-alkenyl, $C_2$-$C_4$-alkynyl, halo-$C_2$-$C_4$-alkynyl, phenyl, benzyl or represents phenyl or benzyl, each of which is mono- or polysubstituted by identical or different substituents from the group consisting of halogen, $C_1$-$C_3$-alkyl, halo-$C_1$-$C_3$-alkyl, $C_3$-$C_6$-cycloalkyl, halo-$C_3$-$C_6$-cycloalkyl, $R^{15}$ and $R^{16}$ independently of one another are identical or different and represent hydrogen, $C_1$-$C_4$-alkyl, $C_2$-$C_4$-alkenyl, $C_2$-$C_4$-alkynyl, $C_3$-$C_6$-cycloalkyl, phenyl, benzyl, represent phenyl or benzyl, each of which is mono- or polysubstituted by identical or different substituents from the group consisting of halogen and $C_1$-$C_3$-alkyl or $R^{15}$ and $R^{16}$ together with the adjacent nitrogen atom form a morpholino, piperidino or pyrrolidino group, $R^{17}$ represents hydrogen, represents $C_1$-$C_4$-alkyl, benzyl or halo-$C_1$-$C_4$-alkyl, each of which is optionally interrupted at least once by identical or different radicals from the group consisting of oxygen and sulphur, $R^{18}$ represents hydrogen, represents $C_1$-$C_4$-alkyl, benzyl or halo-$C_1$-$C_4$-alkyl, each of which is optionally interrupted at least once by identical or different radicals from the group consisting of oxygen and sulphur, $R^{19}$ represents optionally halogen-substituted $C_1$-$C_6$-alkyl, $C_2$-$C_6$-alkenyl, $C_1$-$C_4$-alkoxy-$C_1$-$C_4$alkyl, $C_1$-$C_3$-alkylthio-$C_1$-$C_4$-alkyl, poly-$C_1$-$C_4$-alkoxy-$C_1$-$C_4$-alkyl or represents $C_3$-$C_6$-cycloalkyl which is optionally mono- or polysubstituted by identical or different substituents from the group consisting of halogen, $C_1$-$C_4$-alkyl and $C_1$-$C_4$-alkoxy and in which optionally at least one and optionally not more than two not directly adjacent ring members are replaced by oxygen and/or sulphur, represents in each case optionally halogen- or $C_1$-$C_4$-alkyl-substituted phenyl, phenyl-$C_1$-$C_4$-alkyl, hetaryl, phenoxy-$C_1$-$C_4$-alkyl or hetaryloxy-$C_1$-$C_4$-alkyl, $R^{20}$ represents $C_1$-$C_6$-alkyl, $C_2$-$C_6$-alkenyl, $C_1$-$C_4$-alkoxy-$C_1$-$C_4$-alkyl, poly-$C_1$-$C_4$-alkoxy-$C_1$-$C_4$-alkyl, each of which is optionally mono- or polysubstituted by identical or different halogen, or represents $C_3$-$C_6$-cycloalkyl in which optionally at least one not directly adjacent ring members are replaced by oxygen and/or sulphur, or represents benzyl, $R^{21}$, $R^{22}$ and $R^{23}$ independently of one another are identical or different and represent $C_1$-$C_4$-alkyl, $C_1$-$C_4$-alkoxy, $C_1$-$C_4$-alkylamino, $C_1$-$C_4$-dialkylamino, $C_1$-$C_3$-alkylthio, $C_2$-$C_4$-alkenylthio, $C_3$-$C_6$-cycloalkylthio, each of which is optionally mono- or polysubstituted by identical or different halogen, or represent phenyl, benzyl, phenoxy or phenylthio, each of which is optionally mono- or polysubstituted by identical or different substituents from the group consisting of halogen, $C_1$-$C_6$-alkyl, $C_1$-$C_6$-alkoxy, $C_1$-$C_4$-haloalkyl, $C_1$-$C_4$-haloalkoxy, cyano and nitro, $R^{24}$ and $R^{25}$ independently of one another are identical or different and represent hydrogen, represent $C_1$-$C_6$-alkyl, $C_3$-$C_6$-cycloalkyl, $C_2$-$C_6$-alkenyl, $C_1$-$C_6$-alkoxy, $C_1$-$C_6$-alkoxy-$C_1$-$C_4$-alkyl, each of which is optionally mono- or polysubstituted by identical or different halogen, represent benzyl or phenyl, optionally mono- or polysubstituted by identical or different substituents from the group consisting of halogen and $C_1$-$C_4$-alkyl or $R^{24}$ and $R^{25}$ together with the adjacent nitrogen atom form a morpholino, piperidino or pyrrolidino group, $R^{31}$ represents halogen, cyano, nitro, $C_1$-$C_6$-alkyl, halo-$C_1$-$C_6$-alkyl, $C_3$-$C_6$-cycloalkyl, halo-$C_3$-$C_6$-cycloalkyl, $C_2$-$C_6$-alkenyl, halo-$C_2$-$C_6$-alkenyl, $C_2$-$C_6$-alkynyl, halo-$C_2$-$C_6$-alkynyl, $C_1$-$C_6$-alkoxy, halo-$C_1$-$C_6$-alkoxy, $C_3$-$C_6$-cycloalkoxy, halo-$C_3$-$C_6$-cycloalkoxy, $C_1$-$C_6$-alkynyloxy, halo-$C_1$-$C_6$-alkynyloxy, $C_2$-$C_6$-alkenyloxy, halo-$C_2$-$C_6$-alkenyloxy, $C_1$-$C_3$-alkylthio, $C_1$-$C_3$-alkylsulphinyl, $C_1$-$C_3$-alkylsulphonyl, halo-$C_1$-$C_3$-alkylthio, halo-$C_1$-$C_3$-alkylsulphinyl, $C_1$-$C_3$-alkylsulphonyl, $C_1$-$C_6$-alkylcarbonyl, $C_1$-$C_6$-alkoxycarbonyl, $C_1$-$C_6$-alkylcarbamoyl, amino, $C_1$-$C_6$-alkylamino or $C_1$-$C_6$-dialkylamino, $R^{32}$ represents hydrogen, halogen, cyano, nitro, $C_1$-$C_6$-alkyl, halo-$C_1$-$C_6$-alkyl, $C_3$-$C_6$-cycloalkyl, halo-$C_3$-$C_6$-cycloalkyl, $C_2$-$C_6$-alkenyl, halo-$C_2$-$C_6$-alkenyl, $C_2$-$C_6$-alkynyl, halo-$C_2$-$C_6$-alkynyl, $C_1$-$C_3$-alkylsulphonyl, $C_1$-$C_3$-alkylsulphonyl, $C_1$-$C_6$-alkylcarbonyl, $C_1$-$C_6$-alkoxycarbonyl, $C_1$-$C_6$-alkylcarbamoyl, amino, $C_1$-$C_6$-alkylamino or $C_1$-$C_6$-dialkylamino, n represents the number 0, 1, 2, 3, 4, 5 or 6, P represents the number 0, 1 or 2, or if Q, Y and $R^5$ together represent the group $CH_2$=, then G represents methyl, ethyl or benzyl (a).

3. The compound according to claim 1, in which if

Q represents a bond, —$CH_2$—, —CH=CH— or —$CH_2CH_2$—, then

Y represents the groups —$OR^6$, —$CO_2R^7$, —CH=$CH_2$, cyano, —$CR^{10}$=O, —$CR^{10}$=N—$OR^{13}$, —CH (OR¹⁷OR¹⁸), S(O)$_p$R⁶, —SCN, —CONR⁸R⁹, —CH(CN)₂, —CH(OH)R⁶, halogen, —OC=MR¹⁰, —S(C=M)R¹⁰, —O(C=M)NR¹¹R¹², —O(C=M)OR⁷, —NH(C=M)OR⁷, or represents the group W, or Q, Y and R⁵ together form one of the groups

[chemical structures]

W represents

[chemical structures]

G represents hydrogen, ethyl or benzyl or represents one of the groups

[chemical structure] (b)

[chemical structure R¹⁹]

[chemical structure R²⁰] (c)

R¹ represents methyl, ethyl, methoxy, ethoxy, halogen or cyclopropyl,
R² represents methyl, ethyl or 4-chlorophenyl,
R³ represents hydrogen, methyl, ethyl or cyclopropyl,
R⁴ represents hydrogen, methyl or ethyl,
R⁵ represents hydrogen,
R⁶ represents hydrogen, methyl, ethyl, —CH₂—CH(CH₃)₂, —CH₂—CH=CH₂, cyano, trifluoromethyl, methoxymethyl, 2-benzoxazolyl, 4,5-dimethylthiazol-2-yl, 2-oxazolyl, 2-tetrahydrofuryl or the 2-pyranyl group,
R⁷ represents hydrogen, methyl, ethyl, isopropyl or n-propyl,
R⁸ represents hydrogen or methyl,
R⁹ represents hydrogen or methyl,
or R⁸ and R⁹ together with the nitrogen atom form the group

[morpholine structure]

R¹⁰ represents hydrogen, methyl, t-butyl, fluoromethyl, difluoromethyl or trifluoromethyl,
R¹¹ represents hydrogen or methyl,
R¹² represents hydrogen, methyl, benzyl or phenyl,
R¹³ represents hydrogen, methyl, isopropyl, —CH₂CH=CCl₂, —CH₂CH=CH₂, —CH₂C≡CH or —CH₂C₃H₅,
R¹⁷ represents methyl, ethyl or n-propyl
R¹⁸ represents methyl, ethyl or n-propyl,
R¹⁹ represents C₁-C₄-alkyl
R²⁰ represents methyl, ethyl or isopropyl,
p represents 0 or 2,
M represents oxygen or sulphur,
or if
Q, Y and R⁵ together represent the group CH₂=,
then
G represents methyl, ethyl or benzyl (a).

4. The compound according to claim 1, in which
Q represents a bond, —CH₂—, —CH₂CH₂— or —CH=CH—,
Y represents the groups —OR⁶, —CO₂R⁷, —CH=CH₂, cyano, —CR¹⁰=O, —CR¹⁰=N—OR¹³, —CH(OR¹⁷OR¹⁸), S(O)$_p$R⁶, —SCN, —CONR⁸R⁹, —CH(CN)₂, —CH(OH)R⁶, bromine, —O(C=O)R¹⁰, —S(C=P)R¹⁰, —O(C=O)NR¹¹R¹², or represents the group W, or Q, Y and R⁵ together form one of the groups

[chemical structures]

W represents

[chemical structures]

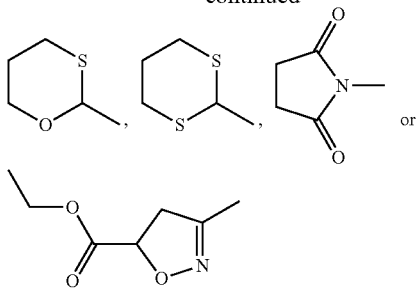

G represents hydrogen, ethyl, benzyl (a) or represents one of the groups

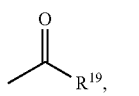 (b)

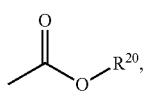 (c)

R¹ represents methyl or ethyl,
R² represents methyl,
R³ represents hydrogen,
R⁴ represents methyl or ethyl,
R⁵ represents hydrogen,
R⁶ represents hydrogen, methyl, ethyl, —CH₂—CH (CH₃)₂, —CH₂—CH=CH₂, trifluoromethyl, methoxymethyl, 2-benzoxazolyl, 4,5-dimethylthiazol-2-yl, 2-oxazolyl, 2-tetrahydrofuryl or the 2-pyranyl group,
R⁷ represents hydrogen, methyl or ethyl,
R⁸ represents hydrogen or methyl,
R⁹ represents hydrogen or methyl,
or R⁸ and R⁹ together with the nitrogen atom represent the group

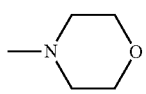

R¹⁰ represents hydrogen, methyl, t-butyl or trifluoromethyl,
R¹¹ represents hydrogen or methyl,
R¹² represents hydrogen, methyl, benzyl or phenyl,
R¹³ represents hydrogen, methyl, isopropyl, —CH₂CH=CCl₂, —CH₂CH=CH₂, —CH₂C≡CH or —CH₂C₃H₅,
R¹⁷ represents methyl or ethyl,
R¹⁸ represents methyl or ethyl,
R¹⁹ represents ethyl, tert-butyl or isopropyl,
R²⁰ represents methyl, ethyl or isopropyl,
P represents 0 or 2.

5. The compound according to claim 1, in which
Q, Y and R⁵ together represent the group CH₂=,
G represents benzyl (a),
R¹ represents ethyl,
R² represents methyl,
R³ represents hydrogen,
R⁴ represents ethyl.

6. A composition for controlling pests and/or unwanted vegetation, comprising at least one compound of the formula (I) according to claim 1.

7. A method for controlling animal pests and/or unwanted vegetation, comprising applying said compound of the formula (I) according to claim 1, to pests, unwanted vegetation and/or a habitat thereof.

8. The compound of the formula (I) according to claim 1, capable of being used for controlling animal pests and/or unwanted vegetation.

9. A process for preparing a composition for controlling pests and/or unwanted vegetation, comprising mixing said compound of the formula (I) according to claim 1 with an extender and/or surfactant.

10. A composition comprising an effective amount of an active compound combination comprising, as components,
(a') at least one compound of the formula (I) according to claim 1
and
(b') at least one crop plant compatibility-improving compound.

11. A method for controlling unwanted vegetation, comprising applying said composition according to claim 10 to a plant and/or surroundings thereof.

12. The composition according to claim 10, capable of being used for controlling unwanted vegetation.

13. A method for controlling unwanted vegetation, comprising applying said compound of the formula (I) according to claim 1, and a crop plant compatibility-improving compound to a plant and/or surroundings thereof separately in close temporal succession.

14. A method for controlling unwanted vegetation, comprising applying a compound of the formula (I) according to claim 10 and the crop plant compatibility-improving compound to a plant and/or surroundings thereof separately in close temporal succession.

* * * * *